United States Patent
Auberson et al.

(10) Patent No.: US 7,612,055 B2
(45) Date of Patent: Nov. 3, 2009

(54) MACROCYCLIC LACTAMS AND PHARMACEUTICAL USE THEREOF

(75) Inventors: Yves Auberson, Allschwil (CH); Claudia Betschart, Basel (CH); Ralf Glatthar, Bad Säckingen (DE); Kurt Laumen, March (DE); Rainer Machauer, Freiburg (DE); Marina Tintelnot-Blomley, Maulburg (DE); Thomas J. Troxler, Wahlen (CH); Siem Jacob Veenstra, Lörrach (DE)

(73) Assignee: Novartis AG, Basel (CH)

( * ) Notice: Subject to any disclaimer, the term of this patent is extended or adjusted under 35 U.S.C. 154(b) by 32 days.

(21) Appl. No.: 10/577,260

(22) PCT Filed: Nov. 4, 2004

(86) PCT No.: PCT/EP2004/012497

§ 371 (c)(1),
(2), (4) Date: Jun. 2, 2006

(87) PCT Pub. No.: WO2005/049585

PCT Pub. Date: Jun. 2, 2005

(65) Prior Publication Data

US 2007/0072792 A1    Mar. 29, 2007

(30) Foreign Application Priority Data

Nov. 5, 2003    (GB)    .................. 0325830.8

(51) Int. Cl.
*A01N 43/00*    (2006.01)
*A61K 31/33*    (2006.01)
*C07D 245/00*    (2006.01)

(52) U.S. Cl. ...................................... 514/183; 540/470

(58) Field of Classification Search ........................ None
See application file for complete search history.

(56) References Cited

FOREIGN PATENT DOCUMENTS

EP    0 675 122 A2    10/1995
WO    WO 92/18490 A1    10/1992

OTHER PUBLICATIONS

Hardy et al. Neuron, 2006, 52, 3-13.*
Ripka et al. Bioorganic and Medicinal Chemistry Letters, 1998, 8, 357-360.*
Smith, R.A., et al., "Design, Synthesis, and Activity of Conformationally-Constrained Macrocyclic Peptide-Based Inhibitors of HIV Protease," *Bioorg. & Med. Chem. Lett.* 4(18):2217-2222 (1994).

* cited by examiner

*Primary Examiner*—James O Wilson
*Assistant Examiner*—Noble Jarrell
(74) *Attorney, Agent, or Firm*—Foley & Lardner LLP

(57) ABSTRACT

The present invention relates to novel macrocyclic compounds of the formula

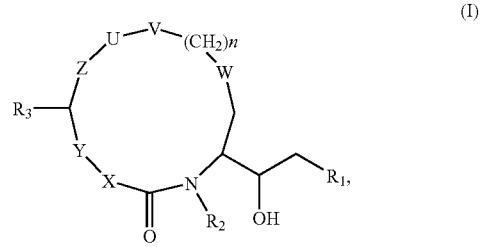

wherein $R_1$, $R_2$, $R_3$, U, V, W, X, Y, Z and n are as defined in the specification, the number of ring atoms included in the macrocyclic ring being 14, 15, 16 or 17, in free base form or in acid addition salt form, to their preparation, to their use as pharmaceuticals and to pharmaceutical compositions comprising them.

3 Claims, No Drawings

MACROCYCLIC LACTAMS AND PHARMACEUTICAL USE THEREOF

The present invention relates to novel macrocyclic compounds, to their preparation, to their use as pharmaceuticals and to pharmaceutical compositions comprising them.

More particularly the invention relates to compounds of the formula

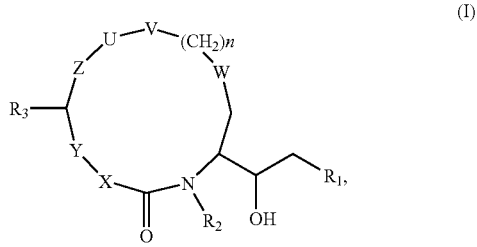

(I)

in which $R_1$ is $CH(R_e)C(=O)N(R_a)R_b$ or $(CH_2)_kN(R_c)R_d$, wherein k is 0, 1 or 2;

$R_a$ and $R_b$, independently, are hydrogen or an optionally substituted $(C_{1-8})$alkyl, $(C_{3-7})$cycloalkyl, $(C_{3-7})$cycloalkyl$(C_{1-4})$alkyl, aryl, aryl$(C_{1-4})$alkyl, heteroaryl or heteroaryl$(C_{1-4})$alkyl group, $R_c$ and $R_d$, independently, are hydrogen or an optionally substituted $(C_{1-8})$alkyl, $(C_{3-7})$cycloalkyl, $(C_{3-7})$cycloalkyl$(C_{1-4})$alkyl, aryl, aryl$(C_{1-4})$alkyl, heteroaryl, heteroaryl$(C_{1-4})$alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinolin-4-yl, 1,2,3,4-tetrahydro-isoquinolin-4-yl, 1,2,3,4-tetrahydro-naphthalen-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl or 1,3,4,5-tetrahydro-benzo[c]oxepin-5-yl group, or $R_a$ and $R_b$, or $R_c$ and $R_d$, together with the nitrogen to which they are attached, form an optionally substituted pyrrolidinyl, 1-piperidinyl, 4-morpholinyl or piperazinyl group; and $R_e$ is optionally substituted $(C_{1-8})$alkyl, $(C_{1-4})$alkoxy$(C_{1-4})$alkyl, $(C_{3-7})$cycloalkyl or $(C_{3-7})$cycloalkyl$(C_{1-4})$alkyl;

$R_2$ is hydrogen or $(C_{1-4})$alkyl;

$R_3$ is hydrogen, $(C_{1-6})$alkyl or an optionally substituted $(C_{1-6})$alkylOC(=O)NH, $(C_{3-7})$cycloalkylOC(=O)NH, $(C_{3-7})$cycloalkyl$(C_{1-4})$alkylOC(=O)NH, aryl$(C_{1-4})$alkylOC(=O)NH, heteroaryl$(C_{1-4})$alkylOC(=O)NH, $(C_{1-4})$alkylC(=O)NH, $(C_{3-7})$cycloalkylC(=O)NH, arylC(=O)NH, aryl$(C_{1-4})$alkylC(=O)NH, heteroarylC(=O)NH or heteroaryl$(C_{1-4})$alkylC(=O)NH group;

U is a bond, $CF_2$, $CF_2CF_2$, CHF, CHFCHF, cycloprop-1,2-ylene, $(C_{1-3})$alkylenoxy, $(C_{1-8})$alkylene, $NR_g$ or an aromatic or heteroaromatic ring, which ring is optionally substituted with halogen, $(C_{1-4})$alkoxy, hydroxy or $(C_{1-4})$alkyl, whereby Z and V are in ortho- or meta-position to each other, wherein $R_g$ is hydrogen, $(C_{1-8})$alkyl or $(C_{3-7})$cycloalkyl;

V is CH=CH, cycloprop-1,2-ylene, $CH_2CH(OH)$, $CH(OH)CH_2$ or $CR_hR_hCR_hR_h$, wherein each $R_h$, independently, is hydrogen, fluorine or $(C_{1-4})$alkyl;

W is $(C_{1-6})$alkylene, O, S, $S(=O)_2$, C(=O), C(=O)O, OC(=O), $N(R_f)C(=O)$, $C(=O)NR_f$ or $NR_f$, wherein $R_f$ is hydrogen or $(C_{1-4})$alkyl;

X is an optionally substituted $(C_{1-4})$alkanylylidene, $(C_{1-4})$alkylene, $(C_{3-7})$cycloalkylene, piperidin-diyl, pyrrolidin-diyl, benzothiazole-4,6-diyl, benzoxazole-4,6-diyl, 1H-benzotriazole-4,6-diyl, imidazo[1,2-a]pyridine-6,8-diyl, benzo[1,2,5]oxadiazole-4,6-diyl, benzo[1,2,5]thiadiazole-4,6-diyl, 1H-indole-5,7-diyl, 1H-indole-4,6-diyl, 1H-benzimidazole-4,6-diyl or 1H-indazole-1,6-diyl group or an optionally substituted aromatic or heteroaromatic ring, whereby Y and C(=O)NR_2 are in meta-position to each other;

Y is a bond, O, $S(=O)_2$, $S(=O)_2NR_g$, $N(R_g)S(=O)_2$, $NR_g$, $C(R_g)OH$, $C(=O)NR_g$, $N(R_g)C(=O)$, $C(=O)N(R_g)O$ or $ON(R_g)C(=O)$, wherein $R_g$ is hydrogen, $(C_{1-8})$alkyl or $(C_{3-7})$cycloalkyl;

Z is O, $CH_2$, $CF_2$, CHF, cycloprop-1,2-ylene or a bond; and n is 0 to 5, the number of ring atoms included in the macrocyclic ring being 14, 15, 16 or 17, in free base form or in acid addition salt form.

On account of the asymmetrical carbon atoms present in the compounds of the formula I and their salts, the compounds may exist in optically active form or in the form of mixtures of optical isomers, e.g. in the form of racemic mixtures. All optical isomers and their mixtures, including the racemic mixtures, are part of the present invention.

Halogen denotes fluorine, bromine, chlorine or iodine.

Optional substituents on alkyl, alkoxy or cycloalkyl groups or moieties, or, when $R_a$ and $R_b$, or $R_c$ and $R_d$, together with the nitrogen to which they are attached form a substituted pyrrolidinyl, 1-piperidinyl, 4-morpholinyl or piperazinyl group, on the last mentioned substituted groups, may be one to three groups independently selected from hydroxy, hydroxy$(C_{1-4})$alkyl, $(C_{1-4})$alkoxy, $(C_{1-4})$alkoxy$(C_{1-4})$alkyl, $(C_{1-4})$alkoxy$(C_{1-4})$alkoxy, $(C_{1-4})$alkylsulfanyl, $(C_{1-4})$alkoxycarbonyl, $(C_{1-4})$alkylcarbonyloxy, $(C_{1-4})$alkylcarbonyl, $(C_{1-4})$alkylsulfonyl, cyano, oxo and $(C_{3-7})$cycloalkyl.

Optional substituents on chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-yl, 1,2,3,4-tetrahydro-quinolin-4-yl, 1,2,3,4-tetrahydro-isoquinolin-4-yl, 1,2,3,4-tetrahydro-naphthalen-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]-oxathiin-4-yl, 2,3,4,5-tetrahydro-benzo[b]oxepin-5-yl or 1,3,4,5-tetrahydro-benzo[c]oxepin-5-yl, benzothiazole-4,6-diyl, benzoxazole-4,6-diyl, 1H-benzotriazole-4,6-diyl, imidazo-[1,2-a]pyridine-6,8-diyl, benzo[1,2,5]oxadiazole-4,6-diyl, benzo[1,2,5]thiadiazole-4,6-diyl, 1H-indole-5,7-diyl, 1H-indole-4,6-diyl, 1H-benzimidazole-4,6-diyl, 1H-indazole-1,6-diyl, aryl or heteroaryl rings or moieties are one to four, especially one to three, groups independently selected from hydroxy, $(C_{1-8})$alkyl, $(C_{1-6})$alkoxy, $S(=O)_2(C_{1-4})$alkyl, $(C_{3-7})$cycloalkyl, $(C_{3-7})$cycloalkyl$(C_{1-4})$alkyl, cyano, nitro, trifluoromethyl, halogen, aryl, heteroaryl and optionally substituted carbamoyl.

When $R_c$ and/or $R_d$ is substituted aryl or heteroaryl, optional substituents may further be one to three groups selected from benzyloxy, phenoxy, $S(=O)_2NH_2$, $N(H)S(=O)_2(C_{1-3})$alkyl, carboxy, $(C_{1-4})$alkoxycarbonyl, $(C_{1-4})$alkylcarbamoyl, $(C_{1-4})$alkylsulfonyl, $(C_{1-4})$alkylcarbonyloxy, $(C_{1-4})$alkylcarbonyl, hydroxy$(C_{1-4})$alkyl and optionally substituted amino.

Optional substituents on alkanylylidene, alkylene, alkylenoxy, cycloalkylene, piperidin-diyl or pyrrolidin-diyl groups or moieties may be one to three groups independently selected from hydroxy, hydroxy$(C_{1-4})$alkyl, $(C_{1-4})$alkoxy, $(C_{1-4})$alkoxy$(C_{1-4})$alkyl, $(C_{1-4})$alkoxy$(C_{1-4})$alkoxy, $(C_{1-4})$alkylsulfanyl, $(C_{1-4})$alkoxycarbonyl, $(C_{1-4})$alkylcarbonyloxy, $(C_{1-4})$alkylcarbonyl, $(C_{1-4})$alkylsulfonyl, cyano, oxo, carboxy, carbamoyl and $(C_{3-7})$cycloalkyl.

Optional substituents on amino groups can be one or two groups independently selected from $(C_{1-4})$alkyl, $(C_{1-4})$alkoxy $(C_{1-4})$alkyl, $(C_{1-4})$alkoxycarbonyl, aryl$(C_{1-4})$alkoxycarbonyl and heteroaryl$(C_{1-4})$alkoxycarbonyl.

Optional substituents on carbamoyl can be one or two groups selected from $(C_{1-4})$alkyl and $(C_{1-4})$alkoxy$(C_{1-4})$alkyl.

Aryl is naphthyl or preferably phenyl.

Heteroaryl is an aromatic 5- or 6-membered ring, in which 1, 2 or 3 ring atoms are hetero atoms independently selected from O, N and S, such as thiazolyl, oxazolyl or preferably pyridyl.

Any non-cyclic carbon containing group or moiety with more than 1 carbon atom is straight-chain or branched.

Unless defined otherwise, carbon containing groups, moieties or molecules contain 1 to 8, preferably 1 to 6, more preferably 1 to 4, most preferably 1 or 2, carbon atoms.

In preferred embodiments, the invention relates to a compound of the formula I, in free base form or in acid addition salt form, in which (1) $R_1$ is $CH(R_e)C(=O)N(R_a)R_b$ and $R_a$, $R_b$ and $R_e$ have one of the meanings defined hereinbefore;

(2) $R_1$ is $CH(R_e)C(=O)N(R_a)R_b$, $R_b$ and $R_e$ have one of the meanings defined hereinbefore and $R_a$ is hydrogen;

(3) $R_1$ is $CH(R_e)C(=O)N(R_a)R_b$, $R_a$ and $R_e$ have one of the meanings defined hereinbefore and $R_b$ is $(C_{1-8})$alkyl, preferably $(C_{1-5})$alkyl, more preferably n-butyl;

(4) $R_1$ is $CH(R_e)C(=O)N(R_a)R_b$, $R_a$ and $R_b$ have one of the meanings defined hereinbefore and $R_e$ is $(C_{1-8})$alkyl, preferably $(C_{1-4})$alkyl, more preferably methyl;

(5) $R_1$ is $(CH_2)_kN(R_c)R_d$ and $R_c$, $R_d$ and k have one of the meanings defined hereinbefore;

(6) $R_1$ is $(CH_2)_kN(R_c)R_d$, $R_c$ and $R_d$ have one of the meanings defined hereinbefore and k is 0;

(7) $R_1$ is $(CH_2)_kN(R_c)R_d$, k and $R_d$ have one of the meanings defined hereinbefore and $R_c$ is hydrogen;

(8) $R_1$ is $(CH_2)_kN(R_c)R_d$, k and $R_c$ have one of the meanings defined hereinbefore and $R_d$ is an optionally substituted aryl$(C_{1-4})$alkyl, heteroaryl$(C_{1-4})$alkyl or chroman-4-yl group, preferably an optionally substituted phenyl$(C_{1-4})$alkyl, pyridyl$(C_{1-4})$alkyl or chroman-4-yl group, more preferably an optionally substituted phenyl$(C_{1-2})$alkyl, pyridyl$(C_{1-2})$alkyl or chroman-4-yl group, more preferably a phenyl$(C_{1-2})$alkyl, pyridyl$(C_{1-2})$alkyl or chroman-4-yl group optionally substituted by 1 to 4 substituents, independently selected from the group, consisting of $(C_{1-8})$alkyl, $(C_{1-4})$alkoxy, $(C_{3-7})$cycloalkyl and halogen, preferably phenyl$(C_{1-2})$alkyl substituted by 1 or 2 substituents, independently selected from the group, consisting of $(C_{1-8})$alkyl, $(C_{1-4})$alkoxy and $(C_{3-7})$cycloalkyl, preferably 3-$(C_{1-8})$alkylbenzyl, more preferably 3-isopropylbenzyl, preferably 3-$(C_{1-4})$alkoxybenzyl, more preferably 3-methoxybenzyl, preferably 3-$(C_{3-7})$cycloalkylbenzyl, more preferably 3-cyclopropylbenzyl, preferably 2-(3,4-di$(C_{1-4})$ alkoxyphenyl)ethyl, more preferably 2-(3,4-dimethoxyphenyl)ethyl, preferably pyridyl$(C_{1-2})$alkyl optionally monosubstituted by halogen or $(C_{3-7})$cycloalkyl, preferably unsubstituted 2-(pyrid-4-yl)ethyl, preferably 5-halogenopyrid-3-ylmethyl, more preferably 5-bromopyrid-3-ylmethyl, preferably 5-$(C_{3-7})$cycloalkylpyrid-3-ylmethyl, more preferably 5-cyclopropylpyrid-3-ylmethyl, preferably 2-$(C_{3-7})$cycloalkylpyrid-4-ylmethyl, more preferably 2-cyclopropylpyrid-4-ylmethyl, preferably chroman-4-yl substituted by 1 to 4, more preferably by 1 to 3, substituents, independently selected from the group, consisting of $(C_{1-8})$alkyl, more preferably of $(C_{1-4})$alkyl, preferably 2,2,6-tri$(C_{1-4})$alkylchroman-4-yl, more preferably 2,2-dimethyl-6-isopropyl-chroman-4-yl;

(9) $R_2$ is hydrogen;

(10) $R_3$ is hydrogen, $(C_{1-6})$alkyl or an optionally substituted $(C_{1-6})$alkylOC(=O)NH, $(C_{1-4})$alkylC(=O)NH or heteroarylC(=O)NH group, preferably hydrogen, $(C_{1-4})$alkyl or an unsubstituted $(C_{1-6})$alkylOC(=O)NH, $(C_{1-4})$alkylC(=O)NH or pyridylC(=O)NH group, more preferably hydrogen, $(C_{1-2})$alkyl or an unsubstituted $(C_{1-4})$alkylOC(=O)NH, $(C_{1-2})$alkylC(=O)NH or pyridylC(=O)NH group, preferably hydrogen, preferably ethyl, preferably tert-butoxycarbonylamino, preferably acetylamino, preferably pyrid-4-ylcarbonylamino;

(11) U is a bond, $(C_{1-3})$alkylenoxy, $(C_{1-8})$alkylene, NH or an aromatic ring, which ring is optionally substituted with $(C_{1-4})$alkyl, whereby Z and V are in ortho- or meta-position to each other, preferably a bond, $(C_{1-3})$alkylenoxy, $(C_{1-8})$alkylene, NH or a 1,2- or 1,3-phenylene group, which group is optionally substituted with $(C_{1-4})$alkyl, more preferably a bond, $(C_{1-3})$alkylenoxy, $(C_{1-6})$alkylene, NH, unsubstituted 1,2-phenylene or 1,3-phenylene optionally monosubstituted with $(C_{1-4})$alkyl, preferably a bond, preferably $CH_2$, preferably $CH_2CH_2$, preferably $CH_2CH_2CH_2$, preferably $CH(CH_3)CH_2$, preferably $CH_2CH(CH_3)$, preferably $CH(CH_3)$, preferably $CH(CH_2CH_3)$, preferably $CH(CH_2CH_3)CH_2$, preferably $OCH_2CH_2CH_2$, preferably NH, preferably unsubstituted 1,2-phenylene, preferably unsubstituted 1,3-phenylene, preferably 5-methyl-1,3-phenylene;

(12) V is CH=CH or preferably $CH_2CH_2$;

(13) W is $(C_{1-6})$alkylene, preferably $(C_{1-4})$alkylene, more preferably $(C_{1-2})$alkylene, preferably $CH(CH_3)$;

(14) X is optionally substituted $(C_{1-4})$alkylene or an optionally substituted aromatic or heteroaromatic ring, whereby Y and $C(=O)NR_2$ are in meta-position to each other, preferably unsubstituted $(C_{1-4})$alkylene or a 1,3-phenylene or 2,4-pyridylene group, which group is optionally substituted with $(C_{1-4})$alkyl, $(C_{1-6})$alkoxy, $S(=O)_2(C_{1-4})$alkyl or heteroaryl, more preferably unsubstituted $(C_{1-3})$alkylene or a 1,3-phenylene or 2,4-pyridylene group, which group is optionally monosubstituted with $(C_{1-4})$alkyl, $(C_{1-4})$alkoxy, $S(=O)_2(C_{1-4})$alkyl or oxazolyl, preferably $CH_2$, preferably $CH_2CH_2$, preferably $CH_2CH_2CH_2$, preferably $CH_2CH(CH_3)$, preferably $CH(CH_3)$, preferably unsubstituted 1,3-phenylene, preferably 5-methyl-1,3-phenylene, preferably 5-methoxy-1,3-phenylene, preferably 5-ethoxy-1,3-phenylene, preferably 5-isopropoxy-1,3-phenylene, preferably 5-methylsulfonyl-1,3-phenylene, preferably 5-oxazol-2-yl-1,3-phenylene, preferably 6-methyl-2,4-pyridylene, preferably 6-methoxy-2,4-pyridylene, preferably 6-ethoxy-2,4-pyridylene;

(15) Y is O, S(=O)$_2$, N(R$_g$)S(=O)$_2$, NR$_g$, C(=O)NR$_g$, N(R$_g$)C(=O) or ON(R$_g$)C(=O), wherein R$_g$ is hydrogen, (C$_{1-4}$)alkyl or (C$_{3-7}$)cycloalkyl,
preferably O, S(=O)$_2$, N(R$_g$)S(=O)$_2$, NH, C(=O)NR$_g$, N(R$_g$)C(=O) or ON(R$_g$)C(=O), wherein R$_g$ is hydrogen, (C$_{1-4}$)alkyl or cyclopropyl,
preferably O, preferably S(=O)$_2$, preferably N(CH$_3$)S(=O)$_2$, preferably NH, preferably C(=O)NH, preferably C(=O)NCH$_3$, preferably N(H)C(=O), preferably N(CH$_3$)C(=O), preferably N(CH$_2$CH$_3$)C(=O), preferably N(CH$_2$CH$_2$CH$_3$)C(=O), preferably N(cyclopropyl)C(=O), preferably ON(CH$_2$CH$_3$)C(=O);

(16) Z is O, CH$_2$ or a bond, preferably O, preferably CH$_2$, preferably a bond;

(17) n is 0 to 4, preferably 0, preferably 1, preferably 2, preferably 3, preferably 4;

(18) the number of ring atoms included in the macrocyclic ring is 14;

(19) the number of ring atoms included in the macrocyclic ring is 15;

(20) the number of ring atoms included in the macrocyclic ring is 16;

(21) the number of ring atoms included in the macrocyclic ring is 17.

In especially preferred embodiments, the invention relates to one or more than one of the compounds of the formula I mentioned in the Examples hereinafter, in free base form or in acid addition salt form.

In a further aspect, the invention relates to a process for the preparation of the compounds of the formula I and their salts, comprising the steps of cyclisation by metathesis of a compound of the formula

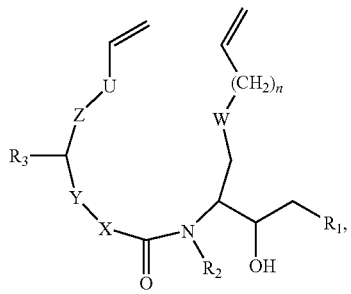

(II)

in which R$_1$, R$_2$, R$_3$, U, W, X, Y, Z and n are as defined for the formula I, in the presence of a catalyst, for instance a ruthenium, tungsten or molybdenum complex, optionally followed by reduction, oxidation or functionalisation of the resulting carbon-carbon-double bond, and of recovering the so obtainable compound of the formula I in free base form or in acid addition salt form.

The reaction can be effected according to conventional methods, for example as described in the Examples.

The working-up of the reaction mixtures and the purification of the compounds thus obtainable may be carried out in accordance with known procedures.

Acid addition salts may be produced from the free bases in known manner, and vice-versa.

Compounds of the formula I can also be prepared by further conventional processes, which processes are further aspects of the invention, e.g. as described in the Examples.

For example, compounds of the formula I, in which R$_1$ is (CH$_2$)$_k$N(R$_c$)R$_d$ and k is 0, can be prepared by reaction of a compound of the formula

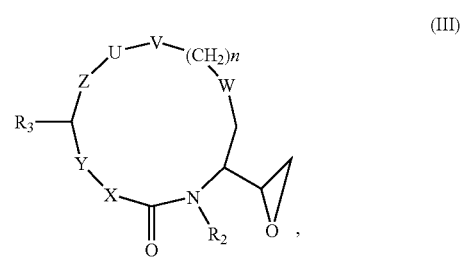

(III)

in which R$_2$, R$_3$, U, V, W, X, Y, Z and n are as defined for the formula I, with an amine of the formula HN(R$_c$)R$_d$ (IV), in which R$_c$ and R$_d$ are as defined for the formula I, and by recovering the so obtainable compound of the formula I in free base form or in acid addition salt form.

For example, compounds of the formula I, in which R$_1$ is CH(R$_e$)C(=O)N(R$_a$)R$_b$, can be prepared by reaction of a compound of the formula (V)

in which R$_2$, R$_3$, R$_e$, U, V, W, X, Y, Z and n are as defined for the formula I, with an amine of the formula HN(R$_a$)R$_b$ (VI), in which R$_a$ and R$_b$ are as defined for the formula I, and by recovering the so obtainable compound of the formula I in free base form or in acid addition salt form.

The starting materials of the formulae II, III, IV, V and VI are known or may be prepared according to conventional procedures starting from known compounds, for example as described in the Examples.

Compounds of the formula I and their pharmaceutically acceptable acid addition salts, hereinafter referred to as agents of the invention, exhibit valuable pharmacological properties when tested in vitro and in animals, and are therefore useful as pharmaceuticals.

The agents of the invention are inhibitors of aspartic proteases and can be used for the treatment of disorders involving processing by such enzymes. Particularly they inhibit beta-secretase and as such inhibit the generation of beta-amyloid and the subsequent aggregation into oligomers and fibrils.

Test 1: Inhibition of Human BACE

Recombinant BACE (extracellular domain, expressed in baculovirus and purified using standard methods) at 6 nM concentration is incubated with the test compound at various concentrations for 1 hour at room temperature in 100 mM acetate buffer, pH 4.5, containing 0.1% CHAPS. Synthetic peptide substrate Mca-Ser-Glu-Val-Asn-Leu-Asp-Ala-Glu-Phe-Lys(DNP) is added to a final concentration of 3 μM and the increase in fluorescence is recorded at excitation of 325 nm and emission at 400 nm in a microplate spectro-fluorimeter for 20 minutes in 1-minute intervals. $IC_{50}$ values are calculated from percentage of inhibition of BACE-activity as a function of the test compound concentration.

Test 2: Inhibition of Human BACE-2

Recombinant BACE-2 (extracellular domain, expressed in baculovirus and purified using standard methods) at 2.5 nM concentrations is incubated with the test compound at various concentrations for 1 hour at room temperature in 100 mM acetate buffer, pH 4.5, containing 0.1% CHAPS. Synthetic peptide substrate Mca-Ser-Glu-Val-Asn-Leu-Asp-Ala-Glu-Phe-Lys(DNP) is added to a final concentration of 3 μM and the increase in fluorescence is recorded at excitation of 325 nm and emission at 400 nm in a microplate spectro-fluorimeter for 20 minutes in 1-minute intervals. $IC_{50}$ values are calculated from percentage of inhibition of BACE-2-activity as a function of the test compound concentration.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in 100 mM sodium formate buffer, pH 3.1. Synthetic peptide substrate Mca-Gly-Lys-Pro-Ile-Leu-Phe-Phe-Arg-Leu-Lys(DNP)-D-Arg-$NH_2$ is added to a final concentration of 2 μM and the increase in fluorescence is recorded at excitation of 325 nm and emission at 400 nm in a microplate spectro-fluorimeter for 20 minutes in 1-minute intervals. $IC_{50}$ values are calculated from percentage of inhibition of cathepsin D-activity as a function of the test compound concentration.

Test 4: Inhibition of Cellular Release of Amyloid Peptide 1-40

Chinese hamster ovary cells are transfected with the gene for amyloid precursor protein. Cells are plated at a density of 8000 cells/well in a 96-well microtiter plate and cultivated for 24 hours in DMEM cell culture medium containing 10% FCS. The test compound is added to the cells at various concentrations, and cells are cultivated for 24 hours in the presence of the test compound. The supernatants are collected, and the concentration of amyloid peptide 1-40 is determined using sandwich ELISA. The potency of the compound is calculated from the percentage of inhibition of amyloid peptide release as a function of the test compound concentration.

In at least one of the above-indicated tests, the agents of the invention show activity at concentrations below 20 μM.

The agents of the invention are therefore useful e.g. for the treatment and/or prevention of neurological and vascular disorders related to beta-amyloid generation and/or aggregation, such as neurodegenerative diseases like Alzheimer's disease, Down's Syndrome, memory and cognitive impairment, dementia, amyloid neuropathies, brain inflammation, nerve and brain trauma, vascular amyloidosis, or cerebral hemorrhage with amyloidosis.

Some of the agents of the invention also inhibit BACE2 (beta-site APP-cleaving enzyme 2) or Cathepsin D, close homologues of the pepsin-type aspartyl proteases and of beta-secretase. Due to the correlation of BACE2 and CathD expression with a more tumorigenic and metastatic potential of tumor cells, such inhibitors are useful for the suppression of the metastasis process associated with tumor cells.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range from about 10 to about 2000, preferably from about 10 to about 200, mg of an agent of the invention conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of neurological or vascular disorders related to beta-amyloid generation and/or aggregation.

The present invention furthermore provides a pharmaceutical composition comprising an agent of the invention in association with at least one pharmaceutical carrier or diluent. Such compositions may be manufactured in conventional manner. Unit dosage forms contain, for example, from about 1 to about 1000, preferably from about 1 to about 500, mg of an agent of the invention.

The agents of the invention can be administered alone or in combination with other pharmaceutical agents effective in the treatment of conditions mentioned above.

The pharmaceutical combination may be in the form of a unit dosage form, whereby each unit dosage will comprise a predetermined amount of the two components, in admixture with suitable pharmaceutical carriers or diluents. Alternatively, the combination may be in form of a package containing the two components separately, e.g. a pack or dispenser-device adapted for the concomitant or separate administration of the two active agents, wherein these agents are separately arranged.

Moreover the present invention provides the use of an agent of the invention, for the manufacture of a medicament for the treatment of any neurological or vascular disorders related to beta-amyloid generation and/or aggregation.

In still a further aspect, the present invention provides a method for the treatment of any neurological or vascular disorders related to beta-amyloid generation and/or aggregation, in a subject in need of such treatment, which comprises administering to such subject a therapeutically effective amount of an agent of the invention.

The following Examples illustrate the invention, but do not limit it.

EXAMPLES

| Abbreviations: | |
|---|---|
| aq. | aqueous |
| BOC | tert-butoxycarbonyl |
| CDCl3 | deuterated chloroform |
| conc. | concentrated |
| DBU | diazabicycloundecene |

-continued

Abbreviations:

| | |
|---|---|
| DCM | dichloromethane |
| DIPEA | diisopropylethylamine |
| DMPU | N,N'-dimethylpropylene urea |
| d6-DMSO | deuterated dimethylsulfoxide |
| EDC.HCl | 1-ethyl-3-[3-(dimethylamino)propyl]-carbodiimide hydrochloride |
| ES | electron spray |
| $Et_2O$ | diethyl ether |
| EtOAc | ethyl acetate |
| EtOH | ethanol |
| h | hour |
| HCl | hydrochloric acid |
| HMDS | 1,1,1,3,3,3-hexamethyl-disilazane |
| HOBt | hydroxybenzotriazole |
| HPLC | high pressure liquid chromatography |
| LC | liquid chromatography |
| LHMDS | lithium hexamethyldisilazide |
| MeCN | acetonitrile |
| min | minute |
| Mp | melting point |
| MS | mass spectroscopy |
| PL-CHO | polymer supported benzaldehyde (3 mmol/g) |
| PPTS | pyridinium-para-toluenesulfonate |
| Rf | retention factor (thin layer chromatography) |
| rt | room temperature |
| TBME | tert-butyl methyl ether |
| TFA | trifluoroacetic acid |
| THF | tetrahydrofuran |

Example 1

(3S,14R)-16-[1-Hydroxy-2-(3-methyl-benzylamino)-ethyl]-3,4,14-trimethyl-1,4-diaza-cyclohexadecane-2,5-dione A solution of 67 mg (0.2 mmol) 3(S),4,14(R)-trimethyl-16 (R/S)-oxiranyl-1,4-diaza-cyclohexadecane-2,5-dione in 92 mg (0.76 mmol) 3-methyl-benzylamine is heated at 65° C. for 2 h. The mixture is diluted with DCM, 961 mg PL-CHO (2.88 mmol) and 1 drop of glacial acetic acid are added and the mixture is shaken at rt for 4 h. The resin is filtered off and the filtrate evaporated. Purification of the residue by preparative thin layer chromatography or HPLC gives a thick brownish oil.

Rf: (DCM/methanol/acetic acid=90/9/1): 0.36
MS (EI): $[MH]^+=460.0$

The starting material can be prepared as described hereafter:

a) (3S,14R)-3,4,14-Trimethyl-16-oxiranyl-1,4diaza-cyclohexadecane-2,5-dione

To a solution of 718 mg (1.91 mmol) (3S,14R)-16-(2-chloro-1-hydroxy-ethyl)-3,4,14-trimethyl-1,4-diaza-cyclohexadecane-2,5-dione in 3.8 ml THF is added 2.3 ml 1 M NaOH dropwise at 0° C. and the reaction mixture is stirred for 2 h at 0° C. Water is added and the mixture is extracted with DCM, the combined organic layers are washed with saturated ammonium chloride and brine, dried with sodium sulfate and evaporated to give the product as a brownish oil (mixture of diastereomers).

Rf: (DCM/methanol=95/5): 0.52
MS (EI): $[MH]^+=339.3$, $[MNa]^+=361.3$ b) (3S,14R)-16-(2-Chloro-1-hydroxy-ethyl)-3,4,14-trimethyl-1,4diaza-cyclohexadecane-2,5-dione A solution of 1.24 g (3.32 mmol) of (E)-(3S,14R)-16-(2-chloro-1-hydroxy-ethyl)-3,4,14-trimethyl-1,4-diaza-cyclohexadec-10-ene-2,5-dione in 33 ml EtOH is stirred at rt in the presence of 332 mg 10% Pd/C under a hydrogen atmosphere for 1 h. More catalyst is added (332 mg) and the hydrogenation is continued for 4 h. The catalyst is filtered off and the filtrate evaporated. The residue is purified by chromatography on silica gel (DCM/methanol 95/5) and gives the title compound as a brownish foam (mixture of diastereomers).

Rf: (DCM/methanol=95/5): 0.40
MS (LC/MS): $[MH]^+=375.0/377.0$, $[MNa]^+=396.9/398.9$ c) (E)-(3S,14R)-16-(2-Chloro-1-hydroxy-ethyl)-3,4,14-trimethyl-1,4diaza-cyclohexadec-10-ene-2,5-dione A solution of 1.38 g (3.44 mmol) hept-6-enoic acid {(S)-1-[(R)-1-(2-chloro-1-hydroxy-ethyl)-3-methyl-hept-6-enyl-carbamoyl]-ethyl}-methyl-amide in 17 ml DCM is added dropwise within an hour to a refluxing solution of 146 mg [1,3-bis-(2,4,6-trimethylphenyl)-2-imidazolidinylidene)-dichloro(phenylmethylene)-(tricyclohexylphosphine)ruthenium](Grubbs II catalyst) in 340 ml DCM. The mixture is refluxed for an additional hour and the solvent evaporated. The residue is purified by chromatography on silica gel (DCM/methanol 95/5), giving the desired product as a brownish foam (mixture of diastereomers).

Rf: (DCM/methanol=95/5): 0.39 d) Hept-6-enoic acid {(S)-1-[(R)-1-(2-chloro-1-hydroxy-ethyl)-3-methyl-hept-6-enyl-carbamoyl]-ethyl}-methyl-amide A solution of 3.15 g (5 mmol) hept-6-enoic acid {(S)-1-[(R)-1-(2-chloro-acetyl)-3-methyl-hept-6-enylcarbamoyl]-ethyl}methyl-amide in 110 ml ethanol is added to a suspension of 378 mg (10 mmol) sodium borohydride in 30 ml ethanol at −78° C. The temperature is kept below −75° C. during the addition and the mixture is stirred for an additional hour. The reaction is quenched with 25 ml 1 M HCl at −78° C. and the mixture is allowed to warm to rt. After evaporation of the ethanol and addition of 50 ml 1 M HCl the mixture is extracted with EtOAc. The organic layer is washed with 1 M HCl and a half-saturated aqueous sodium chloride solution, dried with sodium sulfate and evaporated. Purification by chromatography on silica gel (cyclohexane/EtOAc 70/30 to 50/50) gives the desired product as a brown oil (mixture of diastereomers).

Rf: (cyclohexane/EtOAc=50/50): 0.30
MS (LC/MS): $[MH]^+=400.9/402.9$, $[MNa]^+=422.9/424.9$ e) Hept-6-enoic acid {(S)-1-[(R)-1-(2-chloro-acetyl)-3-methyl-hept-6-enylcarbamoyl]-ethyl}-methyl-amide A solution of 1.9 g (5.0 mmol) (R)-2-[(S)-2-(hept-6-enoyl-methyl-amino)propionylamino]-4-methyl-oct-7-enoic acid methyl ester in 37 ml THF is cooled at −78° C. and 1.45 ml (20 mmol) chloroiodomethane is added. A 1.57 M THF solution of LDA (15.9 ml, 25 mmol) is added dropwise while the temperature of the reaction mixture is maintained below −68° C., and the mixture is stirred for an additional 30 min. The reaction is carefully quenched with 7.46 ml glacial acetic acid (130 mmol) while the temperature is maintained below −65°

C. After stirring for 15 min at −78° C. the mixture is allowed to warm to 0° C. and 75 ml of a half-saturated aqueous sodium chloride solution are added. The mixture is extracted with TBME, washed with 1 M sodium bicarbonate, 1 M sodium sulfite and water, dried with sodium sulfate and evaporated. The product (mixture of diastereomers) is used for the next step without further purification.

Rf: (cyclohexane/EtOAc=50/50): 0.45
MS (LC/MS): [MNa]$^+$=420.9/422.9 f) (R)-2-[(S)-2-(Hept-6-enoyl-methyl-amino)-propionylamino]-4-methyl-oct-7-enoic acid methyl ester To a solution of 2.63 g (20.5 mmol) 6-heptenoic acid and 4.12 g (26.1 mmol) HOBt in 100 ml DCM at 0° C. are added 4.29 g (22.37 mmol) EDC.HCl, after 10 minutes followed by 5.04 g (18.64 mmol) (R)-4-methyl-2-((S)-2-methylamino-propionylamino)-oct-7-enoic acid methyl ester. The mixture is allowed to warm to rt and stirring is continued for 3 days. The reaction mixture is cooled to 0° C., 186 ml 0.5 M HCl is added and the layers separated. The aqueous phase is extracted with DCM/ethanol 8:2 twice, the combined organic layers are washed with 1 M potassium bicarbonate, water, dried with sodium sulfate and evaporated. Purification by chromatography on silica gel (DCM/methanol 98/2) gives the product as a brownish oil (mixture of diastereomers).

Rf: (DCM/methanol=95/5): 0.73
MS (EI+): [MNa]$^+$=403.3
$^1$H-NMR (400 MHz, d6-DMSO): 8.09-8.00 (m, 1H), 5.83-5.68 (m, 2H), 5.04-4.89 (m, 4H), 4.37-4.26 (m, 1H), 3.61 (s, 1.5H), 3.60 (s, 1.5H), 2.85-2.69 (m, 3H), 2.34-2.23 (m, 2H), 2.09-1.93 (m, 4H), 1.75-1.60 (m, 1H), 1.55-1.08 (m, 7H), 1.18 (d, 3H), 0.89-0.79 (m, 3H)

g) (R)-4-Methyl-2-((S)-2-methylamino-propionylamino)-oct-7-enoic acid methyl ester To a solution of 7.84 g (22.4 mmol) [(S)-1-((R)-1-cyano-3-methyl-hept-6-enylcarbamoyl)-ethyl]-methyl-carbamic acid tert-butyl ester in 67 ml methanol is added slowly 138 ml of a 6.5 M solution of HCl in Et$_2$O (896 mmol) at 0° C. The mixture is stirred at rt for 1 h. The mixture is cooled with an ice bath and water is added. The pH of the reaction mixture is adjusted to pH 8 by addition of 89.7 g (896 mmol) potassium bicarbonate. The mixture is extracted with DCM three times, the combined organic layers are dried with sodium sulfate and evaporated. The product is obtained as a brownish oil (mixture of diastereomers) and used for the next step without further purification.

Rf: (DCM/methanol=95/5): 0.22
MS (EI): [MH]$^+$=271.0
$^1$H-NMR (400 MHz, d6-DMSO, 2 diastereomers): 8.08 (d, 0.5H), 8.02 (d, 0.5H), 5.81-5.68 (m, 1H), 5.02-4.88 (m, 2H), 4.42-4.38 (m, 1H), 3.62 (s, 1.5H), 3.61 (s, 1.5H), 2.99-2.89 (m, 1H), 2.19 (s, 1.5H), 2.18 (s, 1.5H), 2.11-1.89 (m, 3H), 1.75-1.61 (m, 1H), 1.58-1.12 (m, 4H), 1.10 (d, 1.5H), 1.08 (d, 1.5H), 0.88 (d, 1.5H), 0.84 (d, 1.5H)

h) [(S)-1-((R)-1-Cyano-3-methyl-hept-6-enylcarbamoyl)-ethyl]-methyl-carbamic acid tert-butyl ester To a solution of 5.01 g (24.64 mmol) BOC-N-methyl-(L)-alanine and 4.95 g (31.36 mmol) HOBt in 100 ml DCM at 0° C. is added 5.15 g (26.88 mmol) EDC.HCl, after 10 min followed by 3.41 g(22.4 mmol) (R)-2-Amino-4-methyl-oct-7-enenitrile. After stirring for 17 h at rt the mixture is cooled to 0° C., 224 ml 0.5 M HCl is added and the layers are separated. The aqueous phase is extracted with DCM/ethanol=80/20 twice, the combined organic layers are washed with 1 M potassium bicarbonate, water, dried with sodium sulfate and evaporated to yield the product as a yellowish oil (mixture of diastereomers), which is used in the next step without further purification.

Rf: (DCM/methanol=95/5): 0.66
MS (EI): [MNa]$^+$=360.4
$^1$H-NMR (400 MHz, d6-DMSO, 2 diastereomers): 8.58 (d, 0.5H), 8.51 (d, 0.5H), 5.82-5.71 (m, 1H), 5.04-4.91 (m, 2H), 4.79-4.71 (m, 1H), 4.55-4.45 (br m, 0.5H), 4.32-4.15 (br m, 0.5H), 2.78 (s, 1.5H), 2.75 (s, 1.5H), 2.12-1.94 (m, 2H), 1.91-1.79 (m, 1H), 1.65-1.14 (m, 5H), 1.39 (s, 9H), 1.25 (br d, 3H), 0.89 (d, 1.5H), 0.85 (m, 1.5H)

i) (R)-2-Amino-4-methyl-oct-7-enenitrile

A solution of 6.22 g (116.3 mmol) ammonium chloride and 5.58 g (85.7 mmol) sodium cyanide in 36.8 ml conc. aq. ammonium hydroxide and 20 ml methanol is cooled to 0° C. and ammonia is bubbled through for 10 min. A solution of 7.34 g (52.6 mmol) (R)-3-methyl-hept-6-enal in 50 ml methanol is added at 0° C. The mixture is stirred at rt for 2 days. Excess ammonia is evaporated, the mixture cooled to 0° C. and acidified by addition of 105 ml 0.5 M HCl. The mixture is washed with diethyl ether twice and the combined organic layers are backwashed with 105 ml 0.5 M HCl. The acidic aqueous layers are combined, the pH adjusted to 8 by addition of 6 M aq. ammonium hydroxide and extracted with DCM twice. The combined DCM layers are backwashed with water, dried with sodium sulfate and evaporated to yield the product as a brownish oil (mixture of diastereomers), which is used for the next step without further purification.

Rf: (DCM/methanol=98/2): 0.29
MS (EI): [MH]$^+$=153.1
1H-NMR (400 MHz, d6-DMSO): 5.84-5.70 (m, 1H), 4.98 (d, 1H), 4.90 (d, 1H), 5.67 (br d, 1H), 2.24 (br s, 2H), 2.12-1.90 (m, 2H), 1.70-1.53 (m, 2H), 1.48-1.32 (m, 2H), 1.27-1.12 (m, 2H), 0.91-0.83 (m, 3H)

j) (R)-3-Methyl-hept-6-enal

To a solution of 9.06 g (52.6 mmol) (R-7,7-dimethoxy-5-methyl-hept-1-ene) in 50 ml chloroform is added 26.3 ml TFA/water (1:1) at 0° C., and the mixture is stirred at 8° C. for 17 h. The reaction mixture is cooled to 0° C. again and the pH adjusted to ca. 8.5 by addition of 15.5 g (184 mmol) sodium bicarbonate. After addition of water the mixture is extracted with DCM twice. The combined organic extracts are washed with water, dried with sodium sulfate and evaporated. The product is obtained as a volatile pale yellow oil and used for the next step without further purification.

$^1$H-NMR (400 MHz, CDCl$_3$): 9.77 (t, 1H), 5.88-5.73 (m, 1H), 5.09-4.93 (m, 2H), 2.44 (dd, 1H), 2.30-2.22 (m, 1H), 2.19-2.01 (m, 3H), 1.52-1.29 (m, 2H), 0.99 (d, 3H)

k) (R)-7,7-Dimethoxy-5-methyl-hept-1-ene

To a suspension of 1.96 g (5.5 mmol) methyltriphenylphosphonium bromide in 5 ml THF is added 617 mg (5.5 mmol) potassium tert-butoxide at 0° C. The mixture is stirred for 15 min at rt, then cooled to 0° C. and a solution of 1.59 g (5 mmol) (R)-6,6-dimethoxy-4-methyl-hexanal in 2.5 ml THF is added dropwise. After stirring for 2 h at rt the reaction mixture is poured onto 15 ml ice-water and extracted with diethyl ether. The combined organic extracts are dried with sodium sulfate and the solvent is evaporated. The residue is taken up in 10 ml hexane and stirred for 30 min. The precipitated triphenylphosphine oxide is filtered off and the filtrate is directly poured onto a chromatography column. Purification by chromatography on silica gel (n-hexane/diethyl ether 95/5) gives the product as a colorless oil.

Rf: (n-hexane/diethyl ether=70/30): 0.36

$^1$H-NMR (400 MHz, CDCl$_3$): 5.74-5.60 (m, 1H), 4.89 (d, 1H), 4.82 (d, 1H), 4.35 (t, 1H), 3.20 (1, 3H), 3.18 (s, 3H), 2.05-1.85 (m, 2H), 1.58-1.41 (m, 2H), 1.36-1.21 (m, 2H), 1.19-1.05 (m, 1H), 0.79 (d, 3H)

l) (R)-6,6-Dimethoxy-4-methyl-hexanal

A mixture of 17.7 g (88.2 mmol) (R)-8,8-dimethoxy-2,6-dimethyl-oct-2-ene and 3.7 g (44.1 mmol) sodium bicarbonate in 265 ml DCM/methanol (4:1) is cooled to −78° C. and ozone is bubbled through the mixture. After 1 h 20 min the pale yellow solution turns pale blue and 34.8 g (132 mmol) triphenylphosphine is added at −78° C. The mixture is warmed to rt and stirred for 30 min. The solvent is evaporated and the residue taken up in 176 ml hexane and stirred for 30 min. The precipitated triphenylphosphine oxide is removed by filtration and the solvent evaporated. The product is obtained as a pale yellow oil and used for the next step without further purification.

Rf: (n-hexane/diethyl ether=70/30): 0.24 m) (R)-8,8-Dimethoxy-2,6-dimethyl-oct-2-ene

A solution of 18.39 g (119.2 mmol) (R)-3,7-dimethyl-oct-6-enal (R-citronellal), 30.1 ml (275 mmol) trimethyl orthoformate, 315 mg (3.93 mmol) ammonium nitrate and 180 mg (0.715 mmol) PPTS in 60 ml methanol is stirred at rt for 17 h. The mixture is poured on 300 ml saturated aqueous sodium bicarbonate and extracted with diethyl ether twice. The combined organic extracts are dried with sodium sulfate and the solvent is evaporated. The product is obtained as a pale yellow oil and used for the next step without further purification.

Rf: (n-hexane/diethyl ether=90/10): 0.36

$^1$H-NMR (400 MHz, CDCl$_3$): 5.11 (t, 1H), 4.48 (t, 1H), 3.30 (s, 3H), 3.33 (s, 3H), 2.08-1.92 (m, 2H), 1.70 (s, 3H), 1.69-1.55 (m, 2H), 1.60 (s, 3H), 1.43-1.31 (m, 2H), 1.14-1.27 (m, 1H), 0.93 (d, 3H)

The following compounds can be obtained by a similar procedure, using 3-methoxy-benzylamine, 2-pyridin-4-yl-ethylamine, 2-(3,4-dimethoxy-phenyl)-ethylamine or 3-isopropyl-benzylamine instead of 3-methyl-benzylamine:

Example 1a (3S,14R)-16-[1-Hydroxy-2-(3-methoxy-benzylamino)-ethyl]-3,4,14-trimethyl-1,4-diaza-cyclohexadecane-2,5-dione Mixture of Diastereomers Rf: (DCM/methanol 95:5): 0.33
MS (LC/MS): [MH]$^+$=476.0

Example 1b (3S,14R)-16-[1-Hydroxy-2-(2-pyridin-4-yl-ethylamino)-ethyl]-3,4,14-trimethyl-1,4-diaza-cyclohexadecane-2,5-dione Mixture of Diastereomers Rf: (DCM/methanol/NH$_3$=90:10:1): 0.25
MS (LC/MS): [MH]$^+$=461.0

Example 1c (3S,14R)-16-{2-[2-(3,4-Dimethoxy-phenyl)-ethylamino]-1-hydroxy-ethyl}-3,4,14-trimethyl-1,4-diaza-cyclohexadecane-2,5-dione Mixture of Diastereomers Rf: (DCM/methanol/NH$_3$ 90:9:1): 0.30
MS (LC/MS): [MH]$^+$=520.0

Example 1d (3S,14R)-16-[1-Hydroxy-2-(3-methyl-benzylamino)-ethyl]-3,14-dimethyl-1,4-diaza-cyclohexadecane-2,5-dione The title compound is prepared similarly to Example 1, using Boc-N-(L)alanine instead of Boc-N-methyl-(L)-alanine in step h.

Mixture of Diastereomers

LC (Atlantis dC-18, 19×100 mm, 5 μM, 10% MeCN+10% H$_2$O (2 min) 10-100% MeCN+10% H$_2$O (12 min), 100% MeCN+10% H$_2$O (3 min) 20 ml/min): 11.1 min
MS (LC/MS): [MH]$^+$=446.3

Example 1e (3S,14R)-16-[1-Hydroxy-2-(3-methoxy-benzylamino)-ethyl]-3,14-dimethyl-1,4-diaza-cyclohexadecane-2,5-dione Mixture of Diastereomers LC (Atlantis dC-18, 19×100 mm, 5 μM, 10% MeCN+10% H$_2$O (2 min) 10-100% MeCN+10% H$_2$O (12 min), 100% MeCN+10% H$_2$O (3 min) 20 ml/min): 3.8 min
MS (LC/MS): [MH]$^+$=462.3

Example 1f (3S,14R)-16-[1-Hydroxy-2-(3-isopropyl-benzylamino)-ethyl]-3,14-dimethyl-1,4-diaza-cyclohexadecane-2,5-dione Mixture of Diastereomers LC (Atlantis dC-18, 19×100 mm, 5 μM, 10% MeCN+10% H$_2$O (2 min) 10-100% MeCN+10% H$_2$O (12 min), 100% MeCN+10% H$_2$O (3 min) 20 ml/min): 11.9 min
MS (LC/MS): [MH]$^+$=474.4

Example 1g (3S,14R)-16-[1-Hydroxy-2-(2-pyridin-4-yl-ethylamino)-ethyl]-3,14-dimethyl-1,4-diaza-cyclohexadecane-2,5-dione Mixture of Diastereomers
LC (Atlantis dC-18, 19×100 mm, 5 μM, 10% MeCN+10% H$_2$O (2 min) 10-100% MeCN+10% H$_2$O (12 min), 100% MeCN+10% H$_2$O (3 min) 20 ml/min): 10.7 min
MS (LC/MS): [MH]$^+$=447.3

Example 2

(3S,14R,16S)-16-[(1R)-1-Hydroxy-2-(3-isopropyl-benzylamino)-ethyl]-3,4,14-trimethyl-1,4-diaza-cyclohexadecane-2,5-dione The title compound can be prepared similarly to Example 1, using the pure diastereomer (3S,14R,16S)-16-((S-2-chloro-1-hydroxy-ethyl)-3,4,14-trimethyl-1,4-diaza-cyclohexadecane-2,5-dione instead of the diastereomeric mixture (3S,14R)-16-(2-chloro-1-hydroxy-ethyl)-3,4,14-trimethyl-1,4-diaza-cyclohexadecane-2,5-dione in step b, and in the last step 3-isopropyl-benzylamine instead of 3-methyl-benzylamine with a modified work-up procedure: A solution of 34 mg (0.1 mmol) 3(S),4,14(R)-trimethyl-16(S)-(S)oxiranyl-1,4-diaza-cyclohexadecane-2,5-dione in 57 mg (0.38 mmol) 3-isopropyl-benzylamine is heated to 80° C. for 8 h. Excess 3-isopropyl-benzylamine is removed by repeated co-evaporation with toluene. Purification of the residue by preparative thin layer chromatography or HPLC gives a thick colorless oil.
Rf: (DCM/methanol/14N NH$_3$=90/9/1): 0.5
MS (EI): [MH]$^+$=488
1H-NMR (400 MHz, d6-DMSO, major conformer): 8.90 (br s, 1H), 7.67 (d, 1H), 7.42-7.25 (m, 4H), 5.58 (br s, 1H), 4.92 (q, 1H), 4.10 (br t, 2H), 3.78-3.69 (m, 1H), 3.64-3.52 (m, 1H), 2.94-2.84 (m, 2H), 2.81 (s, 3H), 2.75-2.63 (m, 1H), 2.11-2.02 (m, 1H), 1.70-1.59 (m, 1H), 1.45-1.11 (m, 23H), 1.04 (d, 3H), 0.74 (d, 3H)

The starting material can be prepared as described hereafter:

a) Hept-6-enoic acid {(S)-1-[(1S,3R)-1-((S)-2-chloro-1-hydroxy-ethyl)-3-methyl-hept-6-enylcarbamoyl]-ethyl}-methyl-amide To an ice-cold solution of 141 mg (1.1 mmol) hept-6-enoic acid, 221 mg (1.1 mmol) HOBt.H$_2$O, 230 mg (1.2 mmol) EDC.HCl and 327 mg (1.0 mmol) {1(S)-[1(S)-(2-chloro-1(S)-hydroxy-ethyl)-3(R)-methyl-hept-6-enylcarbamoyl]-ethyl} methyl amino hydrochloride in 12 ml DCM are added 0.172 ml (1.0 mmol) DIPEA. The mixture is stirred at rt for 17 h. After cooling with ice 10 ml of 0.5 M HCl are added and the layers are separated. The organic layer is washed with 1 M potassium bicarbonate, water, dried with sodium sulfate and evaporated. The residue is purified by chromatography on silica gel (cyclohexane/EtOAc 70/30) and gives the product as yellow solid.
Rf: (cyclohexane/EtOAc=60/40): 0.24
MS (EI−): 399 [MH]$^−$
1H-NMR (400 MHz, d6DMSO, major rotamer): 7.31 (d, 1H), 5.85-5.70 (m, 2H), 5.28 (d, 1H), 5.04-4.78 (m, 5H), 3.88-3.73 (m, 1H), 3.63-3.46 (m, 2H), 3.43-3.34 (m, 1H), 2.82 (s, 3H), 2.31 (t, 2H), 2.07-1.93 (m, 4H), 1.57-1.12 (m, 9H), 1.18 (d, 3H), 0.79 (d, 3H)

b) {1(S)-[1(S)-(2-Chloro-1(S)-hydroxy-ethyl)-3(R)-methyl-hept-6-enylcarbamoyl]-ethyl}-methyl amino hydrochloride A solution of 814 mg (2.08 mmol) {1(S)-[1(S)(2-chloro-1(S)-hydroxy-ethyl)-3(R)-methyl-hept-6-enylcarbamoyl]-ethyl}-methyl-carbamic acid tert-butyl ester in 4 ml DCM is cooled to 0° C. and 6.3 ml 5 M HCl in Et$_2$O (31.3 mmol) are added. The mixture is stirred at rt for 1.5 h. The solvent is evaporated to yield the product as pale brownish powder, which is used for the next step without further purification.
Rf: (cyclohexane/EtOAc=60/40): 0.0
MS (EI+): 291 [MH]+
$^1$H-NMR (400 MHz, d6-DMSO): 8.97 (br, 1H), 8.78 (br, 1H), 8.35 (d, 1H), 5.83-5.71 (m, 1H), 5.47 (d, 1H), 5.03-4.88 (m, 2H), 3.98-3.86 (m, 1H), 3.79-3.69 (m, 1H), 3.62-3.53 (m, 2H), 3.51-3.43 (m, 1H), 2.46 (s, 3H), 2.10-1.95 (m, 2H), 1.56-1.17 (m, 5H), 1.38 (d, 3H), 0.85 (d, 3H)

c) {1(S)-[1(S)-(2-Chloro-1(S)-hydroxy-ethyl)-3(R)-methyl-hept-6-enylcarbamoyl]-ethyl}-methyl-carbamic acid tert-butyl ester To an ice-cold solution of 519 mg (2.55 mmol) Boc-N-methyl-(L)-alanine, 513 mg (3.25 mmol) HOBt.H$_2$O, 534 mg (2.78 mmol) EDC.HCl and 566 mg (2.32 mmol) 1(S)(2-chloro-1(S)-hydroxy-ethyl)-3(R)-methyl-hept-6-enyl hydrochloride in 12 ml DCM is added 0.399 ml (2.32 mmol) DIPEA. The mixture is stirred at rt for 17 h. After cooling with an ice bath 23 ml of 0.5 M HCl are added and the layers are separated. The organic layer is washed with 1 M potassium bicarbonate, water, dried with sodium sulfate and evaporated. The residue is purified by chromatography on silica gel (cyclohexane/EtOAc 70/30) and gives the product as yellow oil.
Rf: (cyclohexane/EtOAc=60/40): 0.39
MS (EI−): 389 [MH]$^−$
1H-NMR (400 MHz, d6-DMSO): 7.43 (br, 1H), 5.82-5.71 (m, 1H), 5.30 (d, 1H), 5.01-4.87 (m, 2H), 4.44 (br, 1H), 3.83-3.74 (m, 1H), 3.51-3.46 (m, 2H), 3.41-3.35 (m, 1H), 2.72 (s, 3H), 2.09-1.93 (m, 1H), 1.50-1.13 (m, 9H), 1.39 (s, 9H), 0.79 (d, 3H)

d) 1(S)-(2-Chloro-1(S)-hydroxy-ethyl)-3(R)-methyl-hept-6-enyl amino hydrochloride A solution of 709 mg (2.32 mmol) [1 (S)-(2-Chloro-1(S)-hydroxy-ethyl)-3(R)-methyl-hept-6-enyl]-carbamic acid tert-butyl ester in 5 ml DCM is cooled to 0° C. and 7.0 ml 5 M HCl in Et$_2$O (35 mmol) are added. The mixture is stirred at rt for 1.5 h. The solvent is evaporated to yield the product as pale brownish powder, which is used for the next step without further purification.
Rf: (cyclohexane/EtOAc=80/20): 0.0
MS (LC/MS): 205.9 [MH]+ e) [1(S)-(2-Chloro-1(S)-hydroxy-ethyl)-3(R)-methyl-hept-6-enyl]-carbamic acid tert-butyl ester A solution of 224 mg (5.91 mmol) sodium borohydride in 65 ml ethanol is cooled to −78° C., a solution of 1.41 g (2.96 mmol) [1(S)-(2-chloro-acetyl)-3(R)-methyl-hept-6-enyl]-carbamic acid tert-butyl ester in 18 ml ethanol is added dropwise, maintaining the internal temperature below −75° C. The mixture is allowed to warm to rt and stirred for 17 h. The mixture is cooled to −78° C. and 14.8 ml of 1 M HCl are added dropwise. Ethanol is evaporated and the residue is taken up in 1 M HCl and EtOAc, the layers are separated and the aqueous layer is extracted with EtOAc, the combined organic layers are dried with sodium sulfate and evaporated. The residue is purified by chromatography on silica gel (cyclohexane/EtOAc 80/20) and gives the product as pale brown amorphous solid.

Rf: (cyclohexane/EtOAc=80/20): 0.25
MS (EI−): 304 [MH]−
1H-NMR (400 MHz, d6-DMSO): 6.57 (d, 1H), 5.82-5.71 (m, 1H), 5.21 (d, 1H), 5.02-4.87 (m, 2H), 3.58 (d, 1H), 3.50-3.38 (m, 3H), 2.06-1.92 (m, 2H), 1.53-1.15 (m, 5H), 1.38 (s, 9H), 0.82 (d, 3H)

f) [1(S)-(2-Chloro-acetyl)-3(R)-methyl-hept-6-enyl]-carbamic acid tert-butyl ester A solution of 844 mg (2.96 mmol) 2(S)-tert-butoxycarbonylamino-4(R)-methyl-oct-7-enoic acid methyl ester in 30 ml THF is cooled at −78° C. and 0.86 ml (11.8 mmol) chloroiodo-methane are added. A 1.59 M THF solution of LDA (9.3 ml, 14.8 mmol) is added dropwise while the temperature of the reaction mixture is maintained below −75° C., and the mixture is stirred for an additional 1 h. The reaction is carefully quenched with 4.41 ml (76.89 mmol) glacial acetic acid while the temperature is maintained below −65° C. After stirring for 15 min at −78° C. the mixture is allowed to warm to 0° C. and 44 ml of a half-saturated aqueous sodium chloride solution is added. The mixture is extracted with TBME, the organic layer washed with 1 M sodium bicarbonate and 1 M sodium sulfite, dried with sodium sulfate and evaporated. The product is used for the next step without further purification.

Rf: (cyclohexane/EtOAc=80/20): 0.44
MS (LC/MS): [MNa]+=325.9 g) 2(S)-tert-Butoxycarbonylamino-4(R)-methyl-oct-7-enoic acid methyl ester

To an ice-cooled solution of 1.15 g (4.25 mmol) 2(S)-tert-butoxycarbonylamino-4(R)-methyl-oct-7-enoic acid in 5 ml DMF is added 850 mg (8.49 mmol) potassium bicarbonate and 0.422 ml (6.79 mmol) MeI. The mixture is stirred at rt for 2 days. Toluene and water are added to the mixture, the layers are separated and the aqueous layer is extracted with toluene/isopropanol (85/15) twice. The combined organic layers are washed with half-saturated aqueous sodium chloride, dried with sodium sulfate and evaporated. The residue is purified by chromatography on silica gel (cyclohexane/EtOAc 90/10) and gives the product as colorless oil.

Rf: (cyclohexane/EtOAc=80/20): 0.39
$[\alpha]_D^{25}$ +3.06° (c=1.09, CHCl$_3$)
MS (EI): [MH]+=286, [MNa]+=308
1H-NMR (400 MHz, d6-DMSO): 7.19 (d, 1H), 5.82-5.70 (m, 1H), 5.03-4.89 (m, 2H), 4.04-3.95 (m, 1H), 3.60 (s, 3H), 2.10-1.90 (m, 2H), 1.68-1.44 (m, 2H), 1.42-1.27 (m, 2H), 1.38 (s, 9H), 1.25-1.15 (m, 1H), 0.83 (d, 3H)

h) 2(S)-tert-Butoxycarbonylamino-4(R)-methyl-oct-7-enoic acid

A solution of 11.3 g lyophilized 2(S)amino-4(R)methyl-oct-7-enoic acid (includes phosphate salts) in 113 ml water and 23 ml THF is cooled to 0° C. and 1.04 g (9.825 mmol) sodium car and 1.61 g (7.369 mmol) Boc$_2$O are added. The mixture is allowed to warm to rt and stirred for 19 h. After cooling with an ice bath the mixture is acidified by the addition of 162 ml 0.5 M HCl. The mixture is extracted with EtOAc twice, the combined EtOAc layers are washed with half-saturated aqueous sodium chloride, dried with sodium sulfate and evaporated to yield the product as pinkish oil, which is used for the next step without further purification.

Rf: (DCM/methanol=95/5): 0.26
MS (LC/MS): [MH]−=270.1 i) 2(S)-Amino-4(R)-methyl-oct-7-enoic acid

The pH of the remaining aqueous phase is re-adjusted to pH 8, and CoCl$_3$×6H$_2$O (5 mg, 0.021 mmol) and 125 mg acylase Amano (ACV12502) are added. The mixture is stirred at room temperature for 24 h. TLC indicates complete conversion. The mixture is lyophilized and the solid residue used for the next step without further purification. Analytical data obtained from analytical samples:

Rf: (acetonitrile/ethanol/water/acetic acid)=70/20/5/5): 0.41
$[\alpha]_D^{20}$ +2.05° (c=0.95, 1 M HCl)
MS (EI): [MH]+=172 j) 2(S)-Acetylamino-4(R)-methyl-oct-7-enoic acid

To 11.26 g (49.54 mmol) (R)-2-Acetylamino-4-methyl-oct-7-enoic acid methyl ester in 75 ml (33 mM) phosphate buffer pH 7.5 are added 200 μd of Alcalase 2,5 L (Novo Nordisk PMN04666). Under continuous stirring at room temperature the pH of the mixture is kept constant by adding 1M sodium hydroxide solution from an auto burette. After 3 hours, the conversion reaches about 50%. The pH is adjusted to 8.0 and the mixture extracted with DCM (3×50 ml). The organic phase is dried with magnesium sulfate and the solvent removed under reduced pressure yielding the un-desired diastereomeric methyl ester. The acid remaining in the aqueous solution is used in the next step without further purification. Analytical data are obtained from analytical samples:

Acid:
Rf: (acetonitrile/ethanol/water/acetic acid)=70/20/5/5): 0.68
$[\alpha]_D^{20}$: −5.19° (c=0.924, methanol)
MS (EI): [MH]+=214
1H-NMR (400 MHz, d6-DMSO): 8.25 (d, 1H), 6.05-5.93 (m, 1H), 5.25-5.10 (m, 2H), 4.47-4.39 (m, 1H), 2.33-2.14 (m, 2H), 2.04 (s, 3H), 1.85-1.76 (m, 1H), 1.75-1.50 (m, 3H), 1.47-1.37 (m, 1H), 1.03 (d, 3H)

Methyl Ester
LC (Chiralpak AD-H, 250×4.6 mm, hexane/ethanol 95/5, 1 ml/min): 9.01 min
1H-NMR (400 MHz, d6-DMSO): 8.20 (d, 1H), 5.65-5.75 (m, 1H), 4.95 (m, 1H), 4.90 (m, 1H), 4.20 (m, 1H), 3.55 (s, 3H), 1.75 (s, 3H), 1.8-2.0 (m, 1H), 1.55 (m, 1H), 1.30-1.45 (m, 3H), 1.00-1.10 (m, 1H), 0.8 (d, 3H)

k) (R)-2-Acetylamino-4-methyl-oct-7-enoic acid methyl ester

A solution of 4.92 g (25.0 mmol) N-((R)-1-cyano-3-methyl-hept-6-enyl)-acetamide in 75 ml methanol is cooled to 0° C., 150 ml 5 M HCl in Et$_2$O are added and the mixture is stirred at rt for 1 h. After cooling with ice 350 ml water is added and the mixture is extracted three times with DCM. The combined organic layers are washed with 1 M potassium bicarbonate and water, dried with sodium sulfate and evaporated. The residue is purified by chromatography on silica gel (cyclohexane/EtOAc 70/30 to 60/40) and gives the product as yellowish oil (mixture of diastereomers).

Rf: (cyclohexane/EtOAc=60/40): 0.16
MS (EI): [MH]$^+$=228
$^1$H-NMR (400 MHz, d6DMSO, 2 diastereomers): 8.21 (d, 0.5H), 8.18 (d, 0.5H), 5.82-5.68 (m, 1H), 5.03-4.89 (m, 2H), 4.32-4.22 (m, 1H), 3.60 (s, 3H), 2.10-1.89 (m, 2H), 1.84 (s, 1.5H), 1.83 (s, 1.5H), 1.67-1.58 (m, 1H), 1.53-1.08 (m, 4H), 0.88 (d, 1.5H), 0.82 (d, 1.5H)

l) N-((R)-1-Cyano-3-methyl-hept-6-enyl)-acetamide

To a solution of 3.81 g (25.0 mmol) (R)-2-amino-4-methyl-oct-7-enenitrile (step i, example 1) and 6.45 ml (37.5 mmol) DIPEA in 50 ml DCM at 0° C. are added dropwise 2.31 ml (32.5 mmol) acetyl chloride. The mixture is stirred at rt for 1 h. Upon cooling with ice the mixture is quenched with a half-saturated aqueous solution of ammonium chloride. The mixture is extracted with DCM, the extract washed with water, dried with sodium sulfate and evaporated to yield the product as brownish oil (mixture of diastereomers), which is used for the next step without further purification.

Rf: (DCM/methanol=98/2): 0.21
MS (LC/MS): [MH]$^+$=195.0

The following compounds can be obtained by a similar procedure, using 3-cyclopropyl-benzylamine, C-(5-bromo-pyridine-3-yl)methylamine, C-(5-cyclopropyl-pyridine-3-yl)-methylamine, C-(2-cyclopropyl-pyridine-4-yl)-methylamine, 6 isopropyl-2,2-dimethyl-chroman-4(R/S)-ylamine, 3-tert-butyl-benzylamine or 3-(2,2-dimethyl-propyl)-benzylamine instead of 3-isopropyl-benzylamine:

Example 2a (3S,14R,16S)-16-[(1R)-2-(3-Cyclopropyl-benzylamino)-1-hydroxy-ethyl]-3,4,14-trimethyl-1,4-diaza-cyclohexadecane-2,5-dione Rf (toluene/ethanol/NH3=90/9.9/0.1): 0.24
MS (EI):[MH]$^+$=486

Example 2b (3S,14R,16S)-16-{(1R)-2-[(5-Bromo-pyridin-3-ylmethyl)-amino]-1-hydroxy-ethyl}-3,4,14-trimethyl-1,4-diaza-cyclohexadecane-2,5-dione Rf (DCM/methanol/NH3=90/9/1): 0.40
MS (EI): [MH]$^+$=527

Example 2c (3S,14R,16S)-16-{(1R)-2-[(5-Cyclopropyl-pyridin-3-ylmethyl)-amino]-1-hydroxy-ethyl}-3,4,14-trimethyl-1,4-diaza-cyclohexadecane-2,5-dione Rf (toluene/ethanol/NH3=90/9.9/0.1): 0.16
MS (EI): [MH]$^+$=487

Example 2d (3S,14R,16S)-16-{(1R)-2-[(2-Cyclopropyl-pyridin-4-ylmethyl)-amino]-1-hydroxy-ethyl}-3,4,14-trimethyl-1,4-diaza-cyclohexadecane-2,5-dione Rf (DCM/methanol=90/10): 0.34
MS (EI): [MH]$^+$=487

Example 2e (3S,14R,16S)-16-[(1R)-2-(2,2-Dimethyl-6-isopropyl-chroman-4-ylamino)-1-hydroxy-ethyl]-3,4,14-trimethyl-1,4-diaza-cyclohexadecane-2,5-dione Rf (DCM/methanol/NH3=97/2.7/0.3): 0.17
MS (EI): [MH]$^+$=558

Example 2f (3S,14R,16S)-16-[(1R)-2-(3-tert-Butyl-benzylamino)-1-hydroxy-ethyl]-3,4,14-trimethyl-1,4-diaza-cyclohexadecane-2,5-dione Rf (DCM/methanol=90/10): 0.37
MS (EI): [MH]$^+$=502

Example 2g (3S,14R,16S)-16-{(1R)-2-[3-(2,2-Dimethyl-propyl)-benzylamino]-1-hydroxy-ethyl}-3,4,14-trimethyl-1,4-diaza-cyclohexadecane-2,5-dione Rf: (DCM/methanol=90/10): 0.41
MS (EI): [MH]$^+$=516.5

Example 2h (3S,15R,17S)-17-[(1R)-1-Hydroxy-2-(3-isopropyl-benzylamino)-ethyl]-3,4,15-trimethyl-1,4-diaza-cycloheptadecane-2,5-dione The title compound can be prepared similarly to Example 2, using oct-7-enoic acid in step a instead of hept-6-enoic acid.

Rf: (DCM/methanol=90/10): 0.34
MS (EI): [MH]$^+$=502

Example 2i (6S,9S,11R)-9-[(1R)-1-Hydroxy-2-(3-isopropyl-benzylamino)-ethyl]-5,6,11-trimethyl-1oxa-5,8-diaza-cyclohexadecane-4,7-dione The title compound can be prepared similarly to Example 2, using 3-allyloxy-propionic acid in step a instead of hept-6-enoic acid.

Rf (DCM/methanol/NH3=90/9/1): 0.46
MS (EI): [MH]$^+$=490

Example 2j (3S,8S,14R,16S)-16-[(1R)-1-Hydroxy-2-(3-isopropyl-benzylamino)-ethyl]-3,4,8,14-tetramethyl-1,4-diaza-cyclohexadecane-2,5-dione The title compound can be prepared similarly to Example 2, using 4-(R)-methyl-hept-6-enoic acid (Acid Ib) in step a instead of hept-6-enoic acid.
Rf: (DCM/methanol=90/10): 0.43
MS (EI): [MH]$^+$=502.5

Example 3

(3S,6S,8R)-6-[(1R)-1-Hydroxy-2-(3-isopropyl-benzylamino)-ethyl]-3,8-dimethyl-1,1-dioxo-1lambda*6*-thia-5-aza-cyclohexadecan-4-one The title compound can be prepared similarly to Example 2, using (S)-3-(hex-5-ene-1-sulfonyl)-2-methyl-propionic acid (Acid IIa) in step c instead of BOC-N-methyl-(L)-alanine, followed by the usual procedure for ring-closing metathesis and thereafter.
Rf: (DCM/methanol/14N NH$_3$=90/9/1): 0.45
MS (EI): [MH]$^+$=509

The following compound can be obtained by a similar procedure, using instead of 3-(hex-5-ene-1-sulfonyl)-2(S)-methyl-propionic acid in Example 3 2(S)-methyl-3-(pent-4-ene-1-sulfonyl)-propionic acid (Acid IIb):

Example 3a (3S,6S,8R)-6-[(1R)-1-Hydroxy-2-(3-isopropyl-benzylamino)-ethyl]-3,8-dimethyl-1,1-dioxo-1lambda*6*-thia-5-aza-cyclopentadecan-4-one Rf: (DCM/methanol/Et$_3$N=94/5/1): 0.90
MS (LC-MS): [MH]$^+$=495; [MNa]$^+$=517

Example 4

(4S,6R)-12-Ethyl [(1R)-1-hydroxy-2-(3-isopropyl-benzylamino)-ethyl]-6-methyl-3,12-diaza-bicyclo[12.3.1]octadeca-1(17),14(18),15-triene-2,13-dione The title compound can be prepared similarly to Example 2, using N-allyl-N-ethyl-isophthalamic acid (Acid IIIa) in step c instead of BOC-N-methyl-(L)-alanine, followed by the usual procedure for ring-closing metathesis and thereafter.
Rf: (DCM/methanol=5/1): 0.56
MS (LC-MS): [MH]$^+$=508; [MNa]$^+$=530

Example 5

(9R,11S)-11-[(1R)-1-Hydroxy-2-(3-isopropyl-benzylamino)-ethyl]-9,16-dimethyl-2,12,17-triaza-bicyclo[12.3.1]octadeca-1(18),14,16-trien-13-one The title compound can be prepared similarly to Example 2, using 2-but-3-enylamino-6-methyl-isonicotinic acid (Acid IIIa) in step c instead of Boc-N-methyl-(L)-alanine, followed by the usual procedure for ring-closing metathesis and thereafter.
Rf: (DCM/methanol=5/1): 0.4
MS (LC-MS): [MH]$^+$=481
$^1$H-NMR (400 MHz, D$_3$COD): 7.30-7.17 (m, 5H), 6.60 (s, 1H), 6.49 (s, 1H), 3.95-3.90 (m, 1H), 3.84 (d, 1H), 3.78 (d, 1H), 3.66-3.61 (m, 1H), 3.35-3.20 (m, 2H), 2.98-2.87 (m, 1H), 2.80-2.70 (m, 2H), 2.38 (s, 3H), 1.80-1.64 (m, 3H), 1.60-1.20 (m, 10H), 1.26 (s, 3H), 1.28 (s, 3H), 0.98 (d, 3H)

Example 6

[(3S,6S,14R,16S)-16-((1S,3R)-3-Butylcarbamoyl-1-hydroxy-butyl)-3,14-dimethyl-2,5-dioxo-1,4-diaza-cyclohexadec-6-yl]-carbamic acid tert-butyl ester A solution of 199 mg (0.35 mmol) [(3S,6S,14R,16S)-16-((1S,3R)-3-butylcarbamoyl-1-hydroxy-butyl)-3,14-dimethyl-2,5-dioxo-1,4-diaza-cyclohexadec-10-en-6-yl]-carbamic acid tert-butyl ester in 10 ml THF and 10 ml EtOH is stirred in the presence of 20 mg 10% Pd-C under an hydrogen atmosphere for 1 h. The mixture is filtered over a pad of celite and the solvent evaporated. This yields the title compound as a white powder.
LC/MS (Nucleosil C-18HD, 4×70 mm, 3 μM, 20-100% MeCN (6 min), 100% MeCN (1.5 min)): 5.28 min; MS(ES) [MNa]$^+$=591.4

The starting material can be prepared as described hereafter:

a) [(3S,6S,14R,16S)-16-((1S,3R)-3-Butylcarbamoyl-1-hydroxy-butyl)-3,14-dimethyl-2,5-dioxo-1,4diaza-cyclohexadec-10-en-6-yl]-carbamic acid tert-butyl ester A solution of 183 mg (0.37 mmol) [(3S,6S,14R,16S)-3,14-dimethyl-16-((2S,4R)-4-methyl-5-oxo-tetrahydro-furan-2-yl)-2,5-dioxo-1,4diaza-cyclohexadec-10-en-6-yl]-carbamic acid tert-butyl ester in 1.5 ml butylamine is heated to 65° C. under nitrogen for two hours. The reaction mixture is evaporated, the residue taken up in toluene and evaporated to dryness to yield the title compound.
LC/MS (Nucleosil C-18HD, 4×70 mm, 3 μM, 20-100% MeCN (6 min), 100% MeCN (1.5 min)): 5.00 min; MS(ES) [MNa]$^+$=589.4 b) [(3S,6S,14R,16S)-3,14-Dimethyl-16-((2S,4R)-4-methyl-5-oxo-tetrahydro-furan-2-yl)-2,5-dioxo-1,4diaza-cyclohexadec-10-en-6-yl]-carbamic acid tert-butyl ester To a refluxing solution of 6 mg tricyclohexylphosphine [1,3-bis(2,4,6-trimethylphenyl)-4,5-dihydroimidazol-2-ylidene][benzylidine]ruthenium(IV)dichloride ('Grubbs 2' catalyst) in 300 ml DCM under a nitrogen atmosphere are slowly added 210 mg (0.402 mmol) ((S)-1-{(S)-1-[(1S,3R)-3-methyl-1-((2S,4R)-4-methyl-5-oxo-tetrahydro-furan-2-yl)hept-6-enylcarbamoyl]-ethylcarbamoyl}-hex-5-enyl)-carbamic acid tert-butyl ester in 50 ml degassed DCM. After 3 h the mixture is cooled to rt, quenched with 0.05 ml butyl vinyl ether, stirred with 200 mg activated charcoal and purified via chromatography on silica gel (EtOAc/hexane 1:1) to yield the product (mixture of double bond isomers).
LC/MS (Nucleosil C-18HD, 4×70 mm, 3 μM, 20-100% MeCN (6 min), 100% MeCN (1.5 min)): 5.19 min; MS(ES) [MNa]$^+$=516.4 c) ((S)-1-{(S)-1-[(1S,3R)-3-Methyl-1-((2S,4R)-4-methyl-5-oxo-tetrahydro-furan-2-yl)-hept-6-enylcarbamoyl]-ethylcarbamoyl}-hex-5-enyl)-carbamic acid tert-butyl ester A solution of 194 mg (0.489 mmol) of {(S)-1-[(1S,3R)-3-methyl-1-((2S,4R)-4-methyl-5-oxo-tetrahydro-furan-2-yl) hept-6-enylcarbamoyl]-ethyl}-carbamic acid tert-butyl ester in 2 ml 4N HCl in dioxane is kept 3 h at rt and then concentrated in vacuo. The residue is taken up in 3 ml DCM and treated with 187 mg (0.734 mmol) (2S)-tert-butoxycarbonyl-2-amino-6-heptenoic acid, 79 mg (0.516 mmol) HOBt.H$_2$O, 140 mg (0.734 mmol) EDC.HCl and 0.27 ml (1.95 mmol) Et$_3$N. After 18 h at rt the mixture is diluted with EtOAc and washed successively with water, 5% aqueous citric acid, water, 5% aqueous NaHCO$_3$ and water (4×). Evaporation of the mixture and chromatography on silica gel (EtOAc/hexane 1:2 and 1:1) gives the product.

LC/MS (Nucleosil C-18HD, 4×70 mm, 3 µM, 20-100% MeCN (6 min), 100% MeCN (1.5 min)): 5.94 min; MS(ES) [MNa]$^+$=544.4 d) {(S)-1-[(1S,3R)-3-Methyl-1-((2S,4R)-4-methyl-5-oxo-tetrahydro-furan-2-yl)-hept-6-enylcarbamoyl]-ethyl}-carbamic acid tert-butyl ester A solution of 1.0 g (3.08 mmol) of [(R)-3-methyl-1-(4-methyl-5-oxo-tetrahydro-furan-2-yl)-hept-6-enyl]-carbamic acid tert-butyl ester (mixture of diastereomers) in 6 ml 4N HCl in dioxane is kept 3 h at rt and concentrated in vacuo. The residue is taken up in 10 ml DCM and treated with 582 mg (3.08 mmol) Boc-Ala-OH, 499 mg (3.26 mmol) HOBt.H$_2$O, 882 mg (4.62 mmol) EDC.HCl and 1.72 ml (12.3 mmol) Et$_3$N and stirred overnight. The mixture is diluted with EtOAc and washed successively with water, 5% aqueous citric acid, water, 5% aqueous NaHCO$_3$ and water (4×). Evaporation of the mixture and chromatography on silica gel (EtOAc/hexane 1:7, 1:6 and 1:3) gives the faster eluting diastereomer and then {(S)-1-[(1S,3R)-3-methyl-1-((2S,4R-4-methyl-5-oxo-tetrahydro-furan-2-yl)-hept-6-enylcarbamoyl]-ethyl}-carbamic acid tert-butyl ester as a colorless oil.

LC/MS (Nucleosil C-18HD, 4×70 mm, 3 µM, 20-100% MeCN (6 min), 100% MeCN (1.5 min)): 5.29 min; MS(ES) MNa$^+$=419.4 e) [(R)-3-Methyl-1-(4-methyl-5-oxo-tetrahydro-furan-2-yl)-hept-6-enyl]-carbamic acid tert-butyl ester (mixture of diastereomers)

At −78° C. under nitrogen atmosphere a solution of 3.8 g (12.2 mmol) of [(R)-3-methyl-1-(5-oxo-tetrahydro-furan-2-yl)-hept-6-enyl]-carbamic acid tert-butyl ester (mixture of diastereomers) and 2.2 ml (18.3 mmol) DMPU in 50 ml THF are treated with 67.8 ml (25.6 mmol) of a 0.41 M solution of LHMDS in THF. After 50 min 1.30 ml (20.7 mmol) methyl iodide are added in one portion. Then after 45 min the reaction is quenched with 4.56 ml (61 mmol) propionic acid and the mixture is allowed to warm to rt and diluted with EtOAc and water. The organic phase is washed successively with 5% aqueous citric acid, water, 5% aqueous NaHCO3 and water (4×). Evaporation of the mixture and chromatography on silica gel (EtOAc/hexane 1:6) gives the product as a colorless oil that solidifies upon standing.

LC/MS (Nucleosil C-18HD, 4×70 mm, 3 µM, 20-100% MeCN (6 min), 100% MeCN (1.5 min)): 6.04 min; MS(ES) [MNa]$^+$=348.2 f) [(R)-3-Methyl-1-(5-oxo-tetrahydro-furan-2-yl)-hept-6-enyl]-carbamic acid tert-butyl ester (mixture of diastereomers)

A solution of 10.18 g (30 mmol) of [(R)-3,7-dimethyl-1-(5-oxo-tetrahydro-furan-2-yl)-oct-6-enyl]-carbamic acid tert-butyl ester (mixture of diastereomers) in 300 ml DCM and 100 ml MeOH is cooled to −75° C. After addition of 1.26 g (15 mmol) NaHCO$_3$ a stream of O$_3$ in O$_2$ is passed through the stirred mixture till a blue color persists. The excess ozone is removed by flushing with O$_2$. After addition of 9.44 g (36 mmol) triphenylphosphine the mixture is allowed to warm to rt and stirred for 4 h. The mixture is filtered and concentrated in vacuo. Chromatography on silica gel (EtOAc/Hexane 1:1) gives aldehyde contaminated with 20% triphenylphosphine oxide. A suspension of 11.8 g (33 mmol) methyl triphenylphosphonium bromide and 3.36 g (30 mmol) tBuOK in 150 ml toluene is stirred 1 h at rt, cooled with an ice bath and treated with a solution of the abovementioned aldehyde in 70 ml THF. After 30 min the mixture is quenched with saturated aqueous NaHCO$_3$. The organic phase is washed with brine, dried with sodium sulfate and evaporated. Column chromatography of the residue on silica gel (EtOAc/hexane 1:5) gives the product as a solidifying oil (mixture).

LC/MS (Nucleosil C-18HD, 4×70 mm, 3 µM, 20-100% MeCN (6 min), 100% MeCN (1.5 min)): 5.73 min; MS(ES) MNa$^+$=334.2 g) [(R)-3,7-Dimethyl-1-(5-oxo-tetrahydro-furan-2-yl)-oct-6-enyl]-carbamic acid tert-butyl ester (mixture of diastereomers)

A solution of 20.2 g (60 mmol) of [(R)-3,7-dimethyl-1-(5-oxo-2,5-dihydro-furan-2-yl)oct-6-enyl]-carbamic acid tert-butyl ester (mixture of diastereomers) in 200 ml THF is stirred under an atmosphere of hydrogen in the presence of 2 g Raney nickel. When the take-up of hydrogen has ceased the reaction mixture is filtered carefully (Raney nickel is pyrophoric!) via a pad of celite. Evaporation of the solvent gives the product as a colorless oil.

LC/MS (Nucleosil C-18HD, 4×70 mm, 3 µM, 20-100% MeCN (6 min), 100% MeCN (1.5 min)): 6.24 min; MS(ES) MNa$^+$=362 h) [(1S,3R)-3,7-Dimethyl-1-((S)-5-oxo-2,5-dihydro-furan-2-yl)-oct-6-enyl]-carbamic acid tert-butyl ester and [(1R,3R)-3,7-dimethyl-1-((R)-5-oxo-2,5-dihydro-furan-2-yl)-oct-6-enyl]-carbamic acid tert-butyl ester (mixture)

A solution of 20.67 g (128 mmol) HMDS in 200 ml dry THF is cooled at −70° C. and 80 ml of a 1.6 M solution of BuLi in hexane (128 mmol) are added dropwise. After 10 min a solution of 10.75 g (128 mmol) 5H-furan-2-one in 5 ml dry THF is added dropwise. After addition the mixture is warmed at −40° C. to prevent the formation of a precipitate and added via a canula to a stirred solution of 50.1 g (122 mmol) [(R)-3,7-dimethyl-1-(toluene-4-sulfonyl)-oct-6-enyl]-carbamic acid tert-butyl ester in 300 ml dry THF at −70° C. After stirring the mixture at this temperature for 1 h the mixture is poured directly into a stirred mixture of 500 ml water and 500 ml EtOAc. The organic phase is washed successively with 5% aqueous citric acid, water, 5% aqueous sodium bicarbonate and water (4×). The reaction mixture is evaporated and the residue chromatographed over silica gel (EtOAc/hexane 1:5) to yield a mixture of the products as a colorless oil that solidifies upon standing.

i) [(R)-3,7-Dimethyl-1-(toluene-4-sulfonyl)-oct-6-enyl]-carbamic acid tert-butyl ester A mixture of 21.34 g (131.4 mmol) R-(+)-Citronellal, 14.63 g (125 mmol) carbamic acid tert-butyl ester, 24.6 g (138 mmol) sodium 4-methyl-benzenesulfonate and 7.5 ml (200 mmol) formic acid in 100 ml acetonitrile are stirred at rt for 4 days. The mixture is diluted with 300 ml EtOAc and 300 ml water. The organic phase is successively washed with 5% aqueous citric acid, water, 5% aqueous sodium bicarbonate and four times with water. After addition of 5 ml EtOH the solution is concentrated in vacuo yielding the title compound as a colorless oil that solidifies upon standing.

LC/MS (Nucleosil C-18HD, 4×70 mm, 3 μM, 20-100% MeCN (6 min), 100% MeCN (1.5 min)): 6.85 min; MS(ES) [MNa]$^+$=432.2

The following compounds can be obtained by a similar procedure:

Example 6a (2R,4S)-N-Butyl-4-((2S,5S,7R)-2,7-dimethyl-3,15-dioxo-1,4-diaza-cyclopentadec-5-yl)-4-hydroxy-2-methyl-butyramide The compound can be prepared according to a similar procedure as example 6 except for using hex-5-enoic acid instead of (2S)tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 4.32 min; MS(ES) [MNa]$^+$=462.4

Example 6b (2R,4S)-N-Butyl-4-((2S,5S,7R)-2,7-dimethyl-3,16-dioxo-1,4-diaza-cyclohexadec-5-yl)-4-hydroxy-2-methyl-butyramide The compound can be prepared according to a similar procedure as example 6 except for using hept-6-enoic acid instead of (2S)tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 4.68 min; MS(ES) [MNa]$^+$=476.4

Example 6c (2R,4S)-N-Butyl-4-((2S,5S,7R)-2,7-dimethyl-3,17-dioxo-1,4-diaza-cycloheptadec-5-yl)-4-hydroxy-2-methyl-butyramide The compound can be prepared according to a similar procedure as example 6 except for using oct-7-enoic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 5.05 min; MS(ES) [MNa]$^+$=490.4

Example 6d

[(3S,6S,12R,14S)-14-((1S,3R)-3-Butylcarbamoyl-1-hydroxy-butyl)-3,12-dimethyl-2,5-dioxo-1,4-diaza-cyclotetradec-6-yl]-carbamic acid tert-butyl ester The compound can be prepared according to a similar procedure as example 6 except for using (S)-2-tert-butoxycarbonylamino-pent-4-enoic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 4.70 min; MS(ES) [MNa]$^+$=563.4

Example 6e (2R,4S)-N-Butyl-4-((2S,5S,7R)-2,7-dimethyl-3,14-dioxo-1,4-diaza-cyclotetradec-5-yl)-4-hydroxy-2-methyl-butyramide The compound can be prepared according to a similar procedure as example 6 except for using pent-4-enoic acid instead of (2S)tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 4.02 min; MS(ES) [MNa]$^+$=448.4

Example 6f: (2R,4S)-N-Butyl-4-((6S,9S,11R)-6,11-dimethyl-4,7-dioxo-1-oxa-5,8-diaza-cyclohexadec-9-yl)-4-hydroxy-2-methyl-butyramide The compound can be prepared according to a similar procedure as example 6 except for using 3-allyloxy-propionic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 3.92 min; MS(ES) [MNa]$^+$=478.4

Example 6g (2R,4S)-N-Butyl-4-((5S,8S,10R)-5,10-dimethyl-3,6-dioxo-1-oxa-4,7-diaza-cyclopentadec-8-yl)-4-hydroxy-2-methyl-butyramide The compound can be prepared according to a similar procedure as example 6 except for using allyloxy-acetic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 4.11 min; MS(ES) [MNa]$^+$=464.4

Example 6h (2R,4S)-N-Butyl-4-((5S,8S,10R)-5,10-dimethyl-3,6-dioxo-1-oxa-4,7-diaza-cyclohexadec-8-yl)-4-hydroxy-2-methyl-butyramide The compound can be prepared according to a similar procedure as example 6 except for using but-3-enyloxy-acetic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 4.44 min; MS(ES) [MNa]$^+$=478.4

Example 6i (2R,4S)-N-Butyl-4-((3S,14R,16S)-3,14-dimethyl-2, 5-dioxo-1,4,8-triaza-cyclohexadec-16-yl)-4-hydroxy-2-methyl-butyramide The compound can be prepared according to a similar procedure as example 6 except for using 3-(allyl-benzyloxycarbonyl-amino)-propionic acid (Acid Ia) instead of (2S)-tert-butoxycarbonyl-2-amino-6-heptenoic acid in step d. The cbz protecting group is removed in the last hydrogenation step.

LC/MS (Nucleosil C-18HD, 4×70 mm, 3 μM, 20-100% MeCN (6 min), 100% MeCN (1.5 min)): 2.85 min; MS(ES) [MH]$^+$=455.4, [MNa]$^+$=477.4

Example 6j (2R,4S)-N-Butyl-4-hydroxy-2-methyl-4-((2S,5S, 7R)-1,2,7-trimethyl-3,15-dioxo-1,4-diaza-cyclopentadec-5-yl)-butyramide The compound can be prepared according to a similar procedure as example 6 except for using L-Boc-N-methylalanine instead of L-Boc-alanine in step d and hex-5-enoic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 4.58 min; MS(ES) [MNa]$^+$=476.4

Example 6k (2R,4S)-N-Butyl-4-hydroxy-2-methyl-4-((2S,5S, 7R)-1,2,7-trimethyl-3,16-dioxo-1,4-diaza-cyclohexadec-5-yl)-butyramide The compound can be prepared according to a similar procedure as example 6 except for using L-Boc-N-methylalanine instead of L-Boc-alanine in step d and hept-6-enoic acid instead of (2S)tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 5.09 min; MS(ES) [MH]$^+$=468.4, [MNa]$^+$=490.4

Example 6l (2R,4S)-N-Butyl-4-hydroxy-2-methyl-4-((2S,5S, 7R)-1,2,7-trimethyl-3,17-dioxo-1,4-diaza-cycloheptadec-5-yl)-butyramide The compound can be prepared according to a similar procedure as example 6 except for using L-Boc-N-methylalanine instead of L-Boc-alanine in step d and oct-7-enoic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 5.42 min; MS(ES) [MH]$^+$=482.4, [MNa]$^+$=504.4

Example 6m (2R,4S)-N-Butyl-4-hydroxy-2-methyl-4-((5S,8S, 10R)-4,5,10-trimethyl-3,6-dioxo-1-oxa-4,7-diaza-cyclohexadec-8-yl)-butyramide The compound can be prepared according to a similar procedure as example 6 except for using L-Boc-N-methylalanine instead of L-Boc-alanine in step d and but-3-enyloxy-acetic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 4.48 min; MS(ES) [MH]$^+$=470.4, [MNa]$^+$=492.4

Example 6n (2R,4S)—N-Butyl-4-hydroxy-2-methyl-4-((2S,5S, 7R,13S)-1,2,7,13-tetramethyl-3,16-dioxo-1,4-diaza-cyclohexadec-5-yl)-butyramide The compound can be prepared according to a similar procedure as example 6 except for using L-Boc-N-methylalanine instead of L-Boc-alanine in step d and (R)-4-methyl-hept-6-enoic acid (Acid Ib) instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 5.44 min; MS(ES) [MH]$^+$=482.4, [MNa]$^+$=504.4

Example 6o (2R,4S)-N-Butyl-4-hydroxy-2-methyl-4-((2S,5S,7R, 13R)-1,2,7,13-tetramethyl-3,16-dioxo-1,4-diaza-cyclohexadec-5-yl)-butyramide The compound can be prepared according to a similar procedure as example 6 except for using L-Boc-N-methylalanine instead of L-Boc-alanine in step d and (S)-4-methyl-hept-6-enoic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 5.52 min; MS(ES) [MH]$^+$=482.4, [MNa]$^+$=504.4

Example 6p: (2R,4S)-N-Butyl-4-hydroxy-2-methyl-4-((2S,5S,7R,14R)-1,2,7,14-tetramethyl-3,16-dioxo-1,4-diaza-cyclohexadec-5-yl)-butyramide The compound can be prepared according to a similar procedure as example 6 except for using L-Boc-N-methylalanine instead of L-Boc-alanine in step d and (R)-3-methyl-hept-6-enoic acid instead of (2S)-tert-butoxycarbonyl-2-amino-6-heptenoic acid in step c.

LC/MS (Nucleosil C-18HD, 4×70 mm, 3 μM, 20-100% MeCN (6 min), 100% MeCN (1.5 min)): 5.57 min; MS(ES) [MH]$^+$=482.4, [MNa]$^+$=504.4

Example 6q (2R,4S)-N-Butyl-4-hydroxy-2-methyl-4-((5S,8S, 10R)-4,5,10,15-tetramethyl-3,6-dioxo-1-oxa-4,7-diaza-cyclohexadec-8-yl)-butyramide (mixture of diastereomers)

The compound can be prepared according to a similar procedure as example 6 except for using L-Boc-N-methylalanine instead of L-Boc-alanine in step d and (2-methyl-but-3-enyloxy)-acetic acid (Acid Ic) instead of (2S)-tert-butoxycarbonyl-2-amino-6-heptenoic acid in step c.

LC/MS (Nucleosil C-18HD, 4×70 mm, 3 µM, 20-100% MeCN (6 min), 100% MeCN(1.5 min)): 4.93 min; MS(ES) [MH]$^+$=484.4, [MNa]$^+$=506.4

Example 6r (2R,4S)-N-Butyl-4-((5S,8S,10R)-16-ethyl-4,5,10-trimethyl-3,6-dioxo-1-oxa-4,7-diaza-cyclohexadec-8-yl)-4-hydroxy-2-methyl-butyramide (mixture of diastereomers)

The compound can be prepared according to a similar procedure as example 6 except for using L-Boc-N-methylalanine instead of L-Boc-alanine in step d and (1-ethyl-but-3-enyloxy)-acetic acid (Acid Id) instead of (2S)-tert-butoxycarbonyl-2-amino-6-heptenoic acid in step c.

LC (Nucleosil C-18HD, 4×70 mm, 3 µM, 20-100% MeCN (6 min), 100% MeCN (1.5 min)): 4.95 min; MS(ES) [MH]$^+$= 498.3

Example 6s (2R,4S)-N-Butyl-4-hydroxy-2-methyl-4-((5S,8S,10R)-4,5,10-trimethyl-3,6-dioxo-17-propyl-1-oxa-4,7-diaza-cycloheptadec-8-yl)-butyramide (mixture of diastereomers)

The compound can be prepared according to a similar procedure as example 6 except for using L-Boc-N-methylalanine instead of L-Boc-alanine in step d and (1-propyl-pent-4-enyloxy)-acetic acid (Acid Ie) instead of (2S)-tert-butoxycarbonyl-2-amino-6-heptenoic acid in step c.

LC (Nucleosil C-18HD, 4×70 mm, 3 µM, 20-100% MeCN (6 min), 100% MeCN (1.5 min)): 5.69 min; MS(ES) [MH]$^+$= 526.4

Example 7

(2R,4S)-N-Butyl-4-hydroxy-2-methyl-4-((5S,8S,10R)-4,5,10-trimethyl-3,6-dioxo-1,4,7-triaza-cyclohexadec-8-yl)-butyramide The compound is prepared according to a similar procedure as example 6 except for using [(R-3-methyl-1-(4-methyl-5-oxo-tetrahydro-furan-2-yl)-hex-5-enyl]-carbamic acid tert-butyl ester instead of [(R)-3-methyl-1-(4-methyl-oxo-tetrahydro-furan-2-yl)-hept-6-enyl]-carbamic acid tert-butyl ester and L-Boc-N-methylalanine instead of L-Boc-alanine in step d and (benzyl-pent-4-enyl-amino)acetic acid instead of (2S)-tert-butoxycarbonyl-2-amino-6-heptenoic acid in step c.

LC/MS (Nucleosil C-18HD, 4×70 mm, 3 µM, 20-100% MeCN (6 min), 100% MeCN (1.5 min)): 3.04 min; MS(ES) [MH]$^+$=469.4

The starting material can be prepared as follows:

a) [(R)-3-Methyl-1-(4-methyl-5-oxo-tetrahydro-furan-2-yl)-hex-5-enyl]-carbamic acid tert-butyl ester (mixture of diastereomers)

At −78° C. under nitrogen atmosphere a solution of 2.65 g (8.9 mmol) of a mixture of [(1S,3R)-3-methyl-1-((S-5-oxo-tetrahydro-furan-2-yl)-hex-5-enyl]-carbamic acid tert-butyl ester and [(1R,3R-3-methyl-1-((R)-5-oxo-tetrahydro-furan-2-yl)-hex-5-enyl]-carbamic acid tert-butyl ester and 3.2 ml (26.7 mmol) DMPU in 30 ml THF is treated with 17.8 ml of a 1.0 M solution of LHMDS in THF. After 50 min 0.83 ml (13.3 mmol) methyl iodide are added in one portion. After 45 min the reaction is quenched with 3.3 ml propionic acid and the mixture is allowed to warm to rt and diluted with EtOAc and water. The organic phase is washed successively with 5% aqueous citric acid, water, 5% aqueous NaHCO3 and water (4×). Evaporation of the mixture and chromatography on silica gel (EtOAc/hexane 1:4) gives the title compound as a colorless oil (diastereomeric mixture).

LC/MS (Nucleosil C-18HD, 4×70 mm, 3 µM, 20-100% MeCN (6 min), 100% MeCN (1.5 min)): 5.60 min; MS(ES) [MNa]$^+$=334.2 b) [(R)-3-Methyl-1-(4-methyl-5-oxo-tetrahydro-furan-2-yl)-hex-5-enyl]-carbamic acid tert-butyl ester (mixture of diastereomers)

Under nitrogen atmosphere to 20 ml thoroughly degassed toluene are subsequently added 0.63 g (0.31 mmol) hydrido (triphenylphosphine)copper(I) hexamer, 2.9 ml polymethylhydrosiloxane and a (degassed) solution of 5.7 g (19.3 mmol) [(R)-3-methyl-1-(5-oxo-2,5-dihydro-furan-2-yl)hex-5-enyl]-carbamic acid tert-butyl ester in toluene. After stirring for 2 h at 25° C. 6 mg (0.01 mmol) of R(+)-2,2'-bis-(diphenylphosphino)-6,6'-dimethoxy-1,1-biphenyl are added as an accelerating ligand for the copper complex. After 12 h the mixture is diluted with ethyl acetate and washed with water, 5% aqueous citric acid and 5% aqueous NaHCO$_3$. Chromatography on silica gel (EtOAc/hexane 1:9, then 1:3) provides the title compound as a diastereomeric mixture.

LC/MS (Nucleosil C-18HD, 4×70 mm, 3M, 20-100% MeCN (6 nm),100% MeCN (1.5 min)): 5.28 min; MS(ES) [MNa]$^+$=320.2 c) [(R)-3-Methyl-1-(5-oxo-2,5-dihydro-furan-2-yl)-hex-5-enyl]-carbamic acid tert-butyl ester (mixture of diastereomers)

A solution of 17.15 g (46.7 mmol) of ((R)-1-benzenesulfonyl-3-methyl-hex-5-enyl)-carbamic acid tert-butyl ester in 100 ml dry THF under nitrogen atmosphere is cooled to −75° C. A solution A containing lithium furan-2-olate in THF is added over a period of 10 minutes via a canula using positive nitrogen pressure. Solution A is prepared as follows. A solution of 9.85 ml (46.7 mmol) HMDS in 100 ml dry THF under nitrogen atmosphere is cooled at −70° C. and 29.2 ml of a 1.6 M solution of BuLi in hexane (46.7 mmol) are added dropwise. After 30 minutes 3.92 g (46.7 mmol) 5H-furan-2-one in 2 ml dry THF are added dropwise and the temperature is kept at −40° C. After addition the reaction mixture is stirred at −75° C. for 1.5 h and then poured directly, with stirring, in 200 ml water and 200 ml EtOAc. The organic phase is washed successively with 5% aqueous citric acid, water (2×), 5% aqueous NaHCO3 solution and water (4×). The reaction mixture is evaporated and the residue chromatographed over silica gel (EtOAc/hexane 1:3) to yield the title compound as an oil.

LC/MS (Nucleosil C-18HD, 4×70 mm, 3 µM, 20-100% MeCN (6 min), 100% MeCN (1.5 min)): 5.20 min; MS(ES) [MNa]$^+$=318.2 d) ((R)-1-Benzenesulfonyl-3-methyl-hex-5-enyl)-carbamic acid tert-butyl ester

A solution of 4.72 g (12.06 mmol) (R)-4-isopropyl-3-((R-3-methyl-hex-5-enoyl)-5,5-diphenyl-oxazolidin-2-one in 50 ml THF and 125 ml MeOH is cooled at +4° C. and treated with 5.23 g (60.3 mmol) LiBr and 3.6 ml (24.1 mmol) DBU while stirring at 25° C. After 18 h the mixture is filtered, diluted with MTBE, washed with 1N HCl and brine and dried with $MgSO_4.H_2O$. The filtrate is concentrated under reduced pressure and triturated with pentane. The solid is removed and the solvent is distilled off at atmospheric pressure. This yields the (R)-3-methyl-hex-5-enoic acid methyl ester as a colorless liquid.

1H-NMR (400 MHz, $CDCl_3$): 5.84-5.72 (m, 1H), 5.08-5.01 (m, 2H), 3.68 (s, 3H), 2.40-2.33 (m, 1H), 2.16-1.97 (m, 4H), 0.97 (d, 3H)

The product (1.2 g, 8.44 mmol) is dissolved in 2 ml THF and cooled to −90° C. A 1M solution of DibalH in DCM (10.1 ml) is added dropwise over 15 minutes. After 1 h at −90° C. the mixture is quenched with 0.34 ml MeOH, warmed to 25° C. and washed with 5% aqueous citric acid. The organic phase is carefully concentrated under reduced pressure, dissolved in 3 ml MeCN and treated immediately with 0.987 g (8.44 mmol) carbamic acid tert-butyl ester, 1.50 g (8.44 mmol) sodium 4-methyl-benzenesulfinate and 0.44 ml (11.7 mmol) formic acid. After stirring for 2 days the mixture is diluted with 50 ml EtOAc and 50 ml water. The organic phase is successively washed with 5% aqueous citric acid, water, 5% aqueous $NaHCO_3$ solution and four times with water. Concentration in vacuo yields the title compound as a colorless oil that solidifies upon standing.

LC/MS (Nucleosil C-18HD, 4×70 mm, 3 µM, 20-100% MeCN (6 min), 100% MeCN (1.5 min)): 5.94 min; MS(ES) $[MNa]^+$=390.2 e) (R)-4-Isopropyl-3-((R)-3-methyl-hex-5-enoyl)-5,5-diphenyl-oxazolidin-2-one

To a stirred suspension of 22.35 g (117 mmol) CuI in 400 ml THF at −40° C. are added dropwise 70 ml (140 mmol) of a 2M THF solution of allylmagnesium chloride. After 1 h the mixture is cooled to −78° C. and 17.7 ml (140 mmol) BF3.OEt2 are added in 15 minutes. Then a solution of 41 g (117 mmol) (R)-3-((E)-but-2-enoyl)-4-isopropyl-5,5-diphenyl-oxazolidin-2-one in 100 ml THF is added as quickly as possible. The temperature rises to −40° C. Stirring is continued for 1 h and then the mixture is quenched with 500 ml 10% aqueous NH4Cl. The mixture is stirred for 1 h at 25° C. and filtered over celite and washed with 150 ml TBME. The organic phase is washed successively with water, 10% aqueous NaHCO3, water, 5% citric acid and water. Chromatography (silica gel, EE/hexane 1:10) of the crude product yields the (R)-4isopropyl-3-((R)-3-methyl-hex-5-enoyl)-5,5-diphenyl-oxazolidin-2-one.

$[\alpha]_D$ +171.7° (c=1, DCM)

1H-NMR (400 MHz, $CDCl_3$): 7.52-7.27 (m, 10H), 5.79-5.68 (m, 1H), 5.42 (d, 1H), 5.03-4.98 (m, 2H), 2.89-2.65 (m, 2H), 2.10-1.96 (m, 4H), 0.92 (d, 3H), 0.79 (d, 6H)

LC/MS (Nucleosil C-18HD, 4×70 mm, 3 µM, 20-100% MeCN (6 min), 100% MeCN (1.5 min)): 7.11 min; MS(ES) $[MNa]^+$=414.2

The following compounds can be obtained by a similar procedure:

Example 7a (2R,4S)-N-Butyl-4-hydroxy-2-methyl-4-((2S,5S,7R,12R)-2,7,12-trimethyl-3,15-dioxo-1,4-diaza-cyclopentadec-5-yl)-butyramide The compound is prepared according to a similar procedure as example 6 except for using [(R)-3-methyl-1-(4-methyl-5-oxo-tetrahydro-furan-2-yl)hex-5-enyl]-carbamic acid tert-butyl ester instead of [(R-3-methyl-1-(4-methyl-5-oxo-tetrahydro-furan-2-yl)-hept-6-enyl]-carbamic acid tert-butyl ester in step d and (S)-4-methyl-hept-6-enoic acid instead of (2S)-tert-butoxycarbonyl-2-amino-6-heptenoic acid in step c.

LC/MS (Nucleosil C-18HD, 4×70 mm, 3 µM, 20-100% MeCN (6 min), 100% MeCN (1.5 min)): 4.61 min; MS(ES) $MNa^+$=476.4

Example 7b (2R,4S)-N-Butyl-4-hydroxy-2-methyl-4-((2S,5S,7R,12S)-2,7,12-trimethyl-3,15-dioxo-1,4-diaza-cyclopentadec-5-yl)-butyramide The compound is prepared according to a similar procedure as example 6 except for using [(R)-3-methyl-1-(4-methyl-5-oxo-tetrahydro-furan-2-yl)-hex-5-enyl]-carbamic acid tert-butyl ester instead of [(R-3-methyl-1-(4-methyl-5-oxo-tetrahydro-furan-2-yl-hept-6-enyl]-carbamic acid tert-butyl ester in step d and (R)-4-methyl-hept-6-enoic acid (Acid Ib) instead of (2S)-tert-butoxycarbonyl-2-amino-6-heptenoic acid in step c.

LC/MS (Nucleosil C-18HD, 4×70 mm, 3 µM, 20-100% MeCN (6 min), 100% MeCN (1.5 min)): 4.62 min; MS(ES) $MNa^+$=476.4

Example 8

(2R,4S)-4-((2S,5S,7R,15S)-15-Acetylamino-2,7-dimethyl-3,16-dioxo-1,4-diaza-cyclohexadec-5-yl)-N-butyl-4-hydroxy-2-methyl-butyramide A solution of 45 mg (0.079 mmol) [(3S,6S,14R,16S)-16-((1S,3R)-3-butylcarbamoyl-1-hydroxy-butyl)-3,14-dimethyl-2,5-dioxo-1,4diaza-cyclohexadec-6-yl]-carbamic acid tert-butyl ester (example 6) in 1 ml 4N HCl/dioxane is kept for 3 h and then evaporated. The residue is taken up in 3 ml THF and 1 ml EtOH and 1 ml 10% aqueous sodium carbonate, cooled to 0° C. and stirred vigorously. 0.112 ml (1.6 mmol) acetyl chloride are added and stirring is continued for 1 h. The solvents are evaporated and the residue is stirred with water and TBME/hexane for 30 min. The mixture is filtered to yield the title compound.

LC/MS (Nucleosil C-18HD, 4×70 mm, 3 µM, 20-100% MeCN (6 min), 100% MeCN (1.5 min)): 4.06 min; MS(ES) $[MNa]^+$=533.4

Example 9

N-[(3S,6S,14R,16S)-16-((1S,3R)-3-Butylcarbamoyl-1-hydroxy-butyl)-3,14-dimethyl-2,5-dioxo-1,4-diaza-cyclohexadec-6-yl]-isonicotinamide A solution of 45 mg (0.079 mmol) [(3S,6S,14R,16S)-16-((1S,3R)-3-butylcarbamoyl-1-hydroxy-butyl)-3,14-dimethyl-2,5-dioxo-1,4-diaza-cyclohexadec-6-yl]-carbamic acid tert-butyl ester (example 6) in 1 ml 4N HCl/dioxane is kept for 3 h and then evaporated. The residue is taken up in 2 ml THF and 2 ml EtOH and treated subsequently with 14 mg (0.118 mmol) isonicotinic acid, 13 mg (0.095 mmol) HOBt, 22 mg (0.118 mmol) EDCl and 0.055 ml (0.4 mmol) $Et_3N$. After 24 h the mixture is diluted with EtOAc, washed subsequently with water, 5% citric acid, water, saturated aqueous sodium bicarbonate and water. The organic phase is evaporated, the residual solid is washed with EtOAc and filtered to yield the product as a white powder.

LC/MS (Nucleosil C-18HD, 4×70 mm, 3 μM, 20-100% MeCN (6 min), 100% MeCN (1.5 min)): 3.69 min; MS(ES) [MNa]$^+$=596.4

Example 10

(2R,4S)-N-Butyl-4-((3S,6S,8R)-3,8-dimethyl-1,1,4-trioxo-1lambda*6*-thia-5-aza-cyclohexadec-6-yl)-4-hydroxy-2-methyl-butyramide A solution of 74 mg (0.15 mmol) (2R,4S)-N-butyl-4-(-(3S,6S,8R)-3,8-dimethyl-1,1,4-trioxo-1lambda*6*-thia-5-aza-cyclohexadec-11-en-6-yl)-4-hydroxy-2-methyl-butyramide in 5 ml MeOH is stirred in the presence of 20 mg 10% Pd—C under a hydrogen atmosphere for 1 h. The mixture is filtered over a pad of celite and the solvent evaporated. The residue is crystallized from toluene and the title compound is isolated as a white powder.

LC/MS (Nucleosil C-18HD, 4×70 mm, 3 μM, 20-100% MeCN (6 min), 100% MeCN (1.5 min)): 4.88 min; MS(ES) [MNa]$^+$=511.4

The starting material can be prepared as described hereafter:

a) (2R,4S)-N-Butyl-4-((3S,6S,8R)-3,8-dimethyl-1,1,4-trioxo-1 lambda*6*-thia-5-aza-cyclohexadec-11-en-6-yl)-4-hydroxy-2-methyl-butyramide A solution of 99 mg (0.21 mmol) (3S,6S,8R)-3,8-dimethyl-6-((2S,4R)-4-methyl-5-oxo-tetra-hydro-furan-2-yl)-1,1-dioxo-1lambda*6*-thia-5-aza-cyclohexadec-11-en-4-one in 1.5 ml butylamine is heated at 65° C. for two hours. The mixture is evaporated and the residue chromatographed on silica gel (EtOAc/hexane 1:1) to yield the title compound as a white solid.

LC/MS (Nucleosil C-18HD, 4×70 mm, 3 μM, 20-100% MeCN (6 min), 100% MeCN (1.5 min)): 4.64 min; MS(ES) [MNa]$^+$=509.4 b) (3S,6S,8R)-3,8-Dimethyl-6-((2S,4R)-4-methyl-5-oxo-tetrahydro-furan-2-yl)-1,1-dioxo-1lambda*6*-thia-5-aza-cyclohexadec-11-en-4-one Under a nitrogen atmosphere to 200 ml refluxing DCM is added a solution of 10 mg (0.01 mmol) tricyclohexylphosphine[1,3-bis(2,4,6-trimethylphenyl)-4,5-dihydroimidazol-2-ylidene][benzylidine]ruthenium(IV)dichloride ('Grubbs 2' catalyst) in 1 ml DCM, followed by the dropwise addition of a solution of 100 mg (0.218 mmol) (S)-3-(hex-5-ene-1-sulfonyl)-2-methyl-N-[(1S,3R)-3-methyl-1-((2S,4R)-4-methyl-5-oxo-tetrahydro-furan-2-yl)hept-6-enyl]-propionamide in 5 ml DCM. After 2 h the mixture is cooled to rt and quenched by the addition of 0.05 ml butyl vinyl ether and 0.2 g activated charcoal. The mixture is passed through a pad of silica gel (EtOAc/hexane 1:1) to yield the title compound as a solid.

LC/MS (Nucleosil C-18HD, 4×70 mm, 3 μM, 20-100% MeCN (6 min), 100% MeCN (1.5 min)): 4.87 min; MS(ES) [MNa]$^+$=436.2 c) (S)-3-(Hex-5-ene-1-sulfonyl)-2-methyl-N-[(1S,3R)-3-methyl-1-((2S,4R)-4-methyl-5-oxo-tetrahydro-furan-2-yl)-hept-6-enyl]-propionamide A solution of 162 mg (0.5 mmol) of [(R)-3-Methyl-1-(4-methyl-5-oxo-tetrahydro-furan-2-yl)-hept-6-enyl]-carbamic acid tert-butyl ester (mixture of diastereomers, Example 6, step f) in 2 ml 4N HCl in dioxane is kept 3 h at rt and concentrated in vacuo. The residue is taken up in 10 ml DCM and treated with 157 mg (0.675 mmol) (S)-3-(hex-5-ene-1-sulfonyl)-2-methyl-propionic acid (Acid IIa), 91 mg (0.59 mmol) HOBt.H$_2$O, 129 mg (0.675 mmol) EDC.HCl and 0.383 ml (2.75 mmol) Et$_3$N and stirred overnight. The mixture is diluted with EtOAc and washed successively with water, 5% aqueous citric acid, water, 5% aqueous NaHCO$_3$ and water (4×). Evaporation of the mixture and chromatography on silica gel (EtOAc/hexane 1:3, 1:2 and 1:1) gives the faster eluting diastereomer and then the title product.

LC/MS (Nucleosil C-18HD, 4×70 mm, 3 μM, 20-100% MeCN (6 min), 100% MeCN (1.5 min)): 5.64 min; MS(ES) [MNa]$^+$=464.2

The following compounds can be obtained via a similar procedure:

Example 10a

N-Butyl-4-((8R)-3,8-dimethyl-1,1,4-trioxo-1lambda*6*-thia-5-aza-cyclopentadec-6-yl)-4-hydroxy-2-methyl-butyramide The title compound is obtained as a mixture of diastereomers using racemic 2-methyl-3-(pent-4-ene-1-sulfonyl) propionic acid (Acid IIb) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 4.49 and 4.61 min (2 diastereomers); MS(ES) [MNa$_2$–H]$^+$=497.2

Example 10b (2R,4S)-N-Butyl-4-((3S,6S,8R)-3,8-dimethyl-1,1,4-trioxo-1 lambda*6*-thia-5-aza-cyclotetradec-6-yl)-4-hydroxy-2-methyl-butyramide The title compound is obtained using 2-methyl-3-(pent-4-ene-1-sulfonyl)-propionic acid (Acid IId) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min),100% MeCN (1.5 min)): 4.25 min; MS(ES) [MNa]$^+$=483.2

Example 10c (2R,4S)-N-Butyl-4-((3S,6S,8R)-3,8-dimethyl-1,1,4-trioxo-1lambda*6*-thia-5-aza-cycloheptadec-6-yl)-4-hydroxy-2-methyl-butyramide The title compound is obtained using (S)-3-(hept-6-ene-1-sulfonyl)-2-methyl-propionic acid (Acid IIe) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 5.18 min; MS(ES) [MNa]$^+$=525.4

Example 10d

N-Butyl-4-hydroxy-2-methyl-4-((7R)-7-methyl-1,1,
3-trioxo-1 lambda*6*-thia-4-aza-cyclohexadec-5-
yl)-butyramide The title compound is obtained as a mixture of diastereomers using 2-methyl-3-(pent-4-ene-1-sulfonyl)propionic acid (Acid IIf) instead of (S)-3-(hex-5-ene-1-sulfonyl)-2-methyl-propionic acid in step c.

LC/MS (Nucleosil C-18HD, 4×70 mm, 3 µM, 20-100% MeCN (6 min), 100% MeCN (1.5 min)): 5.22 and 5.40 min (2 diastereomers); MS(ES) [MNa]$^+$=497.2 and 497.2

Example 10e

N-Butyl-4-hydroxy-2-methyl-4-((8R)-8-methyl-1,1,
4-trioxo-1lambda*6*-thia-5-aza-cyclohexadec-6-yl)-
butyramide The title compound is obtained as a mixture of diastereomers using 3-(hex-5-ene-1-sulfonyl)-propionic acid (Acid IIg) instead of (S)-3-(hex-5-ene-1-sulfonyl)-2-methyl-propionic acid in step c.

LC/MS (Nucleosil C-18HD, 4×70 mm, 3 µM, 20-100% MeCN (6 min), 100% MeCN (1.5 min)): 4.71 and 4.83 min (2 diastereomers); MS(ES) [MNa]$^+$=497.2 and 497.2

Example 10f

N-Butyl-4-hydroxy-2-methyl-4-((9R)-9-methyl-1,1,
5-trioxo-1lambda*6*-thia-6-aza-cyclohexadec-7-yl)-
butyramide The title compound is obtained as a mixture of diastereomers using 3-(hex-5-ene-1-sulfonyl)-propionic acid (Acid IIh) instead of (S)-3-(hex-5-ene-1-sulfonyl)-2-methyl-propionic acid in step c.

LC/MS (Nucleosil C-18HD, 4×70 mm, 3 µM, 20-100% MeCN (6 min), 100% MeCN (1.5 min)): 4.25 and 4.34 min (1:1 diastereomeric mixture); MS(ES) [MNa]$^+$=497.2

Example 11

N-Butyl-4-hydroxy-4-((9R)-16-methoxy-9-methyl-
13-oxo-2,12,17-triaza-bicyclo[12.3.1]octadeca-1
(17),14(18),15-trien-11-yl)-2-methyl-butyramide A solution of 16-methoxy-9-methyl-11-(4-methyl-5-oxo-tetrahydro-furan-2-yl)-2,12,17-triaza-bicyclo[12.3.1]octadeca-1(17),14(18),15-trien-13-one (49 mg, 0.12 mmol) in 1.2 ml butylamine is stirred at 50° for 3 h. Excess butylamine is evaporated and the residue purified by chromatography on silica gel to afford the title compound (mixture of diastereomers) as a slightly yellow powder.

Mp 178-182° C.
HPLC (XTerra 4.5 cm, 95% CH$_3$CN, 50° C.): 3.98 min. MS (LC/MS): [MH]$^+$=477.3

The starting material can be prepared as follows:

a) 16-Methoxy-9-methyl-1-(4-methyl-5-oxo-tetrahydro-furan-2-yl)-2,12,17-triaza-bicyclo[12.3.1]octadeca-1(17),14(18),15-trien-13-one A solution of 60 mg (0.15 mmol) 16-methoxy-9-methyl-11-(4-methyl-5-oxo-tetrahydro-furan-2-yl)-2,12,17-triaza-bicyclo[12.3.1]octadeca-1(17),5,14(18),15-tetraen-13-one in 2 ml MeOH is hydrogenated under 1 atm hydrogen in the presence of 9 mg Pd/C for 2 h at rt. Filtration and evaporation yields the title compound as a brownish foam.

b) 16-Methoxy-9-methyl-11-(4-methyl-5-oxo-tetrahydro-furan-2-yl)-2,12,17-triaza-bicyclo[12.3.1]
octadeca-1(17),5,14(18),15-tetraen-one A solution of 90 mg (0.21 mmol) 2-but-3-enylamino-6-methoxy-N-[3-methyl-1-(4-methyl-5-oxo-tetrahydro-furan-2-yl)-hept-6-enyl]-isonicotinamide in 6 ml DCM is added dropwise over 30 min to a refluxing solution of 3.5 mg tricyclohexylphosphine [1,3-bis(2,4,6-trimethyl-phenyl)-4,5-dihydroimidazol-2-ylidene][benzylidene]ruthenium(IV) dichloride('Grubbs second generation catalyst') in 6 ml DCM and then stirred for 1 h at reflux. LC/MS shows that only little product has been formed, therefore, 7 mg catalyst are added and the mixture stirred for 18 h at reflux. Again, 11 mg catalyst are added and heating continued for 4 h. The reaction mixture is directly chromatographed on silica gel and eluted with DCM/MeOH 98:2 to yield the title compound (mixture of diastereomers) as a greenish foam.

HPLC (XTerra 4.5 cm, 95% CH$_3$CN, 50° C.): 3.85 min and 4.45 min (diastereoisomers). MS (LC/MS): 402.4 c) 2-But-3-enylamino-6-methoxy-N-[3-methyl-1-(4-methyl-5-oxo-tetrahydro-furan-2-yl)-hept-6-enyl]-
isonicotinamide A solution of 155 mg (0.7 mmol) 2-but-3-enylamino-6-methoxy-isonicotinic acid (Acid IIIb), 105 mg (0.47 mmol) (R)-3-methyl-1-(4-methyl-5-oxo-tetrahydro-furan-2-yl) hept-6-enyl]-carbamic acid tert-butyl ester and 63 mg (0.42 mmol) HOBt.H$_2$O in 8 ml DMF is cooled to 0°, treated with 107 mg (0.56 mmol) EDC.HCl and stirred at rt for 3 h. The reaction mixture is diluted with EtOAc and washed with 0.5 N aqueous citric acid, 2 M KHCO$_3$ and brine, then dried over Na$_2$SO$_4$, filtered and evaporated. Chromatography on silica gel yields the title product as a colorless oil.

HPLC (XTerra 4.5 cm, 95% CH$_3$CN, 50° C.): 4.25 min. MS (LC/MS): [MH]$^+$=430.5

The following compounds can be obtained via a similar procedure:

Example 11a

N-Butyl-4-hydroxy-4-((9R)-16-methoxy-9-methyl-
13-oxo-2,12-diaza-bicyclo[12.3.1]octadeca-1(17),14
(18),15-trien-11-yl)-2-methyl-butyramide The title compound is obtained as a mixture of diastereomers using 3-(benzyloxycarbonyl-but-3-enyl-amino)-5-methoxy-benzoic acid (Acid IIIc) instead of (S)-3-(hex-5-ene-1-sulfonyl)-2-methyl-propionic acid in step c.

LC/MS (Nucleosil C-18HD, 4×70 mm, 3 µM, 20-100% MeCN (6 min), 100% MeCN(1.5 min)): 4.21 min; MS(ES) [MNa]$^+$=498.4

Example 11b

N-Butyl-4-hydroxy-2-methyl-4-((11R)-11-methyl-
15-oxo-2-oxa-14-aza-bicyclo[14.3.1]icosa-1(19),16
(20),17-trien-13-yl)-butyramide The title compound is obtained as a mixture of diastereomers using 3-hex-5-enyloxy-benzoic acid (Acid IIId) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 6.04 and 6.13 min (mixture of diastereomers); MS(ES) [MNa]$^+$=497.4

Example 11c

N-Butyl-4-hydroxy-2-methyl-4-((9R)-9-methyl-13-oxo-2-oxa-12-aza-bicyclo[12.3.1]octadeca-1(17),14 (18),15-trien-11-yl)-butyramide The title compound is obtained as a mixture of diastereomers using 3-but-3-enyloxy-benzoic acid (Acid IIIe) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 5.44 min; MS(ES) [MNa]$^+$=469.2

Example 11d

N-Butyl-4-hydroxy-2-methyl-4-((10R)-10-methyl-14-oxo-2-oxa-13-aza-bicyclo[13.3.1]nonadeca-1 (18),15(19),16-trien-12-yl)-butyramide The title compound is obtained as a mixture of diastereomers using 3-pent-4-enyloxy-benzoic acid (Acid IIIf) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 5.87 min; MS(ES) [MNa]$^+$=483.2

Example 11e

N-Butyl-4-((6R)-6,12-dimethyl-2,13-dioxo-3,12-diaza-bicyclo[12.3.1]octadeca-1(18),14,16-trien-4-yl)-4-hydroxy-2-methyl-butyramide The title compound is obtained as a mixture of diastereomers using N-allyl-N-methyl-isophthalamic acid (Acid IVa) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 4.35 min; MS(ES) [MNa]$^+$=496.4

Example 11f

N-Butyl-4-((6R)-12-ethyl-6-methyl-2,13-dioxo-3,12-diaza-bicyclo[12.3.1]-octadeca-1(18),14,16-trien-4-yl)-4-hydroxy-2-methyl-butyramide The title compound is obtained as a mixture of diastereomers using N-allyl-N-ethyl-isophthalamic acid (Acid IVb) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 4.64 min; MS(ES) [MNa]$^+$=510.4

Example 11g

N-Butyl-4-hydroxy-2-methyl-4-((6R)-6-methyl-2,13-dioxo-12-propyl-3,12-diaza-bicyclo[12.3.1]octadeca-1(18),14,16-trien-4-yl)-butyramide The title compound is obtained as a mixture of diastereomers using N-allyl-N-propyl-isophthalamic acid (Acid IVc) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 5.01 min; MS(ES) [MNa]$^+$=524.4

Example 11h

N-Butyl-4-((6R)-12-cyclopropyl-6-methyl-2,13-dioxo-3,12-diaza-bicyclo[12.3.1]octadeca-1(18),14,16-trien-4-yl)-4-hydroxy-2-methyl-butyramide The title compound is obtained as a mixture of diastereomers using N-allyl-N-cyclopropyl-isophthalamic acid (Acid IVd) instead of (S)-3-(hex-5-ene-1-sulfonyl)-2-methyl-propionic acid in step c.

LC/MS (Nucleosil C-18HD, 4×70 mm, 3 μM; 20-100% MeCN (6 min), 100% MeCN (1.5 min)): 4.68 min; MS(ES) MH$^+$=500.4, [MNa]$^+$=522.4

Example 11i

N-Butyl-4-hydroxy-4-((6R)-16-methoxy-6,12-dimethyl-2,13-dioxo-3,12-diaza-bicyclo[12.3.1]octadeca-1(18),14,16-trien-4-yl)-2-methyl-butyramide The title compound is obtained as a mixture of diastereomers using N-allyl-N-methyl-5-methoxy-isophthalamic acid (Acid IVe) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 4.82 min; MS(ES) [MNa]$^+$=526.4

Example 11j

N-Butyl-4-((6R)-12-ethyl-16-methoxy-6-methyl-2,13-dioxo-3,12-diaza-bicyclo[12.3.1]octadeca-1(18),14,16-trien-4-yl)-4-hydroxy-2-methyl-butyramide The title compound is obtained as a mixture of diastereomers using N-allyl-N-ethyl-5-methoxy-isophthalamic acid (Acid IVf) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 4.82 min; MS(ES) MH$^+$=518.4, [MNa]$^+$=540.4

Example 11k

N-Butyl-4-((6R)-12-propyl-16-methoxy-6-methyl-2,13-dioxo-3,12-diaza-bicyclo[12.3.1]octadeca-1(18),14,16-trien-4-yl)-4-hydroxy-2-methyl-butyramide The title compound is obtained as a mixture of diastereomers using N-allyl-N-propyl-5-methoxy-isophthalamic acid (Acid IVg) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 5.19 min; MS(ES) MH$^+$=532.4, [MNa]$^+$=554.4

Example 11l

N-Butyl-4-hydroxy-2-methyl-4-((6R)-6-methyl-2,14-dioxo-3,13-diaza-bicyclo[13.3.1]nonadeca-1(18),15(19),16-trien-4-yl)-butyramide The title compound is obtained as a mixture of diastereomers using N-but-3-enyl-isophthalamic acid (Acid IVh) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 4.34 min; MS(ES) MH$^+$=474.4, [MNa]$^+$=496.4

Example 11m

N-Butyl-4-hydroxy-2-methyl-4-((9R)-9-methyl-2,2,13-trioxo-2lambda*6*-thia-12-aza-bicyclo[12.3.1]octadeca-1(17),14(18),15-trien-11-yl)-butyramide The title compound is obtained as a mixture of diastereomers using 3-(but-3-ene-1-sulfonyl)-benzoic acid (Acid IIIg) instead of (S)-3-(hex-5-ene-1-sulfonyl)-2-methyl-propionic acid in step c.

LC/MS (Nucleosil C-18HD, 4×70 mm, 3 μM, 20-100% MeCN (6 min), 100% MeCN (1.5 min)): 4.65 min; MS(ES) [MNa]$^+$=517.2

Example 12

N-Butyl-4-hydroxy-2-methyl-4-((6R)-6-methyl-2,13-dioxo-3,12-diaza-bicyclo[12.3.1]octadeca-1(18),14,16-trien-4-yl)-butyramide The title compound is obtained as a mixture of diastereomers and prepared according to a similar procedure as example 11 except for using [(R)-3-methyl-1-(4-methyl-5-oxo-tetra-hydro-furan-2-yl)hex-5-enyl]-carbamic acid tert-butyl ester (for preparation see example 7) instead of [(R)-3-methyl-1-(4-methyl-5-oxo-tetrahydro-furan-2-yl)hept-6-enyl]-carbamic acid tert-butyl ester (described in example 6) and N-but-3-enyl-isophthalamic acid (Acid IVh) instead of 2-but-3-enylamino-6-methoxy-isonicotinic acid (Acid IIIb) in step c.

LC/MS (Nucleosil C-18HD, 4×70 mm, 3 μM, 20-100% MeCN (6 min), 100% MeCN (1.5 min)): 3.95 min; MS(ES) [MNa]$^+$=482.4

The following compounds can be prepared via a similar procedure:

Example 12a

N-Butyl-4-((9R)-3-ethyl-9-methyl-2,13-dioxo-4-oxa-3,12-diaza-bicyclo-[12.3.1]octadeca-1(17),14(18),15-trien-11-yl)-4-hydroxy-2-methyl-butyramide The title compound is obtained as a mixture of diastereomers using N-allyloxy-N-ethyl-isophthalamic acid (Acid IVi) instead of N-but-3-enyl-isophthalamic acid.

LC/MS (Nucleosil C-18HD, 4×70 mm, 3 μM, 20-100% MeCN (6 min), 100% MeCN (1.5 min)): 5.14 min; MS(ES) [MNa]$^+$=556.4

Example 12b

N-Butyl-4-((6R)-11-ethyl-15-methoxy-6-methyl-2,12-dioxo-3,11-diaza-bicyclo[11.3.1]heptadeca-1(17),8,13,15-tetraen-4-yl)-4-hydroxy-2-methyl-butyramide The title compound is obtained as a mixture of diastereomers using N-allyl-N-ethyl-5-methoxy-isophthalamic acid (Acid IVf) instead of N-but-3-enyl-isophthalamic acid. Under the hydrogenation conditions used in the last step the C=C double bond is not reduced.

LC/MS (Nucleosil C-18HD, 4×70 mm, 3 μM, 20-100% MeCN (6 min), 100% MeCN (1.5 min)): 4.33 min; MS(ES) [MNa]$^+$=524.4

Example 13

(2R,4S)-N-Butyl-4-((10R,12S)-17-ethoxy-10-methyl-14-oxo-2,13,18-triaza-bicyclo[13.3.1]nonadeca-1(18),15(19),16-trien-12-yl)-4-hydroxy-2-methyl-butyramide The title compound is obtained similarly to Example 11 as a single diastereomer, using 2-ethoxy-6-pent-4-enylamino-isonicotinic acid (Acid IIIh) instead of 2-but-3-enylamino-6-methoxy-isonicotinic acid in step c and using diastereomerically pure [(1S,3R)-3-methyl-1-((2S,4R)-4-methyl-5-oxo-tetrahydrofuran-2-yl)-hept-6-enyl]-carbamic acid tert-butyl ester in step c.

LC (Nucleosil C-18HD, 4×70 mm, 3 μM, 20-100% MeCN (6 min), 100% MeCN (1.5 min)): 5.00 min; MS(ES) [MH]$^+$=505.2

The starting material can be obtained as follow a) [(1S,3R)-3-Methyl-1-((2S,4R)-4-methyl-5-oxo-tetrahydro-furan-2-yl)-hept-6-enyl]-carbamic acid tert-butyl ester The title compound is obtained in analogy to example 6 using diastereomerically pure [(1S,3R)-3,7-dimethyl-1-((S)-5-oxo-2,5-dihydro-furan-2-yl)-oct-6-enyl]-carbamic acid tert-butyl ester in step g.

Rf: (hexane/ethyl acetate 3:1) 0.36

$^1$H-NMR (400 MHz, CDCl$_3$): 5.86-5.76 (m, 1H), 5.08-4.95 (m, 2H), 4.55-4.05 (m, 1H), 4.37 (d, 1H), 2.78-2.68 (m, 1H), 2.49-2.66 (m, 1H), 2.18-2.02 (m, 2H), 2.01-1.92 (m, 1H), 1.74-1.66 (m, 1H), 1.59-1.26 (m, 4H), 1.47 (s, 9H), 1.31 (t, 3H), 0.97 (t, 3H)

LC/MS (Nucleosil C-18HD, 4×70 mm, 3 μM, 40-100% MeCN (6 min), 100% MeCN (1.5 min)): 4.94 min; MS(ES) [MNa]$^+$=348.2 b) [(1S,3R)-3,7-Dimethyl-1-((S)-5-oxo-2,5-dihydro-furan-2-yl)-oct-6-enyl]-carbamic acid tert-butyl ester 61.6 g (0.4 mol) R-(+)-citronellal, 44.46 g (0.38 mol) carbamic acid tert-butyl ester, 74.76 g (0.42 mol) sodium 4-methyl-benzenesulfinate and 22.6 ml (0.6 mol) formic acid are stirred in 300 ml acetonitrile at 25° C. for 4 days. The mixture is diluted with 700 ml EtOAc and 1000 ml water. The organic phase is successively washed with 5% aqueous citric acid, water, 5% aqueous NaHCO$_3$ solution and four times with water. After addition of 20 ml EtOH the solution is concentrated in vacuo yielding [(R)-3,7-dimethyl-1-(toluene-4-sulfonyl)-oct-enyl]-carbamic acid tert-butyl ester as a colorless oil that solidifies upon standing.

Rf (EtOAc/hexane 1:3) 0.49

LC/MS (Nucleosil C-18HD, 4×70 mm, 3 μM, 20-100% MeCN (6 min), 100% MeCN (1.5 min)): 6.82 min; MS(ES) [MNa]$^+$=432.2

This material is dissolved in 500 ml THF under nitrogen atmosphere and cooled to −75° C. A solution A containing lithium furan-2-olate in THF is added over a period of 20 minutes via a canula using positive nitrogen pressure. Solution A is prepared as follows. 78 ml (0.368 mol) HMDS in 500 ml dry THF under nitrogen atmosphere are cooled at −70° C. and 230 ml of a 1.6 M solution of BuLi in hexane (0.368 mol) are added dropwise. After 30 minutes 30.92 g (0.368 mol) 5H-furan-2-one in 10 ml dry THF are added dropwise and the temperature is kept below −40° C. Solution A is stirred at −40° C. to prevent the formation of a precipitate before it is added. After addition the reaction mixture is stirred at −75° C. for 1.5 h and then poured directly into a stirred mixture of 1000 ml water and 1000 ml EtOAc. The organic phase is washed successively with 5% aqueous citric acid, water, 5% aqueous NaHCO3 solution and water. The reaction mixture is evaporated and the residue chromatographed over silica gel (EtOAc/hexane 1:5) to yield an oily product. After crystallization from hexane results a mixture of [(1S,3R)-3,7-dimethyl-1-((S)-5-oxo 2,5-dihydro-furan-2-yl)-oct-6-enyl]-carbamic acid tert-butyl ester and [(1R,3R)-3,7-dimethyl-1-((R)-5-oxo-2,5-dihydro-furan-2-yl) oct-6-enyl]-carbamic acid tert-butyl ester as a white powder. Both diastereomers are quantitatively separated over a Chiralpak AD column (5×50 cm) with hexane/isopropanol=97:3 as eluent. The slower moving diastereomer is isolated and after evaporation of the eluent the pure diastereomer [(1S,3R)-3,7-dimethyl-1-((S)-5-oxo-2,5-dihydro-furan-2-yl)oct-6-enyl]-carbamic acid tert-butyl ester is obtained as a white powder.

Mp. 58-61° C.

$^{13}$C-NMR (100 MHz, CDCl$_3$): 173.2, 155.2, 154.8, 131.4, 124.1, 121.3, 84.8, 79.6, 49.1, 39.6, 36.1, 29.1, 28.1, 25.6, 25.1, 19.5, 17.5

The following compounds can be prepared via a similar procedure:

Example 13a (2R,4S)-N-Butyl-4-((9R,11S)-9,16-dimethyl-13-oxo-2,12,17-triaza-bicyclo-[12.3.1]octadeca-1(17),14(18),15-trien-11-yl)-4-hydroxy-2-methyl-butyramide The title compound is obtained using 2-but-3-enylamino-6-methyl-isonicotinic acid (Acid IIIa) instead of 2-ethoxy-6-pent-4-enylamino-isonicotinic acid (Acid IIIh).

LC/MS (Nucleosil C-18HD, 4×70 mm, 3 μM, 20-100% MeCN (6 min), 100% MeCN (1.5 min)): 3.59 min; MS(ES) [MH]$^+$=461.4

Example 13b (2R,4S)-N-Butyl-4-((9R,11S)-3-ethyl-16-methoxy-9-methyl-13-oxo-2,12,17-triaza-bicyclo[12.3.1]octadeca-1(17),14(18),15-trien-11-yl)-4-hydroxy-2-methyl-butyramide The title compound is obtained using 2-(1-ethyl-but-3-enylamino)-6-methoxy-isonicotinic acid (Acid IIIi) instead of 2-ethoxy-6-pent-4-enylamino-isonicotinic acid (Acid IIIh).

LC (Nucleosil C-18HD, 4×70 mm, 3 μM, 20-100% MeCN (6 min), 100% MeCN (1.5 min)): 4.72 min; MS(ES) [MH]$^+$=505.4

Example 13c (2R,4S)-N-Butyl-4-((4S,6R)-16-ethoxy-12-ethyl-6-methyl-2,13-dioxo-3,12-diaza-bicyclo[12.3.1]octadeca-1(18),14,16-trien-4-yl)-4-hydroxy-2-methyl-butyramide The title compound is obtained using N-allyl-N-ethyl-5-ethoxy-isophthalamic acid (Acid IVj) instead of 2-ethoxy-6-pent-4-enylamino-isonicotinic acid (Acid IIIh).

LC/MS (Nucleosil C-18HD, 4×70 mm, 3 μM, 20-100% MeCN (6 min), 100% MeCN (1.5 min)): 5.11 min; MS(ES) MH$^+$=532.4, [MNa]$^+$=554.4

Example 13d (2R,4S)-N-Butyl-4-((4S,6R)-12-ethyl-16-isopropoxy-6-methyl-2,13-dioxo-3,12-diaza-bicyclo [12.3.1]octadeca-1(18),14,16-trien-4-yl)-4-hydroxy-2-methyl-butyramide The title compound is obtained using N-allyl-N-ethyl-5-isopropoxy-isophthalamic acid (Acid IVk) instead of 2-ethoxy-6-pent-4-enylamino-isonicotinic acid (Acid IIIh).

LC/MS (Nucleosil C-18HD, 4×70 mm, 3 μM, 20-100% MeCN (6 min), 100% MeCN (1.5 min)): 5.35 min; MS(ES) MH$^+$=546.4, [MNa]$^+$=568.4

Example 13e (2R,4S)-N-Butyl-4-((4S,6R)-12-ethyl-6,16-dimethyl-2,13-dioxo-3,12-diaza-bicyclo[12.3.1]octadeca-1(18),14,16-trien-4-yl)-4-hydroxy-2-methyl-butyramide The title compound is obtained using N-allyl-5-methyl-N-ethyl-isophthalamic acid (Acid IVl) instead of 2-ethoxy-6-pent-4-enylamino-isonicotinic acid (Acid IIIh).

LC/MS (Nucleosil C-18HD, 4×70 mm, 3 μM, 20-100% MeCN (6 min), 100% MeCN (1.5 min)): 4.98 min; MS(ES) [MH]$^+$=502.4, [MNa]$^+$=524.4

Example 13f (2R,4S)-N-Butyl-4-((4S,6R)-12-ethyl-16-methanesulfonyl-6-methyl-2,13-dioxo-3,12-diaza-bicyclo [12.3.1]octadeca-1(18),14,16-trien-4-yl)-4-hydroxy-2-methyl-butyramide The title compound is obtained using N-allyl-N-ethyl-5-methanesulfonyl-isophthalamic acid (Acid IVm) instead of 2-ethoxy-6-pent-4-enylamino-isonicotinic acid (Acid IIIh).

LC/MS (Nucleosil C-18HD, 4×70 mm, 3 μM, 20-100% MeCN (6 min), 100% MeCN (1.5 min)): 4.49 min; MS(ES) [MH]$^+$=566.4

Example 13g (2R,4S)N-Butyl-4-((4S,6R)-12-ethyl-6-methyl-16-oxazol-2-yl-2,13-dioxo-3,12-diaza-bicyclo[12.3.1]octadeca-1(18),14,16-trien-4-yl)-4-hydroxy-2-methyl-butyramide The title compound is obtained using N-allyl-N-ethyl-5-oxazol-2-yl-isophthalamic acid (Acid IVn) instead of 2-ethoxy-6-pent-4-enylamino-isonicotinic acid (Acid IIIh).
LC/MS (Nucleosil C-18HD, 4×70 mm, 3 μM, 20-100% MeCN (6 min), 100% MeCN (1.5 min)): 4.82 min; MS(ES) [MH]$^+$=555.4

Example 13h (2R,4S)-N-Butyl-4-((4S,6R)-13-ethyl-6-methyl-2,14-dioxo-3,13-diaza-bicyclo[13.3.1]nonadeca-1(18),15(19),16-trien-4-yl)$_4$-hydroxy-2-methyl-butyramide The title compound is obtained using N-but-3-enyl-N-ethyl-isophthalamic acid (Acid IVo) instead of 2-ethoxy-6-pent-4-enylamino-isonicotinic acid (Acid IIIh).
LC/MS (Nucleosil C-18HD, 4×70 mm, 3 μM, 20-100% MeCN (6 min), 100% MeCN (1.5 min)): 4.90 min; MS(ES) [MH]$^+$=502.4, [MNa]$^+$=524.4

Example 13i (2R,4S)-N-Butyl-4-hydroxy-2-methyl-4-((4S,6R)-6-methyl-2,14-dioxo-13-propyl-3,13-diaza-bicyclo[13.3.1]nonadeca-1(18),15(19),16-trien-4-yl)-butyramide The title compound is obtained using N-but-3-enyl-N-propyl-isophthalamic acid (Acid IVp) instead of 2-ethoxy-6-pent-4-enylamino-isonicotnic acid (Acid IIIh).
LC/MS (Nucleosil C-18HD, 4×70 mm, 3 μM, 20-100% MeCN (6 min), 100% MeCN (1.5 min)): 5.27 min; MS(ES) [MH]$^+$=516.4, [MNa]$^+$=538.4

Example 14

(2R,4S)-N-Butyl-4-((10R,12S)-2,10-dimethyl-1,1,14-trioxo-1lambda*6*-thia-2,13-diaza-cyclohexadec-12-yl)-4-hydroxy-2-methyl-butyramide The title compound is obtained similarly to Example 11 as a single diastereomer, using 3-(methyl-pent-4-enyl-sulfamoyl)propionic acid (Acid Va) instead of 2-but-3-enylamino-6-methoxy-isonicotinic acid in step c and using diastereomerically pure [(1S,3R)-3,7-dimethyl-1-((S)-5-oxo-2,5-dihydro-furan-2-yl)-oct-6-enyl]-carbamic acid tert-butyl ester in step c.
LC/MS (Nucleosil C-18HD, 4×70 mm, 3 μM, 20-100% MeCN (6 min), 100% MeCN (1.5 min)): 4.66 min; MS(ES) [MNa]$^+$=512.4

The following compound can be prepared via a similar procedure:

Example 14a (2R,4S)-4-Hydroxy-2-methyl-N-(3-methyl-butyl)-4-((7S,9R)-9-methyl-2,5-dioxo-1,6-diaza-cyclopentadec-7-yl)-butyramide The title compound is obtained using N-but-3-enyl-succinamic acid (Acid Vb) instead of 2-ethoxy-6-pent-4-enylamino-isonicotinic acid (Acid IIIh).
LC/MS (Nucleosil C-18HD, 4×70 mm, 3 μM, 20-100% MeCN (6 min), 100% MeCN (1.5 min)): 4.15 min; MS(ES) [MNa]$^+$=462.4

Example 15

(2R,4S)-N-Butyl-4-((5S,8S,10R)-5,10-dimethyl-3,3,6-trioxo-3lambda*6*-thia-7-aza-bicyclo[11.3.1]heptadeca-1(17),13,15-trien-8-yl)-4-hydroxy-2-methyl-butyramide The title compound is obtained in a similar manner as Example 10, starting from (5S,8S,10S)-5,10-dimethyl-8-((2S,4R)-4-methyl-5-oxo-tetrahydro-furan-2-yl)-3,3-dioxo-3lambda*6*-thia-7-aza-bicyclo[11.3.1]heptadeca-1(17),11,13,15-tetraen-6-one instead of [(R)-3-Methyl-1-(4-methyl-5-oxo-tetrahydro-furan-2-yl)-hept-6-enyl]-carbamic acid tert-butyl ester (mixture of diastereomers, Example 6, step f) in step c.
LC/MS (Nucleosil C-18HD, 4×70 mm, 3 μM, 20-100% MeCN (6 min), 100% MeCN (1.5 min)): 4.34 min; MS(ES) [MNa]$^+$=517.2

The starting material can be prepared as follows:

a) (5S,8S,10S)-5,10-Dimethyl-8-((2S,4R)-4-methyl-5-oxo-tetrahydro-furan-2-yl)-3,3-dioxo-3lambda*6*-thia-7-aza-bicyclo[11.3.1]heptadeca-1(17),11,13,15-tetraen-6-one The title compound is prepared following the procedure described for step b of example 10.
LC/MS (Nucleosil C-18HD, 4×70 mm, 3 μM, 20-100% MeCN (6 min), 100% MeCN (1.5 min)): 4.45 min; MS(ES) [MNa]$^+$=442.2 b) (S)-2-Methyl-N-[(1S,3S)-3-methyl-1-((2S,4R)-4-methyl-5-oxo-tetrahydro-furan-2-yl)-pent-4-enyl]-3-(3-vinyl-phenylmethanesulfonyl)-propionamide The title compound is prepared following the procedure described for step c of example 10 using (S)-2-methyl-3-(3-vinyl-phenylmethanesulfonyl)-propionic acid (Acid IIi) instead of (S)-3-(hex-5-ene-1-sulfonyl)-2-methyl-propionic acid (Acid IIa).
LC/MS (Nucleosil C-18HD, 4×70 mm, 3 μM, 20-100% MeCN (6 min), 100% MeCN (1.5 min)): 5.15 min; MS(ES) [MNa]$^+$=470.2 c) [(S)-3-Methyl-1-(4-methyl-5-oxo-tetrahydro-furan-2-yl)-pent-4-enyl]-carbamic acid tert-butyl ester The title compound is prepared following the procedure described for step e of example 6.
LC/MS (Nucleosil C-18HD, 4×70 mm, 3 μM, 20-100% MeCN (6 min), 100% MeCN (1.5 min)): 4.09 min; MS(ES) [MNa]$^+$=320.2 d) [(S)-3-Methyl-1-(5-oxo-tetrahydro-furan-2-yl)-pent-4-enyl]-carbamic acid tert-butyl ester A mixture of 2.19 g (6.67 mmol) (R)-6-tert-butoxycarbonylamino-4-methyl-6-(5-oxo-tetra-hydro-furan-2-yl)-hexanoic acid, 0.293 g (1.46 mmol) copper(II)acetate monohydrate, 0.2 ml pyridine and 5.4 g (12.0 mmol) Pb(OAc)$_4$ in 45 ml benzene is refluxed under nitrogen for 18 h. The mixture is cooled to rt, water is added and the organic phase is washed with water and 5% aqueous NaHCO$_3$. The organic phase is dried with Na$_2$SO$_4$, filtered and evaporated. The residue is purified by chromatography on silica gel (EtOAc/hexane 1:6 and 1:4) to yield the title compound.

LC/MS (Nucleosil C-18HD, 4×70 mm, 3 µM, 20-100% MeCN (6 min), 100% MeCN (1.5 min)): 3.60 min; MS(ES) [MNa]$^+$=306.2 e) (R)-6-tert-Butoxycarbonylamino-4-methyl-6-(5-oxo-tetrahydro-furan-2-yl)-hexanoic acid A mixture of 2.09 g (6.67 mmol) [(R)-3-Methyl-6-oxo-1-(5-oxo-tetrahydro-furan-2-yl)-hexyl]-carbamic acid tert-butyl ester, 1.2 g (10 mol) NaH$_2$PO$_4$, 50 ml tBuOH and 10 ml water is subsequently treated with 20 ml of a 2M THF solution of 2-methyl-2-butene and 2.35 g (20.6 mmol) NaClO$_2$ (technical, 80%). After stirring for 10 min the mixture is diluted with EtOAc and brine. The organic phase is dried with MgSO$_4$, filtered and evaporated to yield the title compound as a resin which is used in the next step without purification.

LC/MS (Nucleosil C-18HD, 4×70 mm, 3 µM, 20-100% MeCN (6 min), 100% MeCN (1.5 min)): 3.71 min; MS(ES) [MNa]$^+$=352.2 f) [(R)-3-Methyl-6-oxo-1-(5-oxo-tetrahydro-furan-2-yl)-hexyl]-carbamic acid tert-butyl ester A solution of 5.4 g (15.9 mmol) of [(R)-3,7-dimethyl-1-(5-oxo-tetrahydro-furan-2-yl)oct-6-enyl]-carbamic acid tert-butyl ester (preparation of aldehyde in step g of example 6) in a mixture 200 ml DCM and 10 ml MeOH is cooled to –70° C. After addition of 0.63 g (7.5 mmol) NaHCO$_3$ a stream of O$_3$ in O$_2$ is passed through the stirred mixture till a blue color persists. The excess ozone is removed by passing through more oxygen. After addition of 5.0 g (19 mmol) triphenylphosphine the mixture is allowed to warm up at rt and stirred for 4 h. The mixture is filtered and concentrated in vacuo. Chromatography on silica gel (EtOAc/Hexane 1:1) gives the title aldehyde.

LC/MS (Nucleosil C-18HD, 4×70 mm, 3 µM, 20-100% MeCN (6 min), 100% MeCN (1.5 min)): 4.14 min; MS(ES) [MNa]$^+$=336.2

The following compound can be prepared via a similar procedure:

Example 15a (2R,4S)-N-Butyl-4-hydroxy-2-methyl-4-((5S,8S,10R)-5,10,15-trimethyl-3,3,6-trioxo-3lambda*6*-thia-7-aza-bicyclo[11.3.1]heptadeca-1 (17),13,15-trien-8-yl)-butyramide The title compound can be obtained by using (S)-2-methyl-3-(3-methyl-5-vinyl-phenyl-methane-sulfonyl)-propionic acid (Acid IIi) instead of (S)-2-methyl-3-(3-vinyl-phenyl-methane-sulfonyl)-propionic acid (Acid IIj).

Rf: (DCM/methanol=95:5) 0.36
MS(LC/MS): [MNa]$^+$=531
1H-NMR (400 MHz, CDCl$_3$): 7.09 (s, 1H), 7.03 (s, 1H), 6.92 (s, 1H), 6.03 (d, 1H), 5.75 (t, 1H), 4.31 (d, 1H), 4.16 (d, 1H), 4.15-4.05 (m, 1H), 3.90 (t, 1H), 3.68 (t, 1H), 3.43-3.20 (m, 2H), 3.06 (dd, 1H), 2.83-2.50 (m, 4H), 2.87 (s, 3H), 1.82 (t, 1H), 1.65-1.0 (m, 11H), 1.48 (d, 3H), 1.22 (d, 3H), 0.95 (t, 3H), 0.88 (d, 3H)

Example 16

(2R,4S)-N-Butyl-4-((9S,12S,14R)-9,14-dimethyl-7,10-dioxo-6,7,8,9,10,11,12, 13,14,15,16,17-dodecahydro-5-oxa-8,11-diaza-benzocyclopentadecen-12-yl)-4-hydroxy-2-methyl-butyramide The title compound is prepared similarly to Example 6, using (2-allyl-phenoxy)-acetic acid instead of (2S)tert-butoxycarbonyl-2-amino-6-heptenoic acid in step c and starting from [(S)-3-methyl-1-(4-methyl-5-oxo-tetrahydro-furan-2-yl)-pent-4-enyl]-carbamic acid tert-butyl ester (example 15, step d) instead of {(S)-1-[(1S,3R)-3-methyl-1-((2S,4R)-4-methyl-5-oxo tetrahydro-furan-2-yl)-hept-6-enylcarbamoyl]-ethyl}-carbamic acid tert-butyl ester in step d.

LC/MS (Nucleosil C-18HD, 4×70 mm, 3 µM, 20-100% MeCN (6 min), 100% MeCN (1.5 min)): 4.78 min; MS(ES) [MNa]$^+$=512.4

Example 17

(2R,4S)-N-Butyl-4-((5S,8S,10R)-5,10-dimethyl-3,3,6-trioxo-3lambda*6*-thia-7-aza-bicyclo[12.3.1]octa-deca-1(18),14,16-trien-8-yl)-4-hydroxy-2-methyl-butyramide The title compound is obtained in a similar manner as Example 10, starting from [(R)-3-methyl-1-(5-oxo-2,5-dihydro-furan-2-yl)-hex-5-enyl]-carbamic acid tert-butyl ester (mixture of diastereomers, step c of example 7) instead of [(R)-3-methyl-1-(4-methyl-5-oxo-tetrahydro-furan-2-yl)-hept-6-enyl]-carbamic acid tert-butyl ester (mixture of diastereomers, step f of example 6) in step c.

Rf: (DCM/methanol=95:5) 0.35
MS (LC/MS): [MNa]$^+$=531

Building Blocks

Acids I

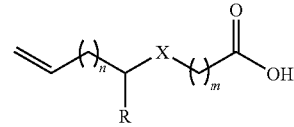

R=H, Me, Et, Pr
X=bond, —O—, —NCbz, —NBn
n=1-4
m=1-4 a) 3-(Allyl-benzyloxycarbonyl-amino)-propionic acid

To a solution of 2.5 g (11.2 mmol) 3-benzyloxycarbonylamino-propionic acid in 30 ml DMF and 30 ml THF are added 1.34 g (33.6 mmol, 60% suspension in mineral oil) NaH and the mixture is heated at 60° C. for 3 h. After cooling down 1.42 ml (16.8 mmol) allyl bromide are added. After stirring for 40 h at rt the mixture is diluted with 10% citric acid and extracted three times with EtOAc. The combined organic layers are washed with water, dried with sodium sulfate and the volatiles are removed in vacuo. The residue is chromatographed on silica gel (hexane/EtOAc 3:1), yielding the title product.

1H-NMR (400 MHz, CDCl$_3$): 7.41-7.30 (m, 5H); 5.88-5.74 (m, 1H), 5.27-5.12 (m, 4H), 4.02-3.93 (m, 2H), 3.63-3.53 (m, 2H), 2.75-2.61 (m, 2H)

LC/MS (Nucleosil C-18HD, 4×70 mm, 3 μM, 20-100% MeCN (6 min), 100% MeCN (1.5 min)): 4.13 min; MS(ES) [MNa]$^+$=286.2 b) (R)-4-Methyl-hept-6-enoic acid

This compound is prepared analogously to its known mirror image (S)-4-methyl-hept-6-enoic acid.

c) (2-methyl-but-3-enyloxy)-acetic acid

Under nitrogen atmosphere a suspension of 0.5 g (5.81 mmol) 2-methyl-3-buten-1-ol and 0.348 g (8.71 mmol, 60% suspension in mineral oil) NaH in 10 ml THF are stirred 3 h at rt. Solid sodium iodo acetate (1.81 g, 8.71 mmol) is added and stirring is continued for 2 h. The mixture is diluted with water and brine, acidified with 1N HCl and extracted with EtOAc. The organic phase is dried with sodium sulfate and concentrated. the residue is kugelrohr distilled at ca 1 mbar (70-110° C.) to yield the title compound as a colorless liquid.

1H-NMR (400 MHz, CDCl$_3$): 5.85-5.76 (m, 1H), 5.16-5.05 (m, 2H), 4.17 (s, 2H), 3.53-3.42 (m, 2H), 2.60-2.50 (m, 1H), 1.07 (d, 3H)

MS(neg) [M−H]$^-$ 143.1 d) (1-Ethyl-but-3-enyloxy)-acetic acid

The title compound is obtained by a similar procedure as Ic from hex-5-en-3-ol instead of 2-methyl-3-buten-1-ol.

MS(neg) [M−H]$^-$ 157 e) (1-Propyl-pent-4-enyloxy)-acetic acid

The title compound is obtained by a similar procedure as Ic from oct-7-en-4-ol instead of 2-methyl-3-buten-1-ol.

MS(neg) [M−H]$^-$ 185 f (Benzyl-pent-4-enyl-amino)-acetic acid

The title compound is obtained by sodium hydroxide saponification of the corresponding methyl ester and used as its sodium salt.

Acids II

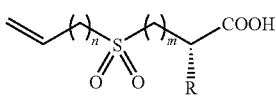

R=H, Me a) (S)-3-(hex-5-ene-1-sulfonyl)-2-methyl-propionic acid example 3 example 10, step c A solution of 1.62 g (10 mmol) (S)-3-acetylsulfanyl-2-methyl-propionic acid in 20 ml MeOH is treated with 7.5 ml 4N NaOH and 1.63 g (10 mmol) 6-bromo-hex-1-ene. After being stirred for 1 h at rt the mixture is diluted with 50 ml EtOAc and acidified with 25 ml 1N HCl. The organic phase is washed with brine, dried with sodium sulfate and concentrated in vacuo to yield (S)-3-hex-5-enylsulfanyl-2-methyl-propionic acid as an oil which is used without purification for the next step.

LC/MS (Nucleosil C-18HD, 4×70 mm, 3 μM, 20-100% MeCN (6 min), 100% MeCN (1.5 min)): 5.03 min; MS(ES) [MNa$_2$-H]$^+$=247

The product is dissolved in 20 ml MeOH and 10 ml water, cooled at +4° C. and treated with 7.35 g (22 mmol) oxone®. The mixture is stirred at rt for 18 h, diluted with 20 ml 1N HCl and extracted with EtOAc (3×). The combined organic phases are dried with sodium sulfate, evaporated and crystallized from TBME/hexane to yield the title compound as a white powder.

Mp 51-54° C.

LC/MS (Nucleosil C-18HD, 4×70 mm, 3 μM, 20-100% MeCN (6 min), 100% MeCN (1.5 min)): 3.58 min; MS(ES) [MNa]$^+$=257 b) (S)-2-Methyl-3-(pent-4-ene-1-sulfonyl)-propionic acid example 3a

The title compound is obtained by a similar procedure as IIa using 5-bromo-pent-1-ene instead 6-bromo-hex-1-ene.

1H-NMR (400 MHz, CDCl$_3$): 5.84-5.74 (m, 1H), 5.14-5.09 (m, 2H), 3.63-3.58 (m, 1H), 3.29-3.20 (m, 1H), 3.06-2.98 (m, 3H), 2.28-2.23 (m, 2H), 2.04-1.96 (m, 2H), 1.49 (d, 3H)

LC/MS (Nucleosil C-18HD, 4×70 mm, 3 μM, 20-100% MeCN (6 min), 100% MeCN (1.5 min)): 2.91 min; MS(ES) [MNa]$^+$=243 c) 2-Methyl-3-(pent-4-ene-1-sulfonyl)-propionic acid example 10a

The title compound is obtained by a similar procedure as IIa using 5-bromo-pent-1-ene instead 6-bromo-hex-1-ene and racemic 3-acetylsulfanyl-2-methyl-propionic acid instead of (S)-3-acetylsulfanyl-2-methyl-propionic acid.

d) (S)-3-(But-3-ene-1-sulfonyl)-2-methyl-propionic acid example 10b

The title compound is obtained by a similar procedure as IIa using 4-bromo-but-1-ene instead of 6-bromo-hex-1-ene.

1H-NMR (400 MHz, CDCl3): 5.91-5.81 (m, 1H), 5.23-5.16 (m, 2H), 3.66-3.60 (m, 1H), 3.63 (dd, 1H), 3.15-3.11 (m, 2H), 3.02 (dd, 1H), 2.68-2.62 (m, 2H), 1.49 (d, 3H)

LC/MS (Nucleosil C-18HD, 4×70 mm, 3 μM, 5-100% MeCN (6 min), 100% MeCN (1.5 min)): 3.47 min; MS(ES) [MNa]$^+$=229.0 e) (S)-3-(Hept-6-ene-1-sulfonyl)-2-methyl-propionic acid example 10c

The title compound can be obtained by a similar procedure as IIa using toluene-4-sulfonic acid hept-6-enyl ester instead of 6-bromo-hex-1-ene.

f) (Hept-6-ene-1-sulfonyl)-acetic acid example 10d

The title compound can be obtained by a similar procedure as IIa using toluene-4-sulfonic acid hept-6-enyl ester instead of 6-bromo-hex-1-ene and mercapto-acetic acid instead of (S)-3-acetylsulfanyl-2-methyl-propionic acid.

g) 3-(Hex-5-ene-1-sulfonyl)-propionic acid example 10e

The title compound can be obtained by a similar procedure as IIa using 3-mercapto-propionic acid instead of (S)-3-acetylsulfanyl-2-methyl-propionic acid.

1H-NMR (400 MHz, CDCl$_3$): 5.86-5.76 (m, 1H), 5.10-5.01 (m, 2H), 3.33 (t, 2H), 3.08-3.01 (m, 2H), 2.98 (t, 2H), 2.18-2.10 (m, 2H), 2.94-2.87 (m, 2H), 1.63-1.55 (m, 2H)

h) 4-(Pent-4-ene-1-sulfonyl)-butyric acid example 10f

An ice cold solution of 0.584 g (6.66 mmol) 4-penten-1-ol and 1.11 ml (14.0 mmol) pyridine in 5 ml DCM is treated with 0.866 ml (6.77 mmol) benzene sulfonyl chloride. After 30 minutes at 0° C. the mixture is stirred overnight at rt. The mixture is diluted with DCM, washed with 5% aqueous citric acid, water and 5% aqueous NaHCO3, dried with sodium sulfate and evaporated, yielding the benzenesulfonic acid pent-4-enyl ester as a colorless oil that is used without further purification.

1H-NMR (400 MHz, CDCl$_3$): 7.97-7.92 (m, 2H), 7.72-7.66 (m, 1H), 7.63-7.56 (m, 2H), 5.76-5.66 (m, 1H), 5.01-4.95 (m, 2H), 4.08 (t, 2H), 2.11 (q, 2H), 1.79 (quintet, 2H)

A mixture of this ester (1.11 g, 4.89 mmol), 0.5 g (4.89 mmol) thiobutyrolactone and 2.45 ml (9.78 mmol) 4N NaOH is stirred for 7 days. The mixture is acidified with 3.5 ml 4N HCl and extracted with EtOAc. The organic phase is dried with sodium sulfate and chromatographed on silica gel (EtOAc/hexane 1:3, 1:2 and 1:1), yielding the 4-pent-enyl-sulfanyl-butyric acid as a colorless oil.

1H-NMR (300 MHz, CDCl$_3$): 5.84-5.69 (m, 1H), 5.06-4.93 (m, 2H), 2.60-2.44 (m, 6H), 2.20-2.11 (m, 2H), 1.97-1.84 (m, 2H), 1.72-1.60 (m, 2H)

This acid is dissolved in 20 ml MeOH and 10 ml water, cooled at +4° C. and treated with 3.52 g (10.84 mmol) oxone®. The mixture is stirred 1 h at 0° C. and 18 h at rt. The mixture is diluted with 10 ml 1N HCl and extracted with EtOAc. The organic phase is washed with aqueous sodium sulfite, dried with sodium sulfate, evaporated and crystallized from EtOAc/hexane to yield the title compound as a white powder.

Mp 104-107° C.

1H-NMR (300 MHz, CDCl$_3$): 5.81-5.67 (m, 1H), 5.10-5.02 (m, 2H), 3.10-3.03 (m, 2H), 3.01-2.94 (m, 2H), 2.61 (t, 2H), 2.27-2.10 (m, 4H), 2.01-1.89 (m, 2H)

i) (S)-2-Methyl-3-(3-vinyl-phenylmethanesulfonyl)-propionic acid example 15

A mixture of 1.84 g (5 mmol), 5 ml 1N NaOH, 1.38 g (10 mmol) K$_2$CO$_3$ and 0.072 mg Pd(PPh$_3$)$_4$ (0.25 mmol) in 5 ml water and 50 ml DME is heated at 80° C. under nitrogen. After cooling down the mixture is acidified with 20 ml 2N HCl and extracted with 150 ml TBME. The organic phase is dried with Na$_2$SO$_4$, filtered and evaporated to yield the title compound that is used in the next step without purification.

LC (Nucleosil C-18HD, 4×70 mm, 3 μM, 20-100% MeCN (6 min), 100% MeCN (1.5 min)): 3.75 min; MS(API-ES) [M−H]$^-$=267.0

The starting material can be prepared as follows:

1) (S)-3-(3-Iodo-phenylmethanesulfonyl)-2-methyl-propionic acid

The title compound is prepared similarly to (S)-3-(hex-5-ene-1-sulfonyl)-2-methyl-propionic acid (IIa), but starting from (S)-3-(3-iodo-benzylsulfanyl)-2-methyl-propionic acid instead of (S)-3-hex-5-enylsulfanyl-2-methyl-propionic acid.

LC (Nucleosil C-18HD, 4×70 mm, 3 μM, 20-100% MeCN (6 min), 100% MeCN (1.5 min)): 3.97 min; MS(API-ES) [M−H]$^-$=367.0

2) (S)-3-(3-Iodo-benzylsulfanyl)-2-methyl-propionic acid

The title compound is prepared similarly to (S)-3-hex-5-enylsulfanyl-2-methyl-propionic acid (IIa), using 1-bromomethyl-3-iodo-benzene instead of 6-bromo-hex-1-ene.

LC (Nucleosil C-18HD, 4×70 mm, 3 μM, 20-100% MeCN (6 min), 100% MeCN (1.5 min)): 5.11 min; MS(API-ES) [M−H]$^-$=335.0 j) (S)-2-Methyl-3-(3-methyl-5-vinyl-phenylmethanesulfonyl)-propionic acid example 15a Potassium vinyltrifluoroborate (247 mg, 1.8 mmol), triethylamine (0.21 ml, 1.5 mmol) and [1,1'-bis(diphenylphosphino-κP)ferrocene]dichloro-palladium (24 mg) are added to (S)-3-(3-bromo-5-methyl-phenylmethanesulfonyl)-2-methyl-propionic acid (0.5 g, 1.5 mmol) in 25 ml propanol. The mixture is stirred under argon for 2.5 hrs at reflux. After cooling to rt the mixture is diluted with EtOAc, washed with 0.5 N aqueous hydrochloric acid and brine, dried over magnesium sulfate, and the solvents are evaporated. The residue is purified by chromatography on silica gel (flashmaster, DCM to DCM/methanol 9/1) followed by crystallization from DCM/diethyl ether/hexane to give the title compound as off-white crystals.

Rf: (DCM/methanol=9:1) 0.45

MS (LC-MS): [MNa]$^+$=305

The starting material can be prepared as described hereafter:

x) (S)-3-(3-Bromo-5-methyl-phenylmethanesulfonyl)-2-methyl-propionic acid

To a solution of 6.48 g (21 mmol) (S)-3(3-bromo-5-methyl-benzylsulfanyl)-2-methyl-propionic acid in 70 ml acetonitrile and 35 ml water is added 65.7 g (107 mmol) oxone®. After stirring for 2.5 hrs at rt the mixture is diluted with EtOAc and water to get a clear solution. The organic layer is washed with brine, dried over magnesium sulfate and the solvent is evaporated. Crystallization from DCM/diethyl ether and a little methanol gives the title compound as white crystals.

Rf: (DCM/methanol=95:5) 0.34

MS (LC-MS): [MNa]$^+$=357/359 xx) 1-Bromo-3-bromomethyl-5-methyl-benzene

To a solution of 5 ml (36.8 mmol) 5-bromo-m-xylene and 6.55 g (36.8 mmol) N-bromo-succinimide in 35 ml tetrachloromethane is added 0.138 ml (0.74 mmol) tert-butyl-perbenzoate. The mixture is irradiated using a heating lamp and stirred for 3 hrs at reflux temperature. The mixture is cooled to room temperature, filtered and evaporated. The product is isolated by chromatography on silica gel (flashmaster, hexane) to give the title compound as white crystals.

Rf: (hexane) 0.38

MS (EI-MS): 262/264/266 [M+, characteristic pattern for tribromo compound]

xxx) (S)-3-(3-Bromo-5-methyl-benzylsulfanyl)-2-methyl-propionic acid

A solution of 5.55 g (21 mmol) 1-bromo-3-bromomethyl-5-methyl-benzene and 2.90 ml (21 mmol) (S)-3-acetylsulfanyl-2-methyl-propionic acid in 32 ml methanol is cooled in an ice bath and 4N aqueous sodium hydroxide (15.8 ml, 63 mmol) are added. The reaction mixture is stirred at rt for 3 hrs. EtOAc is added to the mixture and the organic layer is washed with water and brine and evaporated. Filtration over silica gel (flashmaster, hexane to hexane/EtOAc 4/6) gives the title compound.

Rf: (hexane/EtOAc=7/3) 0.36

1H-NMR (400 MHz, CDCl$_3$): 7.30 (s, 1H), 7.25 (s, 1H), 7.08 (s, 1H), 3.68 (s, 2H), 2.79 (dd, 1H), 2.74-2.65 (m, 1H), 2.52 (dd, 1H), 2.35 (s, 3H), 1.30 (d, 3H)

Acids III $R_1$=Allyl, But-3-enyl, Pent-4-enyl
Y=O, NH, NMe, SO$_2$
X=H, Me, OMe, OEt

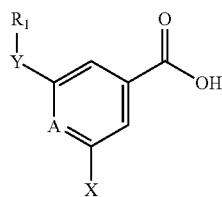

a) 2-But-3-enylamino-6-methyl-isonicotinic acid examples 5 and 13a

A solution of 86 mg (0.33 mmol) 2-but-3-enylamino-6-methyl-isonicotinic acid tert-butyl ester in 2 ml TFA is stirred for 18 h and evaporated. The title compound thus obtained is used in the next step without further purification.

1H-NMR (300 MHz, CDCl$_3$): 7.20 (s, 1H), 7.00 (s, 1H), 5.87-5.71 (m, 1H), 5.21-5.10 (m, 2H), 3.42 (t, 2H), 2.58 (s, 3H), 2.47 (q, 2H)

LC (Nucleosil C-18HD, 4×70 mm, 3 μM, 20-100% MeCN (6 min), 100% MeCN (1.5 min)): 1.23 min. MS(ES) [MH]$^+$= 207.2

The starting material can be prepared as follows:

x) 2-But-3-enylamino-6-methyl-isonicotinic acid tert-butyl ester

Under rigorous exclusion of oxygen a mixture of 200 mg (0.88 mmol) 2-chloro-6-methyl-isonicotinic acid tert-butyl ester, 10 mg palladium(II)acetate (0.044 mmol), 27 mg (0.44 mol) BINAP (R(+)-2,2-bis(diphenylphosphino)-1,1-binaphtalene) and 62 mg (0.88 mmol) but-3-enylamine in 10 ml toluene is heated at 60° C. for 4 h. The mixture is diluted with EtOAc, washed with 10% aqueous NaHCO3 and water, dried with sodium sulfate and evaporated. Chromatography of the product on silica gel (hexane/EtOAc 9:1) yields the title compound.

1H-NMR (300 MHz, CDCl$_3$): 6.86 (s, 1H), 6.67 (s, 1H), 5.87-5.71 (m, 1H), 5.16-5.05 (m, 2H), 4.6 (br, 1H), 3.31 (q, 2H), 2.4-2.31 (m, 2H), 2.38 (s, 3H), 1.55 (s, 9H)

LC (Nucleosil C-18HD, 4×70 mm, 3 μM, 20-100% MeCN (6 min), 100% MeCN (1.5 min)): 3.75 min xx) 2-Chloro-6-methyl-isonicotinic acid tert-butyl ester A suspension of 0.2 g (1.17 mmol) 2-chloro-6-methyl-isonicotinic acid in 5 ml toluene is treated with 2 drops of DMF and 0.17 ml (2.33 mmol) SOCl2 and refluxed for 4 h. The mixture is concentrated under reduced pressure and the residue is taken up in 1.5 ml DCM, 0.22 ml tBuOH and 0.24 ml Et3N and stirred in the presence of 7 mg (0.06 mmol) DMAP for 18 h. The mixture is diluted with DCM, washed with 10% aqueous citric acid, water and 10% aqueous NaHCO3, dried with sodium sulfate and evaporated. Chromatography of the product on silica gel (hexane/EtOAc 4:1 and 3:1) yields the title compound as a yellowish solid.

1H-NMR (400 MHz, CDCl$_3$): 7.65 (s, 1H), 7.60 (s, 1H), 2.82 (s, 3H), 1.62 (s, 9H)

LC (Nucleosil C-18HD, 4×70 mm, 3 μM, 20-100% MeCN (6 min), 100% MeCN (1.5 min)): 5.83 min b) 2-But-3-enylamino-6-methoxy-isonicotinic acid step c of example 11

A mixture of 1.0 g (5.3 mmol) 2-chloro-6-methoxy-isonicotinic acid, 4.4 g (53 mmol, 86% pure by NMR) but-3-enylamine and 85 mg (0.53 mmol) CuSO$_4$ in 10 ml H$_2$O is stirred in a pressurized reaction vessel for 36 h at 140° C. The reaction mixture is diluted with an 0.5 M aqueous citric acid and extracted two times with EtOAc. The combined extracts are washed with citric acid solution, water and brine, dried over Na$_2$SO$_4$, filtered and the solvent is evaporated. Chromatography on silica gel yields the title compound as an off-white powder.

HPLC (XTerra 4.5 cm, 95% CH$_3$CN, 50° C.): 3.64 min. MS (LC/MS): [MH]$^+$=223.3 c) 3-(Benzyloxycarbonyl-but-3-enyl-amino)-5-methoxy-benzoic acid example 11a

A mixture of 0.75 g (2.38 mmol) 3-benzyloxycarbonylamino-5-methoxy-benzoic acid, 1.07 g (2.85 mmol) NaI, 2.3 g (7.14 mmol) Cs$_2$CO$_3$ and ca. 1 ml (10 mmol) 4-bromo-but-1-ene in 2 ml DMF is heated at 40° C. for 18 h. After cooling down the reaction mixture is diluted with TBME and washed with water. The organic phase is dried with sodium sulfate and evaporated. Purification of the crude product by chromatography on silica gel (hexane EtOAc 5:1) gives the 3-(benzyloxycarbonyl-but-3-enyl-amino)-5-methoxy-benzoic acid methyl ester.

LC (Nucleosil C-1 8HD, 4×70 mm, 3 μM, 20-100% MeCN (6 min), 100% MeCN (1.5 min)): 6.07 min. MS(ES) [MNa]$^+$= 392.2

This ester (118 mg, 0.32 mmol) is dissolved in 2 ml MeOH and treated with 2 ml 1N NaOH for 18 h. The mixture is acidified with 1 N HCl and extracted with EtOAc. The organic phase is dried with sodium sulfate and evaporated to yield the title compound.

LC (Nucleosil C-18HD, 4×70 mm, 3 μM, 20-100% MeCN (6 min), 100% MeCN (1.5 min)): 5.14 min. MS(ES) [MNa]$^+$= 378.2, [M−H+Na$_2$]$^+$=400.2 d) 3-Hex-5-enyloxy-benzoic acid example 11b

The title compound is prepared similarly to 3-(9-decenyloxy)benzoic acid in Lin, H-C et al Macromolecules 1998, 31, 7298.

1H-NMR (300 MHz, CDCl$_3$): 7.73-7.10 (m, 4H), 5.90-5.76 (m, 1H), 5.08-4.95 (m, 2H), 4.02 (t, 2H), 3.14 (q, 2H), 1.90-1.78 (m, 2H), 1.66-1.54 (m, 2H)

LC (Nucleosil C-18HD, 4×70 mm, 3 µM, 20-100% MeCN (6 min), 100% MeCN (1.5 min)): 5.33 min. MS(ES) [M−H+Na$_2$]$^+$=265.2 e) 3-But-3-enyloxy-benzoic acid example 11c

The title compound is prepared similarly to 3-(9-decenyloxy)benzoic acid in Lin, H-C et al Macromolecules 1998, 31, 7298.

1H-NMR (400 MHz, CDCl$_3$): 7.71 (d, 1H), 7.63-7.60 (m, 1H), 7.37 (t, 1H), 7.16 (dd, 1H), 5.97-5.87 (m, 1H), 5.22-5.12 (m, 2H), 4.09 (t, 2H), 2.61-2.56 (m, 2H)

LC (Nucleosil C-18HD, 4×70 mm, 3 µM, 20-100% MeCN (6 min), 100% MeCN (1.5 min)): 4.55 min. MS(ES) [MNa$_2$−H]$^+$=237.0 f) 3-Pent-4-enyloxy-benzoic acid example 11d

The title compound is prepared similarly to 3-(9-decenyloxy)benzoic acid in Lin, H-C et al Macromolecules 1998, 31, 7298.

1H-NMR (400 MHz, CDCl$_3$): 7.71 (d, 1H), 7.62 (s, 1H), 7.37 (t, 1H), 7.16 (d, 1H), 5.92-5.82 (m, 1H), 5.11-5.01 (m, 2H), 4.04 (t, 2H), 2.30-2.25 (m, 2H), 1.96-1.90 (m, 2H)

LC (Nucleosil C-18HD, 4×70 mm, 3 µM, 20-100% MeCN (6 min), 100% MeCN (1.5 min)): 5.00 min. MS(ES) [MNa$_2$−H]$^+$=251.0 g) 3-(But-3-ene-1-sulfonyl)-benzoic acid example 11m

The title compound is obtained by a similar procedure as IIa using 4-bromo-but-1-ene instead 6-bromo-hex-1-ene and 3-mercapto-benzoic acid instead of (S)-3-acetylsulfanyl-2-methyl-propionic acid.

1H-NMR (400 MHz, CDCl$_3$): 8.71 (s, 1H), 8.45 (d, 1H), 8.22 (d, 1H), 7.58 (t, 1H), 5.82-5.72 (m, 1H), 5.14-5.09 (m, 2H), 3.29-3.22 (m, 2H), 2.58-2.50 (m, 2H)

LC/MS (Nucleosil C-18HD, 4×70 mm, 3 µM, 20-100% MeCN (6 min), 100% MeCN (1.5 min)): 3.43 min; MS(ES) [MNa]$^+$=263.0 h) 2-Ethoxy-6-pent-4-enylamino-isonicotinic acid example 13

The title compound is prepared by stirring 2-ethoxy-6-pent-4-enylamino-isonicotinic acid tert-butyl ester 18 h in neat trifluoroacetic acid. Evaporation of the TFA gives the title compound that is used in the next step without purification.

The starting material can be prepared with methods described for examples IIIa and IIIb.

x) 2-Ethoxy-6-pent-4-enylamino-isonicotinic acid tert-butyl ester

1H-NMR (300 MHz, CDCl$_3$): 6.47 (s, 2H), 5.89-5.76 (m, 1H), 5.10-4.97 (m, 2H), 4.28 (q, 2H), 3.30 (t, 3H), 2.20 (q, 2H), 1.79-1.67 (m, 2H), 1.57 (s, 9H), 1.39 (t, 3H)

LC/MS (Nucleosil C-18HD, 4×70 mm, 3 µM, 20-100% MeCN (6 min), 100% MeCN (1.5 min)): 6.66 min; MS(API-ES) [M−H]$^−$=305.2 i) 2-(1-Ethyl-but-3-enylamino)-6-methoxy-isonicotinic acid example 13b

The title compound is prepared by stirring 2-ethoxy-6-pent-4-enylamino-isonicotinic acid tert-butyl ester 18 h in neat trifluoroacetic acid. Evaporation of the TFA gives the title compound that is used in the next step without purification.

The starting material can be prepared with methods described for examples IIIa and IIIb.

x) 2-(1-Ethyl-but-3-enylamino)-6-methoxy-isonicotinic acid tert-butyl ester 1H-NMR (400 MHz, CDCl$_3$): 6.49 (s, 2H), 5.91-5.80 (m, 1H), 5.16-5.08 (m, 2H), 4.4 (br, 1H), 3.89 (s, 3H), 3.85-3.76 (m, 1H), 2.42-2.29 (m, 2H), 1.72-1.51 (m, 2H), 1.58 (s, 9H), 0.99 (t, 3H)

LC/MS (Nucleosil C-18HD, 4×70 mm, 3 µM, 20-100% MeCN (6 min), 100% MeCN (1.5 min)): 6.64 min xx) 1-Ethyl-but-3-enylamine, hydrochloride

A stirred mixture of 23.4 g (149 mmol) (1-ethyl-but-3-enyl)-carbamic acid methyl ester, 33.4 g (0.6 mol) powdered KOH in 50 ml diethylene glycol is heated at 100° C. After the development of gas ceases the mixture is further heated at 118° C. for 1 hour while methanol is distilled off. After cooling down the mixture is diluted with water, extracted twice with TBME. The combined organic phases are washed with 10% aqueous NaCO3 solution, dried with K$_2$CO$_3$ and extracted with 75 ml 2N HCl. The aqueous phase is concentrated in vacuo and the residue crystallised from EtOAc/TBME to yield the title compound (hydrochloride salt).

H-NMR (400 MHz, D$_2$O): 5.76-5.64 (m, 1H), 5.18-5.11 (m, 2H), 3.19-3.11 (m, 1H), 2.42-2.33 (m, 1H), 2.25-2.16 (m, 1H), 1.64-1.47 (m, 2H), 0.86 (t, 3H)

xxx) (1-Ethyl-but-3-enyl)-carbamic acid methyl ester

To a cooled solution of 11.6 g (0.2 mol) propionaldehyde, 15 g (0.2 mol) carbamic acid methyl ester and 22.92 g allyl trimethyl silane in 200 ml acetonitrile are added dropwise 28.4 g (0.2 mol) boron trifluoride etherate. After the addition the mixture is neutralised with 10% aqueous Na$_2$CO$_3$ and extracted with EtOAc. The organic phase is washed with water, dried with sodium sulfate, evaporated and distilled at 1 mbar, yielding the title compound as a colorless liquid.

Bp: 59-61° C.

1H-NMR (400 MHz, CDCl$_3$): 5.86-5.74 (m, 1H), 5.14-5.08 (m, 2H), 4.5 (br, 1H), 3.76-3.63 (m, 1H), 3.70 (s, 3H), 2.23-2.17 (m, 2H), 1.63-1.51 (m, 1H), 1.47-1.38 (m, 1H), 0.95 (t, 3H)

Acids IV

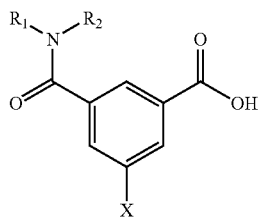

$R_1$=H, Me, Et, Pr, cPr
$R_2$=Allyl, But-3-enyl
X=H, Me, OMe, OEt, OiPr, $SO_2$Me, Oxazol-2-yl a) N-allyl-N-methyl-isophthalamic acid example 11e A solution of 2.5 g (13.9 mmol) isophthalic acid mono methyl ester in 25 ml THF, cooled at −30° C. is treated with 2.32 ml (16.9 mmol) $Et_3N$ followed by 2.0 ml (15.3 mmol) isobutyl chloroformate. After 30 min at −20° C. are added 1.4 ml (13.9 mmol) methyl allyl amine to the white suspension. After 4 h at −20° C. the mixture is poured into 50 ml water and extracted with EtOAc. The organic phase is washed with water, dried with $Na_2SO_4$ and evaporated. The residue is purified via chromatography on silica gel (EtOAc/hexane 1:2), yielding the methyl ester of the title compound. This ester is taken up in 5 ml MeOH and 5 ml 1N NaOH. After stirring for 2 h the mixture is acidified with 6 ml 1N HCl and extracted with EtOAc. The organic layer is dried with $Na_2SO_4$ and evaporated to yield the title compound as a white solid.

LC/MS (Nucleosil C-18HD, 4×70 mm, 3 μM, 20-100% MeCN (6 min), 100% MeCN (1.5 min)): 2.92 min; MS(ES) $[MNa]^+$=242.2 b) N-allyl-N-ethyl-isophthalamic acid example 11f

The title compound is obtained by a similar procedure as IVa using allyl-ethyl-amine instead of allyl-methyl-amine.
Mp. 118-121° C.
LC/MS (Nucleosil C-18HD, 4×70 mm, 3 μM, 20-100% MeCN (6 min), 100% MeCN (1.5 min)): 3.29 min; MS(ES) $MH^+$=234.2, $MNa^+$=256.2, $[M-H]Na_2^+$=278.2

The starting material can be obtained as follows:

x) Allyl ethyl amine hydrochloride

At 10° C. 28.9 g allyl-ethyl-carbamic acid tert-butyl ester (156 mmol) are dissolved in 200 ml 4N HCl in dioxane and slowly warmed to room temperature. When the development of gas has ceased the mixture is warmed at 30° C. for 1 h. The mixture is concentrated under reduced pressure and crystallized from EtOH/TBME to yield the hydrochloric acid salt of allyl ethyl amine as white plates.
Mp: 188.5-189° C.
1H-NMR (400 MHz, $D_2O$): 5.85-5.74 (m, 1H), 5.40-5.33 (m, 2H), 3.52 (d, 2H), 2.97 (q, 2H), 1.15 (t, 3H)

xx) Allyl-ethyl-carbamic acid tert-butyl ester

A solution of 31.44 g allyl-carbamic acid tert-butyl ester (200 mmol) in 300 ml DMF and 30 ml dry THF is treated with 12 g (300 mmol) NaH (60% suspension in mineral oil). The temperature is kept below 40° C. with an cold water bath. When the development of hydrogen gas ceased the reaction mixture is treated, under ice cooling, with 24 ml (300 mmol) ethyl iodide. After 16 h the mixture is diluted with 1 L water and extracted with TBME. The organic layer is washed extensively with water, concentrated under reduced pressure and distilled at 0.3 mmHg, bp. 38-39°, to yield the allyl-ethyl-carbamic acid tert-butyl ester.

Rf: (hexane/ethyl acetate 6:1) 0.45 1H-NMR (400 MHz, $CDCl_3$): 5.87-5.75 (m, 1H), 5.19-5.12 (m, 2H), 3.83 (br, 2H), 3.16 (br, 2H), 1.48 (s, 9H), 1.11 (t, 3H)

c) N-allyl-N-propyl-isophthalamic acid example 11g

The title compound is made using methods described for Acid IVb.
LC/MS (Nucleosil C-18HD, 4×70 mm, 3 μM, 20-100% MeCN (6 min), 100% MeCN (1.5 min)): 2.92 min; MS(ES) $[MH]^+$=248.2, $[MNa]^+$=270.2 d) N-allyl-N-cyclopropyl-isophthalamic acid example 11h

A solution of 0.3 g (1.37 mmol) N-cyclopropyl-isophthalamic acid in 10 ml THF is treated with 142 mg (3.55 mmol) NaH (60% suspension in mineral oil) and stirred at 25° C. After 2 h 0.27 ml (3.23 mmol) allylbromide is added and after 18 h the reaction is quenched with water. The mixture is acidified with 2N HCl and extracted with EtOAc. The organic phase is washed with brine, dried with sodium sulfate and evaporated to yield the title compound that is used in the next step without purification.

LC/MS (Nucleosil C-18HD, 4×70 mm, 3 μM, 20-100% MeCN (6 min), 100% MeCN (1.5 min)): 3.47 min; MS(ES) $MH^+$=246.2, $MNa^+$=268.2

The starting material can be prepared as follows:

x) N-cyclopropyl-isophthalamic acid

A solution of 0.5 g (2.77 mmol) isophthalic acid mono methyl ester, 5 ml toluene and 0.8 ml $SOCl2$ is treated with one drop DMF and heated to 80° C. till the evolution of gas ceases. After cooling down the mixture is evaporated, dissolved in 2 ml DCM and added to an at 0° C. stirred mixture of 5 ml 10% aqueous $Na_2CO_3$, 0.21 ml (3.0 mmol) cyclopropyl amine and 5 ml DCM. After 1 h the layers are separated and the organic layer is washed with 1 N HCl, brine, dried with sodium sulfate and evaporated. The crude product is crystallized (EtOAc, hexane) to yield N-cyclopropyl-isophthalamic acid methyl ester as off-white crystals.

$^1$H-NMR (400 MHz, $CDCl_3$): 8.33 (s, 1H), 8.18 (d, 1H), 8.05 (d, 1H), 7.55 (t, 1H), 6.41 (br, 1H), 3.97 (s, 3H), 3.00-2.91 (m, 1H), 0.98-0.85 (m, 2H), 0.75-0.62 (m, 2H)

e) N-allyl-N-methyl-5-methoxy-isophthalamic acid example 11i

The title compound is made using methods described for Acid IVb.
LC/MS (Nucleosil C-18HD, 4×70 mm, 3 μM, 20-100% MeCN (6 min), 100% MeCN (1.5 min)): 3.15 min; MS(ES) $[MH]^+$=250.0, $[MNa]^+$=272.0 f) N-allyl-N-ethyl-5-methoxy-isophthalamic acid example 11j

The title compound is made using methods described for Acid IVb.
LC/MS (Nucleosil C-18HD, 4×70 mm, 3 μM, 20-100% MeCN (6 min), 100% MeCN (1.5 min)): 3.55 min; MS(ES) [MH]$^+$=264.2, [MNa]$^+$=286.2 g) N-allyl-N-propyl-5-methoxy-isophthalamic acid example 11k

The title compound is made using methods described for Acid IVb.
LC/MS (Nucleosil C-18HD, 4×70 mm, 3 μM, 20-100% MeCN (6 min), 100% MeCN (1.5 min)): 3.97 min; MS(ES) [MH]$^+$=278.2, [MNa]$^+$=300.2 h) N-but-3-enyl-isophthalamic acid example 11l

The title compound is made using methods described for Acid IVa.
LC/MS (Nucleosil C-18HD, 4×70 mm, 3 μM, 20-100% MeCN (6 min), 100% MeCN (1.5 min)): 2.99 min; MS(ES) [MH]$^+$=220.2, [MNa]$^+$=242.2 i) N-allyloxy-N-ethyl-isophthalamic acid example 12a

The title compound is made using methods described for Acids IVb, IVc and IVj.
LC/MS (Nucleosil C-18HD, 4×70 mm, 3 μM, 20-100% MeCN (6 min), 100% MeCN (1.5 min)): 4.10 min; MS(ES) [MH]$^+$=294.2, [MNa]$^+$=316.2, [MNa$_2$–H]$^+$=338.2 j) N-Allyl-N-ethyl-5-ethoxy-isophthalamic acid example 13c

A solution of 1.0 g (4.45 mmol) 5-ethoxy-isophthalic acid mono methyl ester, 10 ml toluene and 0.5 ml SOCl2 is treated with one drop DMF and heated to 80° C. till the evolution of gas ceases. After cooling down the mixture is evaporated, dissolved in 5 ml DCM and added to an at 0° C. stirred mixture of 10 ml 10% aqueous Na$_2$CO$_3$, 0.81 g (6.7 mmol) allyl ethyl amine hydrochloride (see IVb) and 5 ml DCM. After 1 h the layers are separated and the organic layer is washed with 1N HCl, brine, dried with sodium sulfate and evaporated to yield the N-allyl-5-ethoxy-N-ethyl-isophthalamic acid methyl ester. This ester is dissolved in 20 ml MeOH, treated with 15 ml 1N NaOH and stirred for 18 h. The methanol is evaporated, the residue acidified with 1N HCl and extracted with TBME. The organic layer is dried with sodium sulfate and evaporated to yield the title compound.
LC/MS (Nucleosil C-18HD, 4×70 mm, 3 μM, 20-100% MeCN (6 min), 100% MeCN (1.5 min)): 3.95 min; MS(ES) [MH]$^+$=278.2, [MNa]$^+$=300.2
The starting material can be obtained as follows:

x) 5-Ethoxy-isophthalic acid mono methyl ester

A suspension of 11.0 g (46.1 mmol) 5-ethoxy-isophthalic acid dimethyl ester in 100 ml MeOH and 20 ml THF is treated with 18.4 ml 2N NaOH and stirred overnight. The clear solution is concentrated, diluted with some water and washed with TBME. The aqueous phase is acidified with 2N HCl and extracted with TBME. The organic phase is dried with sodium sulfate and evaporated to give the mono ester.
$^1$H-NMR (400 MHz, CDCl$_3$): 8.38 (s, 1H), 7.84 (s, 2H), 4.18 (q, 2H), 3.98 (s, 3H), 1.37 (t, 3H)

xx) 5-Ethoxy-isophthalic acid dimethyl ester

To a suspension of 10 g (47.57 mmol) 5-hydroxy-isophthalic acid dimethyl ester and 9.86 g (71.36 mmol) K$_2$CO$_3$ in 50 ml DMF is added dropwise 7.67 ml (95.1 mmol) ethyl iodide. After the addition the mixture is stirred for 5 h, diluted with water and extracted with TBME. The organic phase is washed with water, dried with sodium sulfate and evaporated to give the title compound.
$^1$H-NMR (400 MHz, CDCl$_3$): 8.29 (s, 1H), 7.77 (s, 2H), 4.15 (q, 2H), 3.95 (s, 6H), 1.47 (t, 3H)

k) N-Allyl-N-ethyl-5-isopropoxy-isophthalamic acid example 13d

The title compound is made using methods described for Acid IVj.
LC/MS (Nucleosil C-18HD, 4×70 mm, 3 μM, 20-100% MeCN (6 min), 100% MeCN (1.5 min)): 4.23 min; MS(ES) [MH]$^+$=292.2, [MNa]$^+$=314.2 l) N-Allyl-5-methyl-N-ethyl-isophthalamic acid example 13e

The title compound is made using methods described for Acid IVj.
LC/MS (Nucleosil C-18HD, 4×70 mm, 3 μM, 20-100% MeCN (6 min), 100% MeCN (1.5 min)): 3.74 min; MS(ES) [MH]$^+$=248.2, [MNa]$^+$=270.2 m) N-Allyl-N-ethyl-5-methanesulfonyl-isophthalamic acid example 13f

The title compound is made using methods described for Acid IVj from 5-methanesulfonyl-isophthalic acid.
LC/MS (Nucleosil C-18HD, 4×70 mm, 3 μM, 20-100% MeCN (6 min), 100% MeCN (1.5 min)): 3.03 min; MS(ES) [MH]$^+$=312.0, [MNa]$^+$=334.0 n) N-Allyl-N-ethyl-5-oxazol-2-yl-isophthalamic acid example 13g

LC/MS (Nucleosil C-18HD, 4×70 mm, 3 μM, 20-100% MeCN (6 min), 100% MeCN (1.5 min)): 3.52 min; MS(ES) [MH]$^+$=301.2, [MNa]$^+$=323.2 o) N-But-3-enyl-N-ethyl-isophthalamic acid example 13h

The title compound is made using methods described for Acid IVc.
LC/MS (Nucleosil C-18HD, 4×70 mm, 3 μM, 20-100% MeCN (6 min), 100% MeCN (1.5 min)): 3.63 min; MS(ES) [MH]$^+$=248.2, [MNa]$^+$=270.2

Acids V

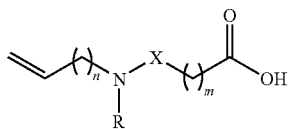

X=SO$_2$, C=O
R=H, Me
n=1-4
m=1-3 a) 3-(Methyl-pent-4-enyl-sulfamoyl)-propionic acid example 14

To a stirred suspension of 1.03 g (12.0 mmol) pent-4-enylamine, 8 ml DCM and 5 ml 10% aqueous Na$_2$CO$_3$ at 0° C. are added dropwise 2.25 g (12.0 mmol) 3-chlorosulfonyl-propionic acid methyl ester. After stirring for 2 h at 25° C. the phases are separated and the organic phase is dried with sodium sulfate and evaporated. Chromatography on silica gel (EtOAc, hexane 1:2) gives the 3-pent-4-enylsulfamoyl-propionic acid methyl ester. This ester is dissolved in 2 ml DMF and heated to 65° C. in the presence of 1.58 g (11.5 mmol) K$_2$CO$_3$ and 0.716 ml methyl iodide for 5 h. The mixture is diluted with EtOAc and washed with water, dried with sodium sulfate and evaporated. Chromatography on silica gel (EtOAc, hexane 1:4) gives the 3-(methyl-pent-4-enyl-sulfamoyl)-propionic acid methyl ester. Hydrolysis of this ester with LiOH in water/MeOH gives the title compound.
$^1$H-NMR (400 MHz, CDCl$_3$): 5.89-5.78 (m, 1H), 5.11-5.01 (m, 2H), 3.27 (t, 2H), 3.20 (t, 2H), 2.64 (t, 2H), 2.63 (s, 3H), 2.13 (q, 2),1.77-1.69 (m, 2H)
LC/MS (Nucleosil C-18HD, 4×70 mm, 3 μM, 20-100% MeCN (6 min), 100% MeCN (1.5 min)): 3.45 min; MS(ES), [MNa]$^+$=258.0 b) N-But-3-enyl-succinamic acid example 14a

A mixture of 0.71 g (10 mmol) but-3-enylamine and 1.0 g (10 mmol) succinic anhydride in 10 ml DCM is stirred for 16 h. The mixture is poured into 25 ml 1N NaOH, washed with TBME, acidified with 6 ml 6N HCl, saturated with NaCl and extracted with THF/EtOAc twice. The combined organic layers are dried with sodium sulfate and evaporated to yield the title compound.
$^1$H-NMR (400 MHz, CDCl$_3$): 5.86 (br, 1H), 5.86-5.74 (m, 1H), 5.17-5.10 (m, 2H), 3.38 (q, 2H), 2.74 (t, 2H), 2.54 (t, 2H), 2.30 (q, 3H)
LC/MS (Nucleosil C-18HD, 4×70 mm, 3 μM, 20-100% MeCN (6 min), 100% MeCN (1.5 min)): 1.29 min; MS(ES), [MNa]$^+$=194.0

The invention claimed is:
1. A compound of the formula

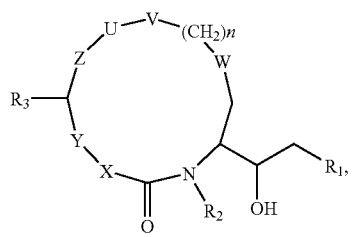

(I)

in which
$R_1$ is CH($R_e$)C(=O)N($R_a$)$R_b$ or (CH$_2$)$_k$N($R_c$)$R_d$, wherein k is 0, 1 or 2;

$R_a$ and $R_b$, independently, are hydrogen or an optionally substituted (C$_{1-8}$)alkyl, (C$_{3-7}$)cycloalkyl, (C$_{3-7}$)cycloalkyl(C$_{1-4}$)alkyl, aryl, aryl(C$_{1-4}$)alkyl, heteroaryl or heteroaryl(C$_{1-4}$)alkyl group, $R_c$ and $R_d$, independently, are hydrogen or an optionally substituted (C$_{1-8}$)alkyl, (C$_{3-7}$)cycloalkyl, (C$_{3-7}$)cycloalkyl(C$_{1-4}$)alkyl, aryl, aryl(C$_{1-4}$)alkyl, heteroaryl, heteroaryl(C$_{1-4}$)alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinolin-4-yl, 1,2,3,4-tetrahydro-isoquinolin-4-yl, 1,2,3,4-tetrahydro-naphthalen-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl or 1,3,4,5-tetrahydro-benzo[c]oxepin-5-yl group, or $R_a$ and $R_b$, or $R_c$ and $R_d$, together with the nitrogen to which they are attached, form an optionally substituted pyrrolidinyl, 1-piperidinyl, 4-morpholinyl or piperazinyl group; and $R_e$ is optionally substituted (C$_{1-8}$)alkyl, (C$_{1-4}$)alkoxy (C$_{1-4}$)alkyl, (C$_{3-7}$)cycloalkyl or (C$_{3-7}$)cycloalkyl (C$_{1-4}$) alkyl;

$R_2$ is hydrogen or (C$_{1-4}$)alkyl;

$R_3$ is hydrogen, (C$_{1-6}$)alkyl or an optionally substituted (C$_{1-6}$)alkylOC(=O)NH, (C$_{3-7}$)cycloalkylOC(=O)NH, (C$_{3-7}$)cycloalkyl(C$_{1-4}$)alkylOC(=O)NH, aryl(C$_{1-4}$) alkylOC(=O)NH, heteroaryl(C$_{1-4}$)alkylOC(=O)NH, (C$_{1-4}$)alkylC(=O)NH, (C$_{3-7}$)cycloalkylC(=O)NH, arylC(=O)NH, aryl(C$_{1-4}$)alkylC(=O)NH, heteroarylC(=O)NH or heteroaryl(C$_{1-4}$)alkylC(=O)NH group;

U is a bond;
V is CH=CH, CH$_2$CH(OH), CH(OH)CH$_2$ or CR$_h$R$_h$CR$_h$R$_h$, wherein each R$_h$, independently, is hydrogen, fluorine or (C$_{1-4}$)alkyl;

W is (C$_{1-6}$)alkylene;

X is an optionally substituted (C$_{1-4}$)alkanylylidene or (C$_{1-4}$) alkylene;

Y is C(=O)NR$_g$ or N(R$_g$)C(=O), wherein
R$_g$ is hydrogen, (C$_{1-8}$)alkyl or (C$_{3-7}$)cycloalkyl;

Z is a bond; and n is 0 to 5, the number of ring atoms included in the macrocyclic ring being 14, 15, 16 or 17, in free base form or in acid addition salt form.

2. A process for the preparation of a compound as defined in claim 1 of the formula I, in free base form or in acid addition salt form, comprising the steps of cyclisation by metathesis of a compound of the formula

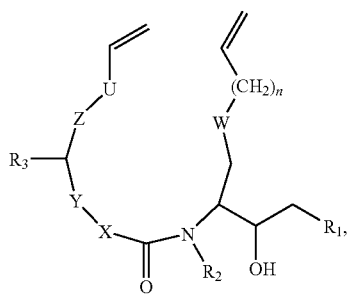

(II)

in which $R_1$, $R_2$, $R_3$, U, W, X, Y, Z and n are as defined for the formula I, in the presence of a catalyst, optionally followed by reduction, oxidation or functionalisation of the resulting carbon-carbon-double bond, and of recovering the so obtainable compound of the formula I in free base form or in acid addition salt form.

3. A pharmaceutical composition comprising a compound as claimed in claim 1, in free base form or in pharmaceutically acceptable acid addition salt form, as active ingredient and a pharmaceutical carrier or diluent.

* * * * *